United States Patent
Cook et al.

(10) Patent No.: US 11,274,143 B2
(45) Date of Patent: Mar. 15, 2022

(54) DECOY CYTOKINE RECEPTOR

(71) Applicants: Singapore Health Services PTE LTD, Singapore (SG); National University of Singapore, Singapore (SG)

(72) Inventors: Stuart Alexander Cook, Singapore (SG); Sebastian Schaefer, Singapore (SG)

(73) Assignees: National University of Singapore, Singapore (SG); Singapore Health Services Pte Ltd, Singapore (SG)

( * ) Notice: Subject to any disclaimer, the term of this patent is extended or adjusted under 35 U.S.C. 154(b) by 0 days.

(21) Appl. No.: 16/469,601

(22) PCT Filed: Dec. 15, 2017

(86) PCT No.: PCT/EP2017/083032
§ 371 (c)(1),
(2) Date: Jun. 13, 2019

(87) PCT Pub. No.: WO2018/109168
PCT Pub. Date: Jun. 21, 2018

(65) Prior Publication Data
US 2019/0345226 A1 Nov. 14, 2019

(30) Foreign Application Priority Data
Dec. 16, 2016 (GB) .................................. 1621431.4

(51) Int. Cl.
| | |
|---|---|
| C07K 14/715 | (2006.01) |
| A61K 47/64 | (2017.01) |
| A61P 27/02 | (2006.01) |
| A61P 9/00 | (2006.01) |
| A61P 17/00 | (2006.01) |
| A61P 13/12 | (2006.01) |
| A61P 11/00 | (2006.01) |
| A61P 35/00 | (2006.01) |
| G01N 33/68 | (2006.01) |
| A61K 38/00 | (2006.01) |

(52) U.S. Cl.
CPC ...... *C07K 14/7155* (2013.01); *A61K 47/6425* (2017.08); *A61P 9/00* (2018.01); *A61P 11/00* (2018.01); *A61P 13/12* (2018.01); *A61P 17/00* (2018.01); *A61P 27/02* (2018.01); *A61P 35/00* (2018.01); *G01N 33/6869* (2013.01); *A61K 38/00* (2013.01); *G01N 2333/7155* (2013.01)

(58) Field of Classification Search
CPC .............................................. C07K 14/7155
See application file for complete search history.

(56) References Cited

U.S. PATENT DOCUMENTS

| | | |
|---|---|---|
| 8,182,814 B2 | 5/2012 | Baca et al. |
| 2010/0183544 A1 | 7/2010 | Jenkins et al. |

FOREIGN PATENT DOCUMENTS

| | | |
|---|---|---|
| EP | 1630232 A1 | 3/2006 |
| WO | WO 1996/19574 A1 | 6/1996 |
| WO | WO 1999/20755 A2 | 4/1999 |
| WO | WO 2005/058956 A1 | 6/2005 |
| WO | WO 2009/052588 A1 | 4/2009 |
| WO | WO 2014/121325 A1 | 8/2014 |

OTHER PUBLICATIONS

Mikayama et al. Proc. Natl. Acad. Sci. USA (1993) vol. 90, pp. 10056-10060.*
Voet et al. Biochemistry John Wiley & Sons, Inc., (1990), pp. 126-128 and 228-234.*
Ancey et al., A fusion protein of the gp130 and interleukin-6Ralpha ligand-binding domains acts as a potent interleukin-6 inhibitor. J Biol Chem. May 9, 2003;278(19):16968-72. Epub Mar. 19, 2003.
Bravo et al., Crystal structure of a cytokine-binding region of gp130. EMBO J. Mar. 16, 1998;17(6):1665-74.
Chen et al., IL-11 receptor alpha in the pathogenesis of IL-13-induced inflammation and remodeling. J Immunol. Feb. 15, 2005;174(4):2305-13.
Chow et al., Structure of an extracellular gp130 cytokine receptor signaling complex. Science. Mar. 16, 2001;291(5511):2150-5.
Johnstone et al., Emerging roles for IL-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.
Lokau, et al. Signal transduction of interleukin-11 and interleukin-6 α-receptors. Receptor Clin Invest 2016;3:e1190. doi: 10.14800/rci.1190.
Metz et al., Characterization of the Interleukin (IL)-6 Inhibitor IL-6-RFP: fused receptor domains act as high affinity cytokine-binding proteins. J Biol Chem. Jan. 12, 2007;282(2):1238-48. Epub Nov. 3, 2006.
Putoczki et al., More than a sidekick: the IL-6 family cytokine IL-11 links inflammation to cancer. J Leukoc Biol. Dec. 2010;88(6):1109-17. doi:10.1189/jlb.0410226. Epub Jul. 7, 2010.
Affo et al., The Role of Cancer-Associated Fibroblasts and Fibrosis in Liver Cancer. Annu Rev Pathol. Jan. 24, 2017;12:153-186. Author manuscript, 39 pgs.
Blanc et al., Monoclonal antibodies against the human interleukin-11 receptor alpha-chain (IL-11Ralpha) and their use in studies of human mononuclear cells. J Immunol Methods. Jul. 31, 2000;241(1-2):43-59.
Buck et al., Detection of S-phase cell cycle progression using 5-ethynyl-2?-deoxyuridine incorporation with click chemistry, an alternative to using 5-bromo-2?-deoxyuridine antibodies. BioTechniques. Jun. 2008;44(7):927-929.
Chen et al., Fusion Protein Linkers: Property, Design and Functionality. Adv Drug Deliv Rev. Oct. 15, 2013;65(10):1357-1369. Author Manuscript, 32 pages.

(Continued)

*Primary Examiner* — Prema M Mertz
(74) *Attorney, Agent, or Firm* — Wolf, Greenfield & Sacks, P.C.

(57) ABSTRACT

An IL-11 binding receptor capable of binding to IL-11 and inhibiting IL-11 mediated signalling is disclosed. Also disclosed are compositions comprising the IL-11 binding receptor and methods using the IL-11 binding receptor.

3 Claims, 50 Drawing Sheets

Specification includes a Sequence Listing.

(56) References Cited

OTHER PUBLICATIONS

Ciliberto et al. Cytokine Inhibitors: Chapter 8. Marcel Dekker, Inc. 2001.

Concepcion et al., Label-free detection of biomolecular interactions using BioLayer interferometry for kinetic characterization. Comb Chem High Throughput Screen. Sep. 2009;12(8):791-800. doi: 10.2174/138620709789104915.

Daba et al., Drug-induced pulmonary fibrosis. Saudi Medical Journal. 2004;25(6):700-706.

Du et al., Interleukin-11: review of molecular, cell biology, and clinical use. Blood. Jun. 1, 1997;89(11):3897-908.

Elias et al., IL-1 and transforming growth factor-beta regulation of fibroblast-derived IL-11. J Immunol. Mar. 1, 1994;152(5):2421-9.

Ernst et al., STAT3 and STAT1 mediate IL-11-dependent and inflammation-associated gastric tumorigenesis in gp130 receptor mutant mice. The Journal of Clinical Investigation. May 2008;118(5):1727-1738.

Frank et al., High-performance signal peptide prediction based on sequence alignment techniques. Bioinformatics. 2008;24(19):2172-2176.

Fulcher et al., Carboxyfluorescein succinimidyl ester-based proliferative assays for assessment of T cell function in the diagnostic laboratory. Immunology and Cell Biology. 1999;77:559-564.

Garbers et al., Interleukin-6 and interleukin-11: same same but different. Biol Chem. Sep. 2013;394(9):1145-61. doi: 10.1515/hsz-2013-0166.

Gershoni et al., Epitope mapping: the first step in developing epitope-based vaccines. BioDrugs. 2007;21(3):145-56. doi: 10.2165/00063030-200721030-00002.

Gourdie et al., Novel therapeutic strategies targeting fibroblasts and fibrosis in heart disease. Nat Rev Drug Discov. Sep. 2016;15(9):620-638. Author Manuscript, 38 pages.

Griffin et al., 104 : The structure of human interleukin-11 reveals features of biological significance. Cytokine. Sep. 2013;63(3):267. doi: 10.1016/j.cyto.2013.06.107.

Grivennikov et al., Autocrine IL-6 signaling: a key event in tumorigenesis?. Cancer Cell. 2008;13(1):7-9.

Guo et al., Signaling cross-talk between TGF-?/BMP and other pathways. Cell Res. Jan. 2009;19(1):71-88, Author Manuscript, 27 pages.

Ham et al., Critical role of interleukin-11 in isoflurane-mediated protection against ischemic acute kidney injury in mice. Anesthesiology. Dec. 2013;119(6):1389-401. doi: 10.1097/ALN. 0b013e3182a950da.

Haverick et al., Separation of mAbs molecular variants by analytical hydrophobic interaction chromatography HPLC. mAbs. 2014;6(4):852-858. Epub Apr. 1, 2014.

Hearty et al., Measuring antibody-antigen binding kinetics using surface plasmon resonance. Methods Mol Biol. 2012;907:411-42. doi: 10.1007/978-1-61779-974-7_24.

Hilton et al., Cloning of a Murine IL-11 Receptor Alpha-Chain; Requirement for gp130 for High Affinity Binding and Signal Transduction. EMBO J. Oct. 17, 1994;13(20):4765-75.

Hinz et al., Biological Perspectives. The Myofibroblast. On Function, Multiple Origins. Am J Pathol. Jun. 2007;170(60):1807-1816. doi: 10.2353/ajpath.2007.070112.

Hsu et al., Whole genome expression differences in human left and right atria ascertained by RNA sequencing. Circ Cardiovasc Genet. 2012;5(3):327-335.

Jerabek-Willemsen et al., Molecular interaction studies using microscale thermophoresis. Assay and Drug Development Technologies. Aug. 2011;9(4):342-353.

Kapina et al., Interleukin-11 drives early lung inflammation during *Mycobacterium tuberculosis* infection in genetically susceptible mice. PLoS One. 2011;6(7):e21878. doi: 10.1371/journal.pone. 0021878.

Karpovich et al., Expression and Function of interleukin-11 and Its Receptor Alpha in the Human Endometrium. Mol Hum Reprod. Feb. 2003;9(2):75-80. doi: 10.1093/molehr/gag012.

Khaw et al., Modulation of wound healing after glaucoma surgery. Curr Opin Ophthalmol. Apr. 2001;12(2):143-8.

Kurahar er al., Significant contribution of TRPC6 channel-mediated Ca2+ influx to the pathogenesis of Crohn's disease fibrotic stenosis. Journal of Smooth Muscle Research. 2016;52:78-92. Epub Nov. 3, 2016.

Lacob et al., Investigating monoclonal antibody aggregation using a combination of H/DX-MS and other biophysical measurements. J Pharm Sci., Dec. 2013;102(12):4315-4329, Author Manuscript, 25 pages.

Lad et al., High-Throughput Kinetic Screening of Hybridomas to Identify High-Affinity Antibodies Using Bio-Layer Interferometry. Journal of Biomolecular Screening. 2015;20(4):498-507.

Leask et al., TGF?? signaling and the fibrotic response. The FASEB Journal. 2004;18:816-827.

Liang et al., In vitro scratch assay: a convenient and inexpensive method for analysis of cell migration in vitro. Nat Protoc. 2007;2(2):329-333.

Lindahl et al., Microarray profiling reveals suppressed interferon stimulated gene program in fibroblasts from scleroderma-associated interstitial lung disease. Respir Res. Aug. 2, 2013;14:80. doi: 10.1186/1465-9921-14-80.

Lokau et al., Proteolytic Cleavage Governs Interleukin-11 Trans-signaling. Cell Rep. 2016; 14(7): 1761-1773.

Martineau P., Affinity Measurements by Competition ELISA. Antibody Engineering. 2010;1:657-665.

Mead et al., Evaluation of Anti-TGF-2 Antibody as a New Postoperative Anti-scarring Agent in Glaucoma Surgery. IOVS. Aug. 2003;44(8):3394-3401.

Menzen et al., High-Throughput Melting-Temperature Analysis of a Monoclonal Antibody by Differential Scanning Fluorimetry in the Presence of Surfactants. Journal of Pharmaceutical Sciences. Feb. 2013;102(2):415-428.

Minshall et al., IL-11 expression is increased in severe asthma: association with epithelial cells and eosinophils. J Allergy Clin Immunol. Feb. 2000;105(2 Pt 1):232-8.

Nandurkar et al., The Human IL-11 Receptor Requires gp130 for Signalling: Demonstration by Molecular Cloning of the Receptor. Oncogene. Feb. 1, 1996;12(3):585-93.

Nanthakumar et al., Dissecting fibrosis: therapeutic insights from the small-molecule toolbox. Nature Reviews. Oct. 2015;14:693-720. Epub Sep. 4, 2015.

Obana et al., Therapeutic activation of signal transducer and activator of transcription 3 by interleukin-11 ameliorates cardiac fibrosis after myocardial infarction. Circulation. Feb. 9, 2010;121(5):684-91. doi: 10.1161/CIRCULATIONAHA. 109.893677. Epub Jan. 25, 2010.

Obana et al., Therapeutic activation of signal transducer and activator of transcription 3 by interleukin-11 ameliorates cardiac fibrosis after myocardial infarction. Circulation. Feb. 9, 2010;121(Supplemental Info). 14 pages. doi: 10.1161/CIRCULATIONAHA.109. 893677. Epub Jan. 25, 2010.

Obana et al., Therapeutic administration of IL-11 exhibits the postconditioning effects against ischemia-reperfusion injury via STAT3 in the heart. Am J Physiol Heart Circ Physiol. Sep. 1, 2012;303(5):H569-77. doi: 10.1152/ajpheart.00060.2012.

Petersen et al., SignalP 4.0: discriminating signal peptides from transmembrane regions. Nat Methods. Sep. 29, 2011;8(10):785-6. doi: 10.1038/nmeth.1701.

Pflanz et al., A Fusion Protein of interleukin-11 and Soluble interleukin-11 Receptor Acts as a Superagonist on Cells Expressing gp130. FEBS Lett. Apr. 30, 1999;450(1-2): 117-22. doi: 10.1016/s0014-5793(99)00477-9.

Putoczki et al., IL-11 signaling as a therapeutic target for cancer. Immunotherapy. 2015;7(4):441-53. doi: 10.2217/imt.15.17.

Putoczki et al., More Than a Sidekick: The IL-6 Family Cytokine IL-11 Links Inflammation to Cancer. J Leukoc Biol. Dec. 2010;88(6):1109-17. doi: 10.1189/jlb.0410226.

Putoczki et al., The structure of human interleukin-11 reveals receptor-binding site features and structural differences from interleukin-6. Acta Crystallogr D Biol Crystallogr. Sep. 2014;70(Pt9):2277-85. doi: 10.1107/S1399004714012267. Epub Aug. 23, 2014.

(56) References Cited

OTHER PUBLICATIONS

Rich et al., Extracting kinetic rate constants from surface plasmon resonance array systems. Analytical Biochemistry. 2008;373(1):112-120. Epub Aug. 19, 2007.

Rockey et al., Fibrosis—a common pathway to organ injury and failure. N Engl J Med. Mar. 19, 2015;372(12):1138-49. doi: 10.1056/NEJMra1300575.

Salic et al., A chemical method for fast and sensitive detection of DNA synthesis in vivo. PNAS. Feb. 19, 2008;105(7):2415-2420.

Schleinkofer et al., Identification of the domain in the human interleukin-11 receptor that mediates ligand binding. J Mol Biol. Feb. 16, 2001;306(2):263-74.

Seet et al., Validation of the Glaucoma Filtration Surgical Mouse Model for Antifibrotic Drug Evaluation. Mol Med. 2011;17(5-6):557-567. Epub Jan. 11, 2011.

Shepelkova et al., Therapeutic Effect of Recombinant Mutated Interleukin 11 in the Mouse Model of Tuberculosis. J Infect Dis. Aug. 1, 2016;214(3):496-501. doi: 10.1093/infdis/jiw176.

Sittampalam et al., Assay Guidance Manual, Eli Lilly & Company and the National Center for Advancing Translational Sciences. 2004 (last updated Jul. 1, 2016), 10 pages.

Stangou et al., Effect of IL-11 on glomerular expression of TGF-beta and extracellular matrix in nephrotoxic nephritis in Wistar Kyoto rats. J Nephrol. Jan.-Feb. 2011;24(1):106-11. Author Manuscript.

Szendroi et al., Polarization colours of collagen fibres: a sign of collagen production activity in fibrotic processes. Acta Morphol Hung. 1984;32(1):47-55.

Tang et al., Targeted expression of IL-11 in the murine airway causes lymphocytic inflammation, bronchial remodeling, and airways obstruction. J Clin Invest. Dec. 15, 1996;98(12):2845-53.

Tao et al., Cancer-associated fibroblasts treated with cisplatin facilitates chemoresistance of lung adenocarcinoma through IL-11/IL-11R/STAT3 signaling pathway. Sci Rep. Dec. 6, 2016;6:38408. doi: 10.1038/srep38408. 24 pages.

Toda et al., Polarized in vivo expression of IL-11 and IL-17 between acute and chronic skin lesions. J Allergy Clin Immunol. Apr. 2003;111(4):875-81.

Trepicchio et al., The therapeutic utility of Interleukin-11 in the treatment of inflammatory disease. Expert Opin Investig Drugs. Sep. 1998;7(9):1501-4.

Unverdorben et al., Pharmacokinetic properties of IgG and various Fc fusion proteins in mice. MAbs. 2016;8(1):120-128.

Walia et al., TGF-beta down-regulates IL-6 signaling in intestinal epithelial cells: critical role of SMAD-2. FASEB J. 2003;17(14):2130-2132.

Wong et al., Endogenous IL-11 is pro-inflammatory in acute methylated bovine serum albumin/interleukin-1-induced (mBSA/IL-1)arthritis. Cytokine. Jan. 21, 2005;29(2):72-6.

Wong et al., Matrix Metalloproteinase Inhibition Modulates Postoperative Scarring after Experimental Glaucoma Filtration Surgery. Investigative Ophthalmology & Visual Science. Mar. 2003;44(3):1097-1103.

Wong et al., Prolonged Antiscarring Effects of Ilomastat and MMC after Experimental Glaucoma Filtration Surgery. Investigative Ophthalmology & Visual Science. Jun. 2005;46(6):2018-2022.

Wynn et al., Mechanisms of fibrosis: therapeutic translation for fibrotic disease. Nat Med. 2012;18(7):1028-1040.

Wynn, Cellular and molecular mechanisms of fibrosis. J Pathol. Jan. 2008;214(2):199-210. Author Manuscript.

Xu et al., The role of IL-11 in immunity and cancer. Cancer Letters. 2016;373:156-163.

Zhang et al., IL-11 in multiple sclerosis. Oncotarget. Oct. 7, 2015;6(32):32297-32298.

Zheng et al., IL-11: insights in asthma from overexpression transgenic modeling. J Allergy Clin Immunol. Oct. 2001;108(4):489-96.

PCT/EP2017/083032, dated Apr. 17, 2018, International Search Report and Written Opinion.

\* cited by examiner

Decoy IL-11 Receptor 1 (D11R1):
*MLTLQTWLVQALFIFLTTESTG*ELLDPCGYISPESPVVQLHSNFTAVCVLKEK
CMDYFHVNANYIVWKTNHFTIPKEQYTIINRTASSVTFTDIASLNIQLTCNIL
TFGQLEQNVYGITIISGLPPEKPKNLSCIVNEGKKMRCEWDGGRETHLETNFT
LKSEWATHKFADCKAKRDTPTSCTVDYSTVYFVNIEVWVEAENALGKVTSDHI
NFDPVYKVKPNPPHNLSVINSEELSSILKLTWTNPSIKSVIILKYNIQYRTKD
ASTWSQIPPEDTASTRSSFTVQDLKPFTEYVFRIRCMKEDGKGYWSDWSEEAS
GITYEDRPGGGGSTRGQLHTQPEVEPQVDSPAPPRPSLQPHPRLLDHRDSVEQ
VAVGSLGYPPARPVVSCQAADYENFSCTWSPSQISGLPTRYLTSYRKKTVLGA
DSQRRSPSTGPWPCPQDPLGAARCVVHGAEFWSQYRINVTEVNPLGASTRLLD
VSLQSILRPDPPQGLRVESVPGYPRRLRASWTYPASWPCQPHFLLKFRLQYRP
AQHPAWSTVEPAGLEEVITDAVAGLPHAVRVSARDFLDAGTWSTWSPEAWGTP
STGDYKDDDDK (SEQ ID NO:1)

Leader Sequence:
*MLTLQTWLVQALFIFLTTESTG* (SEQ ID NO:3)

Sgp130 (D1, D2 and D3):
ELLDPCGYISPESPVVQLHSNFTAVCVLKEKCMDYFHVNANYIVWKTNHFTIP
KEQYTIINRTASSVTFTDIASLNIQLTCNILTFGQLEQNVYGITIISGLPPEK
PKNLSCIVNEGKKMRCEWDGGRETHLETNFTLKSEWATHKFADCKAKRDTPTS
CTVDYSTVYFVNIEVWVEAENALGKVTSDHINFDPVYKVKPNPPHNLSVINSE
ELSSILKLTWTNPSIKSVIILKYNIQYRTKDASTWSQIPPEDTASTRSSFTVQ
DLKPFTEYVFRIRCMKEDGKGYWSDWSEEASGITYEDRP (SEQ ID NO:4)

Linker (50aa):
GGGGSTRGQLHTQPEVEPQVDSPAPPRPSLQPHPRLLDHRDSVEQVAVGS (SEQ ID NO:5)

IL-11Rα (D2 and D3):
LGYPPARPVVSCQAADYENFSCTWSPSQISGLPTRYLTSYRKKTVLGADSQRR
SPSTGPWPCPQDPLGAARCVVHGAEFWSQYRINVTEVNPLGASTRLLDVSLQS
ILRPDPPQGLRVESVPGYPRRLRASWTYPASWPCQPHFLLKFRLQYRPAQHPA
WSTVEPAGLEEVITDAVAGLPHAVRVSARDFLDAGTWSTWSPEAWGTPSTG
(SEQ ID NO:6)

FLAG tag:
DYKDDDDK (SEQ ID NO:7)

Figure 17A

Decoy IL-11 Receptor 2 (D11R2):
*MLTLQTWLVQALFIFLTTESTG*ELLDPCGYISPESPVVQLHSNFTAVCVLKEK
CMDYFHVNANYIVWKTNHFTIPKEQYTIINRTASSVTFTDIASLNIQLTCNIL
TFGQLEQNVYGITIISGLPPEKPKNLSCIVNEGKKMRCEWDGGRETHLETNFT
LKSEWATHKFADCKAKRDTPTSCTVDYSTVYFVNIEVWVEAENALGKVTSDHI
NFDPVYKVKPNPPHNLSVINSEELSSILKLTWTNPSIKSVIILKYNIQYRTKD
ASTWSQIPPEDTASTRSSFTVQDLKPFTEYVFRIRCMKEDGKGYWSDWSEEAS
GITYEDRPGGGGSTRGSAGSGGSATGSGSAAGSGDSVRRGSLGYPPARPVVSC
QAADYENFSCTWSPSQISGLPTRYLTSYRKKTVLGADSQRRSPSTGPWPCPQD
PLGAARCVVHGAEFWSQYRINVTEVNPLGASTRLLDVSLQSILRPDPPQGLRV
ESVPGYPRRLRASWTYPASWPCQPHFLLKFRLQYRPAQHPAWSTVEPAGLEEV
ITDAVAGLPHAVRVSARDFLDAGTWSTWSPEAWGTPSTGDYKDDDDK (SEQ ID
NO:2)

Leader Sequence:
*MLTLQTWLVQALFIFLTTESTG* (SEQ ID NO:3)

Sgp130 (D1, D2 and D3):
ELLDPCGYISPESPVVQLHSNFTAVCVLKEKCMDYFHVNANYIVWKTNHFTIP
KEQYTIINRTASSVTFTDIASLNIQLTCNILTFGQLEQNVYGITIISGLPPEK
PKNLSCIVNEGKKMRCEWDGGRETHLETNFTLKSEWATHKFADCKAKRDTPTS
CTVDYSTVYFVNIEVWVEAENALGKVTSDHINFDPVYKVKPNPPHNLSVINSE
ELSSILKLTWTNPSIKSVIILKYNIQYRTKDASTWSQIPPEDTASTRSSFTVQ
DLKPFTEYVFRIRCMKEDGKGYWSDWSEEASGITYEDRP (SEQ ID NO:4)

Linker (33aa):
GGGGSTRGSAGSGGSATGSGSAAGSGDSVRRGS (SEQ ID NO:8)

IL-11Rα (D2 and D3):
LGYPPARPVVSCQAADYENFSCTWSPSQISGLPTRYLTSYRKKTVLGADSQRR
SPSTGPWPCPQDPLGAARCVVHGAEFWSQYRINVTEVNPLGASTRLLDVSLQS
ILRPDPPQGLRVESVPGYPRRLRASWTYPASWPCQPHFLLKFRLQYRPAQHPA
WSTVEPAGLEEVITDAVAGLPHAVRVSARDFLDAGTWSTWSPEAWGTPSTG
(SEQ ID NO:6)

FLAG tag:
DYKDDDDK (SEQ ID NO:7)

Figure 17B

Decoy IL-11 Receptor 1 (D11R1):
  EcoRI    Kozak
GAATTCCCGCCGCCACC*ATGCTGACCCTGCAGACATGGCTGGTGCAGGCCCTGTTCATCTTC*
*CTGACCACCGAGAGCACCGGC*GAGCTGCTGGATCCTTGCGGCTACATCAGCCCCGAGAGCCC
TGTGGTGCAGCTGCATAGCAACTTCACCGCCGTGTGCGTGCTGAAAGAAAAGTGCATGGACT
ACTTCCACGTGAACGCCAACTACATCGTGTGGAAAACAAACCACTTCACCATCCCCAAAGAG
CAGTACACCATCATCAACCGGACCGCCAGCAGCGTGACCTTCACCGATATCGCCAGCCTGAA
CATCCAGCTGACCTGCAACATCCTGACCTTCGGCCAGCTGGAACAGAACGTGTACGGCATCA
CAATCATCAGCGGCCTGCCCCCGAGAAGCCCAAGAACCTGAGCTGCATCGTGAACGAGGGC
AAGAAAATGAGATGCGAGTGGGACGGCGGCAGAGAGACACACCTGGAAACAAACTTCACCCT
GAAGTCCGAGTGGGCCACCCACAAGTTCGCCGACTGCAAGGCCAAGAGGGACACCCCCACCA
GCTGTACCGTGGACTACAGCACCGTGTACTTCGTGAACATCGAAGTGTGGGTGGAAGCCGAG
AACGCCCTGGGCAAAGTGACCAGCGACCACATCAACTTCGACCCTGTGTACAAAGTGAAGCC
CAACCCCCCCACAACCTGAGCGTGATCAACAGCGAGGAACTGAGCAGCATCCTGAAGCTGA
CATGGACCAACCCCAGCATCAAGTCCGTGATCATTCTGAAGTACAACATCCAGTACCGGACC
AAGGACGCCAGCACCTGGTCCAGATCCCCCCTGAGGATACCGCCTCCACCCGGTCCAGCTT
CACAGTGCAGGACCTGAAGCCTTTCACCGAGTACGTGTTCCGGATCAGATGCATGAAGGAAG
ATGGCAAGGGCTACTGGAGCGATTGGAGCGAGGAAGCCAGCGGCATCACCTACGAGGACAGA
CCTGGCGGCGGAGGCTCTACAAGAGGCCAGCTGCACACTCAGCCCGAGGTGGAACCTCAGGT
GGACTCTCCTGCCCCTCCTAGACCTAGCCTGCAGCCCCATCCCAGACTGCTGGACCACAGAG
ACAGCGTGGAACAGGTGGCCGTGGGCAGCCTGGGATATCCTCCTGCTAGACCCGTGGTGTCC
TGCCAGGCCGCCGACTACGAGAACTTCTCCTGCACATGGTCCCCAGCCAGATCTCCGGCCT
GCCTACCAGATACCTGACCAGCTACCGGAAGAAAACCGTGCTGGGCGCCGACAGCCAGAGAA
GAAGCCCTTCTACAGGCCCCTGGCCCTGCCCTCAGGATCCTCTGGGAGCTGCCAGATGTGTG
GTGCACGGCGCCGAGTTTTGGAGCCAGTACAGAATCAACGTGACCGAAGTGAACCCCCTGGG
CGCCAGCACAAGGCTGCTGGACGTGTCCCTGCAGAGCATCCTGCGGCCTGATCCTCCACAGG
GACTGCGGGTGGAAAGCGTGCCAGGCTACCCCAGAAGGCTGAGAGCCTCCTGGACATACCCC
GCTAGCTGGCCTTGCCAGCCCCACTTCCTGCTGAAGTTCCGGCTGCAGTACCGGCCAGCCCA
GCATCCAGCTTGGAGCACAGTGGAACCTGCCGGCCTGGAAGAAGTGATCACAGACGCCGTGG
CCGGACTGCCTCATGCTGTGCGGGTGTCCGCCAGAGACTTTCTGGATGCCGGAACCTGGTCC
ACTTGGAGCCCAGAGGCTTGGGGCACACCTTCCACCGGCGACTACAAGGACGACGACGACAA
GTGATAAGCTT (SEQ ID NO:9)
 Stp HindIII

Leader Sequence:
*ATGCTGACCCTGCAGACATGGCTGGTGCAGGCCCTGTTCATCTTCCTGACCACCGAGAGCAC*
*CGGC* (SEQ ID NO:11)

Figure 18A

Sgp130 (D1, D2 and D3):
GAGCTGCTGGATCCTTGCGGCTACATCAGCCCCGAGAGCCCTGTGGTGCAGCTGCATAGCAA
CTTCACCGCCGTGTGCGTGCTGAAAGAAAAGTGCATGGACTACTTCCACGTGAACGCCAACT
ACATCGTGTGGAAAACAAACCACTTCACCATCCCCAAAGAGCAGTACACCATCATCAACCGG
ACCGCCAGCAGCGTGACCTTCACCGATATCGCCAGCCTGAACATCCAGCTGACCTGCAACAT
CCTGACCTTCGGCCAGCTGGAACAGAACGTGTACGGCATCACAATCATCAGCGGCCTGCCCC
CCGAGAAGCCCAAGAACCTGAGCTGCATCGTGAACGAGGGCAAGAAAATGAGATGCGAGTGG
GACGGCGGCAGAGAGACACACCTGGAAACAAACTTCACCCTGAAGTCCGAGTGGGCCACCCA
CAAGTTCGCCGACTGCAAGGCCAAGAGGGACACCCCCACCAGCTGTACCGTGGACTACAGCA
CCGTGTACTTCGTGAACATCGAAGTGTGGGTGGAAGCCGAGAACGCCCTGGGCAAAGTGACC
AGCGACCACATCAACTTCGACCCTGTGTACAAAGTGAAGCCCAACCCCCCCACAACCTGAG
CGTGATCAACAGCGAGGAACTGAGCAGCATCCTGAAGCTGACATGGACCAACCCCAGCATCA
AGTCCGTGATCATTCTGAAGTACAACATCCAGTACCGGACCAAGGACGCCAGCACCTGGTCC
CAGATCCCCCCTGAGGATACCGCCTCCACCCGGTCCAGCTTCACAGTGCAGGACCTGAAGCC
TTTCACCGAGTACGTGTTCCGGATCAGATGCATGAAGGAAGATGGCAAGGGCTACTGGAGCG
ATTGGAGCGAGGAAGCCAGCGGCATCACCTACGAGGACAGACCT (SEQ ID NO:12)

Linker (50aa):
GGCGGCGGAGGCTCTACAAGAGGCCAGCTGCACACTCAGCCCGAGGTGGAACCTCAGGTGGA
CTCTCCTGCCCCTCCTAGACCTAGCCTGCAGCCCCATCCCAGACTGCTGGACCACAGAGACA
GCGTGGAACAGGTGGCCGTGGGCAGC (SEQ ID NO:13)

IL-11Rα (D2 and D3):
CTGGGATATCCTCCTGCTAGACCCGTGGTGTCCTGCCAGGCCGCCGACTACGAGAACTTCTC
CTGCACATGGTCCCCCAGCCAGATCTCCGGCCTGCCTACCAGATACCTGACCAGCTACCGGA
AGAAAACCGTGCTGGGCGCCGACAGCCAGAGAAGAAGCCCTTCTACAGGCCCCTGGCCCTGC
CCTCAGGATCCTCTGGGAGCTGCCAGATGTGTGGTGCACGGCGCCGAGTTTTGGAGCCAGTA
CAGAATCAACGTGACCGAAGTGAACCCCCTGGGCGCCAGCACAAGGCTGCTGGACGTGTCCC
TGCAGAGCATCCTGCGGCCTGATCCTCCACAGGGACTGCGGGTGGAAAGCGTGCCAGGCTAC
CCCAGAAGGCTGAGAGCCTCCTGGACATACCCCGCTAGCTGGCCTTGCCAGCCCCACTTCCT
GCTGAAGTTCCGGCTGCAGTACCGGCCAGCCCAGCATCCAGCTTGGAGCACAGTGGAACCTG
CCGGCCTGGAAGAAGTGATCACAGACGCCGTGGCCGGACTGCCTCATGCTGTGCGGGTGTCC
GCCAGAGACTTTCTGGATGCCGGAACCTGGTCCACTTGGAGCCCAGAGGCTTGGGGCACACC
TTCCACCGGC (SEQ ID NO:14)

FLAG tag:
GACTACAAGGACGACGACGACAAG (SEQ ID NO:15)

Figure 18A (Cont.)

Decoy IL-11 Receptor 2 (D11R2):
```
  EcoRI    Kozak
GAATTCCCGCCGCCACCATGCTGACCCTGCAGACATGGCTGGTGCAGGCCCTGTTCATCTTC
CTGACCACCGAGAGCACCGGCGAGCTGCTGGATCCTTGCGGCTACATCAGCCCCGAGAGCCC
TGTGGTGCAGCTGCATAGCAACTTCACCGCCGTGTGCGTGCTGAAAGAAAAGTGCATGGACT
ACTTCCACGTGAACGCCAACTACATCGTGTGGAAAACAAACCACTTCACCATCCCCAAAGAG
CAGTACACCATCATCAACCGGACCGCCAGCAGCGTGACCTTCACCGATATCGCCAGCCTGAA
CATCCAGCTGACCTGCAACATCCTGACCTTCGGCCAGCTGGAACAGAACGTGTACGGCATCA
CAATCATCAGCGGCCTGCCCCCGAGAAGCCAAGAACCTGAGCTGCATCGTGAACGAGGGC
AAGAAAATGAGATGCGAGTGGGACGGCGGCAGAGAGACACACCTGGAAACAAACTTCACCCT
GAAGTCCGAGTGGGCCACCCACAAGTTCGCCGACTGCAAGGCCAAGAGGGACACCCCCACCA
GCTGTACCGTGGACTACAGCACCGTGTACTTCGTGAACATCGAAGTGTGGGTGGAAGCCGAG
AACGCCCTGGGCAAAGTGACCAGCGACCACATCAACTTCGACCCTGTGTACAAAGTGAAGCC
CAACCCCCCCCACAACCTGAGCGTGATCAACAGCGAGGAACTGAGCAGCATCCTGAAGCTGA
CATGGACCAACCCCAGCATCAAGTCCGTGATCATTCTGAAGTACAACATCCAGTACCGGACC
AAGGACGCCAGCACCTGGTCCCAGATCCCCCCTGAGGATACCGCCTCCACCCGGTCCAGCTT
CACAGTGCAGGACCTGAAGCCTTTCACCGAGTACGTGTTCCGGATCAGATGCATGAAGGAAG
ATGGCAAGGGCTACTGGAGCGATTGGAGCGAGGAAGCCAGCGGCATCACCTACGAGGACAGA
CCTGGCGGCGGAGGCAGCACAAGAGGATCTGCTGGAAGCGGCGGAAGCGCCACAGGCTCTGG
ATCTGCAGCTGGCAGCGGAGACTCTGTGCGGAGAGGCTCTCTGGGCTACCCTCCTGCTAGAC
CCGTGGTGTCTTGTCAGGCCGCCGACTACGAGAACTTCAGCTGCACATGGTCCCCAGCCAG
ATCTCCGGCCTGCCTACCAGATACCTGACCAGCTACCGGAAGAAAACCGTGCTGGGCGCCGA
CAGCCAGAGAAGAAGCCCTTCTACAGGCCCCTGGCCCTGCCCTCAGGATCCTCTGGGAGCTG
CCAGATGTGTGGTGCACGGCGCCGAGTTTTGGAGCCAGTACAGAATCAACGTGACCGAAGTG
AACCCCCTGGGCGCCAGCACTAGACTGCTGGATGTGTCCCTGCAGAGCATCCTGCGGCCCGA
TCCTCCACAGGGACTGAGAGTGGAAAGCGTGCCCGGCTACCCAGAAGGCTGAGAGCCTCCT
GGACATACCCCGCTAGCTGGCCTTGCCAGCCCCACTTCCTGCTGAAGTTTCGGCTGCAGTAC
CGGCCAGCCCAGCACCCTGCTTGGAGCACAGTGGAACCTGCCGGCCTGGAAGAAGTGATCAC
AGACGCCGTGGCCGGACTGCCTCATGCTGTGCGGGTGTCCGCCAGAGACTTTCTGGATGCCG
GAACCTGGTCCACTTGGAGCCCTGAGGCTTGGGGCACACCTTCCACCGGCGACTACAAGGAC
GACGACGACAAGTGATAAGCTT   (SEQ ID NO:10)
                   Stp  HindIII
```

Leader Sequence:
ATGCTGACCCTGCAGACATGGCTGGTGCAGGCCCTGTTCATCTTCCTGACCACCGAGAGCAC
CGGC (SEQ ID NO:11)

Figure 18B

Sgp130 (D1, D2 and D3):
GAGCTGCTGGATCCTTGCGGCTACATCAGCCCCGAGAGCCCTGTGGTGCAGCTGCATAGCAA
CTTCACCGCCGTGTGCGTGCTGAAAGAAAAGTGCATGGACTACTTCCACGTGAACGCCAACT
ACATCGTGTGGAAAACAAACCACTTCACCATCCCCAAAGAGCAGTACACCATCATCAACCGG
ACCGCCAGCAGCGTGACCTTCACCGATATCGCCAGCCTGAACATCCAGCTGACCTGCAACAT
CCTGACCTTCGGCCAGCTGGAACAGAACGTGTACGGCATCACAATCATCAGCGGCCTGCCCC
CGAGAAGCCCAAGAACCTGAGCTGCATCGTGAACGAGGGCAAGAAAATGAGATGCGAGTGG
GACGGCGGCAGAGAGACACACCTGGAAACAAACTTCACCCTGAAGTCCGAGTGGGCCACCCA
CAAGTTCGCCGACTGCAAGGCCAAGAGGGACACCCCCACCAGCTGTACCGTGGACTACAGCA
CCGTGTACTTCGTGAACATCGAAGTGTGGGTGGAAGCCGAGAACGCCCTGGGCAAAGTGACC
AGCGACCACATCAACTTCGACCCTGTGTACAAAGTGAAGCCCAACCCCCCCACAACCTGAG
CGTGATCAACAGCGAGGAACTGAGCAGCATCCTGAAGCTGACATGGACCAACCCCAGCATCA
AGTCCGTGATCATTCTGAAGTACAACATCCAGTACCGGACCAAGGACGCCAGCACCTGGTCC
CAGATCCCCCCTGAGGATACCGCCTCCACCGGTCCAGCTTCACAGTGCAGGACCTGAAGCC
TTTCACCGAGTACGTGTTCCGGATCAGATGCATGAAGGAAGATGGCAAGGGCTACTGGAGCG
ATTGGAGCGAGGAAGCCAGCGGCATCACCTACGAGGACAGACCT (SEQ ID NO:12)

Linker (33aa):
GGCGGCGGAGGCAGCACAAGAGGATCTGCTGGAAGCGGCGGAAGCGCCACAGGCTCTGGATC
TGCAGCTGGCAGCGGAGACTCTGTGCGGAGAGGCTCT (SEQ ID NO:16)

IL-11Rα (D2 and D3):
CTGGGATATCCTCCTGCTAGACCCGTGGTGTCCTGCCAGGCCGCCGACTACGAGAACTTCTC
CTGCACATGGTCCCCCAGCCAGATCTCCGGCCTGCCTACCAGATACCTGACCAGCTACCGGA
AGAAAACCGTGCTGGGCGCCGACAGCCAGAGAAGAAGCCCTTCTACAGGCCCCTGGCCCTGC
CCTCAGGATCCTCTGGGAGCTGCCAGATGTGTGGTGCACGGCGCCGAGTTTTGGAGCCAGTA
CAGAATCAACGTGACCGAAGTGAACCCCCTGGGCGCCAGCACAAGGCTGCTGGACGTGTCCC
TGCAGAGCATCCTGCGGCCTGATCCTCCACAGGGACTGCGGGTGGAAAGCGTGCCAGGCTAC
CCCAGAAGGCTGAGAGCCTCCTGGACATACCCCGCTAGCTGGCCTTGCCAGCCCACTTCCT
GCTGAAGTTCCGGCTGCAGTACCGGCCAGCCCAGCATCCAGCTTGGAGCACAGTGGAACCTG
CCGGCCTGGAAGAAGTGATCACAGACGCCGTGGCCGGACTGCCTCATGCTGTGCGGGTGTCC
GCCAGAGACTTTCTGGATGCCGGAACCTGGTCCACTTGGAGCCCAGAGGCTTGGGGCACACC
TTCCACCGGC (SEQ ID NO:14)

FLAG tag:
GACTACAAGGACGACGACGACAAG (SEQ ID NO:15)

Figure 18B (Cont.)

```
mousegp130ECD    QLLEPCGYIYPEFPVVQRGSNFTAICVLKEACLQHYYVNASYIVWKTNHAAVPREQVTVI
humangp130ECD    ELLDPCGYISPESPVVQLHSNFTAVCVLKEKCMDYFHVNANYIVWKTNHFTIPKEQYTII
                 ::*  ** *:*** *:::::*.****** ::*:** *:* mousegp130ECD    NRTTSSVTFTDVVLPSVQLTCNILSFGQIEQNVYGVTMLSGFPPDKPTNLTCIVNEGKNM
humangp130ECD    NRTASSVTFTDIASLNIQLTCNILTFGQLEQNVYGITIISGLPPEKPKNLSCIVNEGKKM
                 *:***:. .:***:*:******:*::::.:*******:* mousegp130ECD    LCQWDPGRETYLETNYTLKSEWATEKFPDCQSKHG--TSCMVSYMPTYYVNIEVWVEAEN
humangp130ECD    RCEWDGGRETHLETNFTLKSEWATHKFADCKAKRDTPTSCTVDYSTVYFVNIEVWVEAEN
                 *: ::**** :.*:.*: .   *** *.* .*:********** mousegp130ECD    ALGKVSSESINFDPVDKVKPTPPYNLSVTNSEELSSILKLSWVSSGLGGLLDLKSDIQYR
humangp130ECD    ALGKVTSDHINFDPVYKVKPNPPHNLSVINSEELSSILKLTWTNPSIKSVIILKYNIQYR
                 *****:*:* ****** ****.**:****:**********:*.. .: .:: ** :****

mousegp130ECD    TKDASTWIQVPLEDTMSPRTSFTVQDLKPFTEYVFRIRSIKDSGKGYWSDWSEEASGTTY
humangp130ECD    TKDASTWSQIPPEDTASTRSSFTVQDLKPFTEYVFRIRCMKEDGKGYWSDWSEEASGITY
                 ******* *:* *** * *:***************:*.:*.************ mousegp130ECD    EDRPSRPPSFWYKTNPSHGQEYRSVRLIWKALPLSEANGKILDYEVILTQSKSVSQTYTV
humangp130ECD    EDRPSKAPSFWYKIDPSHTQGYRTVQLVWKTLPPFEANGKILDYEVTLTRWKSHLQNYTV
                 ***:** :* * **:*:*:. ********* : ** *.*** mousegp130ECD    TGTELTVNLTNDRYVASLAARNKVGKSAAAVLTIPSPHVTAAYSVVNLKAFPKDNLLWVE
humangp130ECD    NATKLTVNLTNDRYLATLTVRNLVGKSDAAVLTIPACDFQATHPVMDLKAFPKDNMLWVE
                 ..:***********:*:*:.** **** ******:  .. *:: *:*********:****

mousegp130ECD    WTPPPKPVSKYILEWCVLSENAPCVEDWQQEDATVNRTHLRGRLLESRCYQITVTPVFAT
humangp130ECD    WTTPRESVKKYILEWCVLSDKAPCITDWQQEDGTVHRTYLRGNLAESRCYLITVTPVYAD
                 ** * : *.*******::*: *****.::*.*.***:****:* mousegp130ECD    GPGGSESLKAYLKQAAPARGPTVRTKKVGKNEAVLAWDQIPVDDQNGFIRNYSISYRTSV
humangp130ECD    GPGSPESIKAYLKQAPPSKGPTVRTKKVGKNEAVLEWDQLPVDQNGFIRNYTIFYRTII
                 ***. **:****** *::**************** ***:***:*********:* *** :

mousegp130ECD    GKEMVVHVDSSHTEYTLSSLSSDTLYMVRMAAYTDEGGKDGPEFTFTTPKFAQGEIE (SEQ
ID NO:23)
humangp130ECD    GNETAVNVDSSHTEYTLSSLTSDTLYMVRMAAYTDEGGKDGPEFTFTTPKFAQGEIE (SEQ
ID NO:24)
                 *:* .*:.*******:****:***************************************

73.45% sequence identity
```

Figure 20A

```
mousegp130D1-D3      EPCGYIYPEFPVVQRGSNFTAICVLKEACLQHYYVNASYIVWKTNHAAVPREQVTVINRT
humangp130D1-D3      DPCGYISPESPVVQLHSNFTAVCVLKEKCMDYFHVNANYIVWKTNHFTIPKEQYTIINRT
                     :***  **    :*** *::::* ******  :*:** *:**** mousegp130D1-D3      TSSVTFTDVVLPSVQLTCNILSFGQIEQNVYGVTMLSGFPPDKPTNLTCIVNEGKNMLCQ
humangp130D1-D3      ASSVTFTDIASLNIQLTCNILTFGQLEQNVYGITIISGLPPEKPKNLSCIVNEGKKMRCE
                     :******:.  .:******:***:*****:*::**:**.**:*********:* *:

mousegp130D1-D3      WDPGRETYLETNYTLKSEWATEKFPDCQSKHG--TSCMVSYMPTYYVNIEVWVEAENALG
humangp130D1-D3      WDGGRETHLETNFTLKSEWATHKFADCKAKRDTPTSCTVDYSTVYFVNIEVWVEAENALG
                      ::**** : **:*   ***.*.  .*:*************** mousegp130D1-D3      KVSSESINFDPVDKVKPTPPYNLSVTNSEELSSILKLSWVSSGLGGLLDLKSDIQYRTKD
humangp130D1-D3      KVTSDHINFDPVYKVKPNPPHNLSVINSEELSSILKLTWTNPSIKSVIILKYNIQYRTKD
                     **:*: **** .:**:*********:*..  .: .::  :**** mousegp130D1-D3      ASTWIQVPLEDTMSPRTSFTVQDLKPFTEYVFRIRSIKDSGKGYWSDWSEEASGTT (SEQ
ID NO:25)
humangp130D1-D3      ASTWSQIPPEDTASTRSSFTVQDLKPFTEYVFRIRCMKEDGKGYWSDWSEEASGIT(SEQ
ID NO:19)
                     **** *:* *** * *:*****************.:*:.********** *

71.43% sequence identity
```

Figure 20B

```
mouseIL11RaECD    SSPCPQAWGPPGVQYGQPGRPVMLCCPGVSAGTPVSWFRDGDSRLLQGPDSGLGHRLVLA
humanIL11RaECD    SSPCPQAWGPPGVQYGQPGRSVKLCCPGVTAGDPVSWFRDGEPKLLQGPDSGLGHELVLA
                  ******************** * ****  ******  ******** ** mouseIL11RaECD    QVDSPDEGTYVCQTLDGVSGGMVTLKLGFPPARPEVSCQAVDYENFSCTWSPGQVSGLPT
humanIL11RaECD    QADSTDEGTYICQTLDGALGGTVTLQLGYPPARPVVSCQAADYENFSCTWSPSQISGLPT
                  *  *:**   *::** *** ******** * ***** mouseIL11RaECD    RYLTSYRKKTLPGAESQRESPSTGPWPCPQDPLEASRCVVHGAEFWSEYRINVTEVNPLG
humanIL11RaECD    RYLTSYRKKTVLGADSQRRSPSTGPWPCPQDPLGAARCVVHGAEFWSQYRINVTEVNPLG
                  ********: .* *********** *  ********:********** mouseIL11RaECD    ASTCLLDVRLQSILRPDPPQGLRVESVPGYPRPLHASWTYPASWRRQPHFLLKFRLQYRP
humanIL11RaECD    ASTRLLDVSLQSILRPDPPQGLRVESVPGYPRPLRASWTYPASWPCQPHFLLKFRLQYRP
                  *  ********************:*****  ************ mouseIL11RaECD    AQHPAWSTVEPIGLEEVITDAVAGLPHAVRVSARDFLDAGTWSAWSPEAWGTPSTGPLQD
humanIL11RaECD    AQHPAWSTVEPAGLEEVITDAVAGLPHAVRVSARDFLDAGTWSTWSPEAWGTPSTGTIPK
                  *********** ******************************:*********** : .

mouseIL11RaECD    EIPDWSQGHGQQLEAVVAQEDSPAPARPSLQPDPRPLDHRDPLEQVAVLA (SEQ ID
NO:26)
humanIL11RaECD    EIPAWGQLHTQP--EVEPQVDSPAPPRPSLQPHPRLLDHRDSVEQVAVLA (SEQ ID
NO:27)
                  *** *.* * *    *  ***** ****** ** ***** ;*******

85.06% sequence identity
```

Figure 21A

```
mouseIL11RaD2-D3    PPARPEVSCQAVDYENFSCTWSPGQVSGLPTRYLTSYRKKTLPGAESQRESPSTGPWPCP
humanIL11RaD2-D3    PPARPVVSCQAADYENFSCTWSPSQISGLPTRYLTSYRKKTVLGADSQRRSPSTGPWPCP
                    *** *.******** *:************: :*.********* mouseIL11RaD2-D3    QDPLEASRCVVHGAEFWSEYRINVTEVNPLGASTCLLDVRLQSILRPDPPQGLRVESVPG
humanIL11RaD2-D3    QDPLGAARCVVHGAEFWSQYRINVTEVNPLGASTRLLDVSLQSILRPDPPQGLRVESVPG
                    **** *:*********:*********** .***************** mouseIL11RaD2-D3    YPRRLHASWTYPASWRRQPHFLLKFRLQYRPAQHPAWSTVEPIGLEEVITDAVAGLPHAV
humanIL11RaD2-D3    YPRRLRASWTYPASWPCQPHFLLKFRLQYRPAQHPAWSTVEPAGLEEVITDAVAGLPHAV
                    ***:*****  :******************** ************** mouseIL11RaD2-D3    RVSARDFLDAGTWSAWSPEAWGTPST  (SEQ ID NO:28)
humanIL11RaD2-D3    RVSARDFLDAGTWSTWSPEAWGTPST  (SEQ ID NO:20)
                    **************:***********
```

91.26% sequence identity

Figure 21B

Human gp130 (Genbank accession no. NP_002175.2):
MLTLQTWLVQALFIFLTTESTGELLDPCGYISPESPVVQLHSNFTAVCVLKEKCMDYFHVNANYIVWKTNHF
TIPKEQYTIINRTASSVTFTDIASLNIQLTCNILTFGQLEQNVYGITIISGLPPEKPKNLSCIVNEGKKMRCEWD
GGRETHLETNFTLKSEWATHKFADCKAKRDTPTSCTVDYSTVYFVNIEVWVEAENALGKVTSDHINFDPVY
KVKPNPPHNLSVINSEELSSILKLTWTNPSIKSVIILKYNIQYRTKDASTWSQIPPEDTASTRSSFTVQDLKPF
TEYVFRIRCMKEDGKGYWSDWSEEASGITYEDRPSKAPSFWYKIDPSHTQGYRTVQLVWKTLPPFEANGK
ILDYEVTLTRWKSHLQNYTVNATKLTVNLTNDRYLATLTVRNLVGKSDAAVLTIPACDFQATHPVMDLKAF
PKDNMLWVEWTTPRESVKKYILEWCVLSDKAPCITDWQQEDGTVHRTYLRGNLAESKCYLITVTPVYADG
PGSPESIKAYLKQAPPSKGPTVRTKKVGKNEAVLEWDQLPVDVQNGFIRNYTIFYRTIIGNETAVNVDSSHT
EYTLSSLTSDTLYMVRMAAYTDEGGKDGPEFTFTTPKFAQGEIEAIVVPVCLAFLLTTLLGVLFCFNKRDLIKK
HIWPNVPDPSKSHIAQWSPHTPPRHNFNSKDQMYSDGNFTDVSVVEIEANDKKPFPEDLKSLDLFKKEKINT
EGHSSGIGGSSCMSSSRPSISSSDENESSQNTSSTVQYSTVVHSGYRHQVPSVQVFSRSESTQPLLDSEER
PEDLQLVDHVDGGDGILPRQQYFKQNCSQHESSPDISHFERSKQVSSVNEEDFVRLKQQISDHISQSCGSG
QMKMFQEVSAADAFGPGTEGQVERFETVGMEAATDEGMPKSYLPQTVRQGGYMPQ (SEQ ID NO:17)

Signal peptide (residues 1-22); extracellular domain (residues 23-619); D1 (residues 26-112); D2 (residues 121-215); D3 (residues 222-321); transmembrane domain (residues 620-641); intracellular domain (residues 642-918).

Figure 29

Human IL-11Rα (Genbank accession no. NP_001136256.1; UniProt Q14626):
MSSSCSGLSRVLVAVATALVSASSPCPQAWGPPGVQYGQPGRSVKLCCPGVTAGDPVSWFRDGEPKLLQ
GPDSGLGHELVLAQADSTDEGTYICQTLDGALGGTVTLQLGYPPARPVVSCQAADYENFSCTWSPSQISG
LPTRYLTSYRKKTVLGADSQRRSPSTGPWPCPQDPLGAARCVVHGAEFWSQYRINVTEVNPLGASTRLLD
VSLQSILRPDPPQGLRVESVPGYPRRLRASWTYPASWPCQPHFLLKFRLQYRPAQHPAWSTVEPAGLEE
VITDAVAGLPHAVRVSARDFLDAGTWSTWSPEAWGTPSTGTIPKEIPAWGQLHTPPEVEPQVDSPAPPRP
SLQPHPRLLDHRDSVEQVAVLASLGILSFLGLVAGALALGLWLRLRRGGKDGSPKPGFLASVIPVDRRPGAP
NL (SEQ ID NO:18)

Signal peptide (residues 1-22); extracellular domain (residues 23-370); D1 (residues 27-110); D2 (residues 112-219); D3 (residues 220-317); transmembrane domain (residues 371-391); intracellular domain (residues 392-422).

Figure 30

DPCGYISPESPVVQLHSNFTAVCVLKEKCMDYFHVNANYIVWKTNHFTIPKEQYTIINRTASSVTFTDIASLNI
QLTCNILTFGQLEQNVYGITIISGLPPEKPKNLSCIVNEGKKMRCEWDGGRETHLETNFTLKSEWATHKFAD
CKAKRDTPTSCTVDYSTVYFVNIEVWVEAENALGKVTSDHINFDPVYKVKPNPPHNLSVINSEELSSILKLT
WTNPSIKSVIILKYNIQYRTKDASTWSQIPPEDTASTRSSFTVQDLKPFTEYVFRIRCMKEDGKGYWSDWSE
EASGIT (SEQ ID NO:19)

D1 (residues 26-112 of SEQ ID NO:17); D2 (residues 121-215 of SEQ ID NO:17); D3 (residues 222-321 of SEQ ID NO:17).

Figure 31

PPARPVVSCQAADYENFSCTWSPSQISGLPTRYLTSYRKKTVLGADSQRRSPSTGPWPCPQDPLGAARC
VVHGAEFWSQYRINVTEVNPLGASTRLLDVSLQSILRPDPPQGLRVESVPGYPRRLRASWTYPASWPCQP
HFLLKFRLQYRPAQHPAWSTVEPAGLEEVITDAVAGLPHAVRVSARDFLDAGTWSTWSPEAWGTPST
(SEQ ID NO:20)

D2 (residues 112-219 of SEQ ID NO:18); D3 (residues 220-317 of SEQ ID NO:18).

Figure 32

DECOY CYTOKINE RECEPTOR

RELATED APPLICATIONS

This Application is a national stage filing under 35 U.S.C. 371 of international application number PCT/EP2017/083032, filed Dec. 15, 2017, which claims the benefit of United Kingdom application number 1621431.4, filed Dec. 16, 2016, each of which is herein incorporated by reference in its entirety.

FIELD OF THE INVENTION

The present invention relates to decoy cytokine receptor molecules, specifically decoy IL-11 receptors capable of binding to interleukin 11 (IL-11).

BACKGROUND TO THE INVENTION

Many fatal and incurable diseases are caused by organ failure due to excessive and maladaptive fibrosis (Rockey et al., 2015 Journal of Infectious Diseases 214, jiw176). Fibrotic disorders include both rare, genetically-driven diseases such as scleroderma, idiopathic pulmonary fibrosis and hypertrophic cardiomyopathy, dilated cardiomyopathy (DCM), and common diseases like atrial fibrillation, ventricular fibrillation, non-alcoholic fatty liver disease and diabetic kidney disease. Due to the significant impact on world-wide morbidity and mortality, there is a need to develop therapeutics to inhibit the fibrotic response (Nanthakumar et al., 2015 Nat Rev Drug Discov 14, 693-720).

A major hallmark of fibrosis is the pathologic activation of resident fibroblasts that drives their transition from a quiescent state to proliferating, secretory and contractile myofibroblasts (Hinz et al., 2010 Am J Pathology 170, 1807-1816). Stimuli such as mechanical stress and pro-fibrotic cytokines can activate fibroblasts. The TGFβ1 pathway is considered to be of central importance for the fibrotic response (Leask and Abraham, 2004 The FASEB Journal 18, 816-827) and its inhibition is a therapeutic strategy that is under investigation (Gourdie et al., 2016 Nature Reviews Drug Discovery 15, 620-638). However, direct inhibition of multi-functional TGFβ1 is associated with severe side effects such as inflammation and cancer susceptibility.

SUMMARY OF THE INVENTION

In one aspect, the present invention provides an IL-11 binding receptor, optionally isolated, which is capable of binding to IL-11 and inhibiting IL-11 mediated signalling.

In some embodiments, the IL-11 binding receptor is capable of inhibiting interaction between IL-11 and gp130. In some embodiments, the IL-11 binding receptor is capable of inhibiting interaction between IL-11 and IL-11Rα.

In some embodiments, the IL-11 binding receptor comprises an amino acid sequence corresponding to the cytokine binding module of gp130. In some embodiments, the IL-11 binding receptor comprises an amino acid sequence corresponding to the cytokine binding module of IL-11Rα.

In some embodiments, the IL-11 binding receptor comprises an amino acid sequence having at least 70% sequence identity to the cytokine binding module (CBM) of gp130. In some embodiments, the IL-11 binding receptor comprises an amino acid sequence having at least 70% sequence identity to the cytokine binding module (CBM) of IL-11Rα.

In some embodiments, the IL-11 binding receptor comprises an amino acid sequence having at least 70% sequence identity to the sequence of SEQ ID NO:19. In some embodiments, the IL-11 binding receptor comprises an amino acid sequence having at least 70% sequence identity to the sequence of SEQ ID NO:20.

In some embodiments, the IL-11 binding receptor comprises:
(i) an amino acid sequence having at least 70% sequence identity to the sequence of SEQ ID NO:19; and
(ii) an amino acid sequence having at least 70% sequence identity to the sequence of SEQ ID NO:20.

In another aspect, the present invention provides an IL-11 binding receptor, optionally isolated, which is capable of binding to IL-11 and inhibiting IL-11 mediated signalling, comprising an amino acid sequence having at least 60% sequence identity to the sequence of SEQ ID NO:1 or 2.

In some embodiments in accordance with various aspects of the present invention, the IL-11 binding receptor is capable of inhibiting IL-11 trans signalling.

In another aspect, the present invention provides an IL-11 binding receptor, optionally isolated, which is capable of binding to IL-11, which is capable of inhibiting IL-11 trans signalling.

In some embodiments in accordance with various aspects of the present invention the IL-11 binding receptor is conjugated to a drug moiety or a detectable moiety.

In another aspect, the present invention provides a complex, optionally in vitro and/or optionally isolated, comprising an IL-11 binding receptor according to the present invention bound to IL-11.

In another aspect, the present invention provides a composition comprising an IL-11 binding receptor according to the present invention, and at least one pharmaceutically-acceptable carrier.

In another aspect, the present invention provides an isolated nucleic acid encoding an IL-11 binding receptor according to the present invention.

In another aspect, the present invention provides a vector comprising a nucleic acid according to the present invention.

In another aspect, the present invention provides a host cell comprising the vector according to the present invention.

In another aspect, the present invention provides a method for making an IL-11 binding receptor according to the present invention, comprising culturing the host cell according to the invention under conditions suitable for the expression of the IL-11 binding receptor, and recovering the IL-11 binding receptor.

In another aspect, the present invention provides an IL-11 binding receptor or composition according to the present invention for use in therapy, or in a method of medical treatment.

In another aspect, the present invention provides an IL-11 binding receptor or composition according to the present invention for use in the treatment or prevention of fibrosis, or a disease/disorder characterised by fibrosis.

In another aspect, the present invention provides an IL-11 binding receptor or composition according to the present invention for use in the treatment of a cancer.

In another aspect, the present invention provides the use of an IL-11 binding receptor or composition according to the present invention in the manufacture of a medicament for use in the treatment or prevention of fibrosis or a disease/disorder characterised by fibrosis.

In another aspect, the present invention provides the use of an IL-11 binding receptor or composition according to the present invention in the manufacture of a medicament for use in the treatment or prevention of a cancer.

In another aspect, the present invention provides a method of treating fibrosis comprising administering an IL-11 binding receptor or composition according to the present invention to a subject suffering from fibrosis or a disease/disorder characterised by fibrosis.

In another aspect, the present invention provides a method of treating cancer comprising administering an IL-11 binding receptor or composition according to the present invention to a subject suffering from a cancer.

In another aspect, the present invention provides an IL-11 binding receptor for use in a method of treating a disease in which IL-11 mediated signalling is implicated in the pathology of the disease, wherein the IL-11 binding receptor is capable of inhibiting IL-11 trans signalling.

In another aspect, the present invention provides the use of an IL-11 binding receptor in the manufacture of a medicament for use in the treatment of a disease in which IL-11 mediated signalling is implicated in the pathology of the disease, wherein the IL-11 binding receptor is capable of inhibiting IL-11 trans signalling.

In another aspect, the present invention provides a method of treating a disease in which IL-11 mediated signalling is implicated in the pathology of the disease, comprising administering an IL-11 binding receptor to a subject suffering from the disease, wherein the IL-11 binding receptor is capable of inhibiting IL-11 trans signalling.

In another aspect, the present invention provides a method comprising contacting a sample, optionally in vitro, containing, or suspected to contain, IL-11 with an IL-11 binding receptor according to the present invention and detecting the formation of a complex of the IL-11 binding receptor with IL-11.

In another aspect, the present invention provides a method of diagnosing a disease or condition in a subject, the method comprising contacting, in vitro, a sample from the subject with an IL-11 binding receptor according to the present invention and detecting the formation of a complex of the IL-11 binding receptor with IL-11.

In another aspect, the present invention provides a method of selecting or stratifying a subject for treatment with an IL-11-targeted agent, the method comprising contacting, in vitro, a sample from the subject with the IL-11 binding receptor according to the present invention and detecting the formation of a complex of the IL-11 binding receptor with IL-11.

In another aspect, the present invention provides the use of an IL-11 binding receptor according to the present invention for the detection of IL-11 in vitro or in vivo.

In another aspect, the present invention provides the use of an IL-11 binding receptor according to the present invention as an in vitro or in vivo diagnostic or prognostic agent.

DESCRIPTION

The present invention relates to recombinant receptor molecules with specificity for interleukin-11 (IL-11). The present disclosure describes the identification of IL-11/IL-11R signalling as a key mediator of fibrosis, and the generation and functional characterisation of recombinant IL-11 binding receptors. Therapeutic and diagnostic uses of the IL-11 binding receptors is also described.

IL-11 and IL-11 Mediated Signalling

The decoy IL-11 receptors of the present invention bind to interleukin 11. Interleukin 11 (IL-11), also known as adipogenesis inhibitory factor, is a pleiotropic cytokine and a member of the IL-6 family of cytokines that includes IL-6, IL-11, IL-27, IL-31, oncostatin M (OSM), leukemia inhibitory factor (LIF), cardiotrophin-1 (CT-1), cardiotrophin-like cytokine (CLC), ciliary neurotrophic factor (CNTF) and neuropoetin (NP-1).

IL-11 is transcribed with a canonical signal peptide that ensures efficient secretion from cells. The immature form of human IL-11 is a 199 amino acid polypeptide whereas the mature form of IL-11 encodes a protein of 178 amino acid residues (Garbers and Scheller., Biol. Chem. 2013; 394(9): 1145-1161). The human IL-11 amino acid sequence is available under UniProt accession no. P20809 (P20809.1 GI:124294). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. In some embodiments, the IL-11 is human IL-11, primate IL-11, non-human primate IL-11, rodent IL-11, murine IL-11, or mammalian IL-11. Similarly, in this specification "IL-11Rα" refers to an IL-11Ra from any species and includes isoforms, fragments, variants or homologues of an IL-11Rα from any species. In some embodiments, the IL-11Rα is human IL-11Rα, primate IL-11Rα, non-human primate IL-11Rα, rodent IL-11Rα, murine IL-11Rα, or mammalian IL-11Rα. Similarly, in this specification "gp130" refers to a gp130 from any species and includes isoforms, fragments, variants or homologues of gp130 from any species. In some embodiments, the gp130 is human gp130, primate gp130, non-human primate gp130, rodent gp130, murine gp130, or mammalian gp130.

IL-11 signals through a homodimer of the ubiquitously expressed β-receptor glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual IL-11 α-receptor (IL-11 Rα), which does not directly participate in signal transduction, although the initial cytokine binding event to the α-receptor leads to the final complex formation with the β-receptors. IL-11 activates a downstream signalling pathway, which is predominantly the mitogen-activated protein kinase (MAPK)-cascade and the Janus kinase/signal transducer and activator of transcription (Jak/STAT) pathway (Garbers and Scheller, supra).

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 (Genbank accession no. NP_002175.2) and domains thereof are shown in FIG. 29.

An alignment of the extracellular domain of human gp130 and murine gp130 (UniProt: IL6RB_MOUSE) is shown in FIG. 20A (73.45% sequence identity), and an alignment of D1-D3 of human gp130 with the corresponding region of murine gp130 is shown in FIG. 20B (71.43% sequence identity).

Human IL-11Rα is a 422 amino acid polypeptide (Gen bank accession no. NP_001136256.1 GI:218505839; UniProt Q14626) and shares ~85% nucleotide and amino acid sequence identity with the murine IL-11Rα (Du and Williams., Blood Vol, 89, No, 11, Jun. 1, 1997). Two isoforms of IL-11Rα have been reported, which differ in the cytoplasmic domain (Du and Williams, supra). In some embodiments as used herein, the IL-11Rα may be IL-11Rα isoform 1 or IL-11Rα isoform 2.

Human IL-11Rα (including the 22 amino acid signal peptide) is a 422 amino acid protein, and the mature form is 400 amino acids, comprising a 348 amino acid extracellular domain, a 20 amino acid transmembrane domain, and a 32 amino acid intracellular domain. The extracellular domain of the protein comprises an Ig-like domain D1 and two fibronectin-type III domains D2 and D3. The cytokine binding module (CBM) of IL-11Rα comprises domains D2 and D3; D1 has been shown to be dispensable for binding of IL-11Rα to IL-11 (Schleinkofer et al. 2001, J. Mal. Biol. 306, 263-274; Pflanz et al., 1999; FEBS Lett. 450, 117-122). The amino acid sequence of human IL-11Rα (Gen bank accession no. NP_001136256.1; UniProt Q14626) and domains thereof are shown in FIG. 30.

An alignment of the extracellular domains of human IL-11Rα and murine IL-11Rα (UniProt: I11RA_MOUSE) is shown in FIG. 21A (85.06% sequence identity), and an alignment of D2-D3 of human IL-11Rα with the corresponding region of murine IL-11Rα is shown in FIG. 21B (91.26% sequence identity).

The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain lacks the Box 1 and 2 regions that are required for activation of the JAK/STAT signalling pathway.

IL-11Rα binds its ligand with a low affinity (Kd~10 nmol/L) and alone is insufficient to transduce a biological signal. The generation of a high affinity receptor (Kd~400 to 800 pmol/L) capable of signal transduction requires co-expression of the IL-11Rα and gp130 (Curtis et al (Blood 1997 Dec. 1; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and MAPK and/or Jak/STAT signalling as described above.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11Rα) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R.

As used herein, 'IL-11/IL-11R signalling' refers to signalling mediated by IL-11 and/or IL-11Rα, fragments of IL-11 and/or IL-11Rα and polypeptide complexes comprising IL-11, IL-11Rα and/or fragments thereof. IL-11/IL-11R signalling involves binding of IL-11 and/or IL-11Rα to gp130, and consequent activation of signalling through gp130.

Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be a very important component of IL-11/IL-11R signalling, and may even be the most common form of IL-11/IL-11R signalling, because whilst the expression of IL-11Rα is restricted to a relatively small subset of cell types, gp130 is expressed on a wide range of cell types.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα.

In this specification an IL-11 receptor (IL-11R) refers to a polypeptide capable of binding IL-11 and inducing signal transduction in cells expressing gp130. An IL-11 receptor may be from any species and includes isoforms, fragments, variants or homologues of an IL-11 receptor from any species. In preferred embodiments the species is human (*Homo sapiens*). In some embodiments the IL-11 receptor may be IL-11Rα. Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

In some embodiments, the IL-11Rα may comprise, or consist of, the extracellular domain of IL-11Rα, which corresponds to amino acids 24 to 370 of the amino acid sequence of UniProt Q14626. In some embodiments, the IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of the extracellular domain of IL-11Rα from a given species.

In some embodiments, the IL-11 is mammalian IL-11 (e.g. cynornolgous, human and/or rodent (e.g. rat and/or murine) IL-11). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids IL-11 has been proposed to function mainly as a thrombopoietic growth factor, which underpinned the use of recombinant IL-11 (Neumega (Oprelvekin)) as a therapeutic agent to increase platelet count. TGFβ1 has been shown to induce IL-11 expression in fibroblasts (Elias et al., 1994 J. Immunol. 152, 2421-2429).

The role of IL-11/IL-11R signalling in fibrosis is not clear. The majority of studies suggest an anti-fibrotic function for IL-11/IL-11R signalling in the heart (Obana et al., 2010 Circulation 121, 684-691; Obana et al., 2012 Heart and Circulatory Physiology 303, H569-77) and kidney (Ham et al., 2013 Anesthesiology 119, 1389-1401; Stangou et al., 2011 J. Nephrol. 24, 106-111). Kurahara et al., J. Smooth Muscle Res. 2016; 52: 78-92 describes IL-11 as an anti-fibrotic cytokine, and suggests that IL-11/IL-11R signalling suppresses αSMA expression.

IL-11 has also been suggested to be an anti-inflammatory factor in several tissues and chronic inflammatory diseases (Trepicchio and Dorner, 1998 Expert Opin Investig Drugs 7, 1501-1504: Zhu et al., 2015 PLoS ONE 10, e0126296). These studies suggest that the observed secretion of IL-11 in response to TGFβ1 is a protective mechanism.

On the other hand, it has been suggested that IL-11/IL-11R signalling may be involved in pathology of diseases of the lung. Inhibition of IL-11/IL-11R signalling either via antibodies or a mutated recombinant IL-11 in a model of tuberculosis revealed a positive feedback loop in vivo and diminished histopathology of the lung (Kapina et al., 2011 PLoS ONE 6, e21878; Shepelkova et al., 2016 Journal of Infectious Diseases 214, jiw176), fibrosis of the murine airway has been associated with IL-11 expression (Tang et al., 1996 The Journal of Clinical Investigation 98, 2845-2853). When the pro-fibrotic function of IL-13 in lung tissue was investigated in IL-11RA –/– mice, IL-11/IL-11R signalling was implicated in the mechanism (Chen et al., 2005 J. Immunol. 174, 2305-2313).

IL-11 was also found to be elevated in the airway of patients with severe asthma (Minshall et al., 2000 Respiratory Research 14, 1-14), is overexpressed in the lungs of IPF patients (Lindahl et al., 2013 Respiratory Research 14, 1-14) and is elevated in skin lesions in atopic dermatitis patients (Toda et al., 2003 J Allergy Clin Immun 111, 875-881). It is uncertain whether these associations are due to increased IL-11 gene/protein expression as a response to disease processes, or whether IL-11 is an effector of disease processes.

IL-11 Binding Receptors

The present invention provides an IL-11 binding receptor. An IL-11 binding receptor is a peptide/polypeptide or plurality (e.g. non-covalent complex) thereof which is capable of binding to IL-11. By "receptor" we include fragments and derivatives thereof. As used herein, an IL-11 binding receptor is a peptide/polypeptide or plurality thereof capable of binding to IL-11 in the manner of a cytokine receptor binding to its ligand. IL-11 binding receptors according to the present invention may be provided in isolated form.

An IL-11 binding receptor is not an antibody or an antigen-binding fragment of an antibody which is specific for IL-11. An IL-11 binding receptor lacks sequences encoding heavy and light chain complementarity determining regions (CDRs) and/or heavy chain and light chain variable regions of an antibody or antigen binding fragment capable of specific binding to IL-11.

As used herein, a "peptide" is a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

IL-11 binding receptors according to the present invention bind to IL-11 (interleukin 11). They are soluble (not membrane bound) receptor molecules. In some embodiments, the IL-11 binding receptor binds to human IL-11. In some embodiments, the IL-11 binding receptor binds to non-human primate IL-11. In some embodiments, the IL-11 binding receptor binds to murine IL-11.

In some embodiments, the IL-11 binding receptors bind to IL-11-containing molecules/complexes (e.g. IL-11:IL-11Rα complex).

IL-11 binding receptors according to the present invention preferably bind and IL-11 and IL-11 containing complexes, and thereby make these species unavailable for binding to gp130, IL-11Rα and/or gp130:IL-11Rα receptors. As such, the present IL-11 binding receptors act as 'decoy' receptors for IL-11 and IL-11 containing complexes, much in the same way that etanercept acts as a decoy receptor for TNFα. IL-11 mediated signalling is reduced as compared to the level of signalling in the absence of the IL-11 binding receptors according to the invention.

The IL-11 binding receptors according to the present invention preferably bind to IL-11 through one or more cytokine binding modules (CBMs). The CBMs are, or are derived from or homologous to, the CBMs of naturally occurring receptor molecules for IL-11. For example, the IL-11 binding receptors of the present invention may comprise, or consist of, one or more CBMs which are from, are derived from or homologous to the CBM of gp130 and/or IL-11Rα.

As explained herein, IL-11 and complexes containing IL-11 (i.e. IL-11 in complex with IL-11Rα) are capable of activating IL-11 mediated signalling through binding to cell membrane bound gp130. The IL-11 binding receptors of the present invention are able to bind to the IL-11 and IL-11 containing species such as to inhibit the ability to interact with cell membrane bound gp130, and thereby inhibit IL-11 mediated signalling.

The IL-11 binding receptors of the present invention are not agonists of IL-11 mediated signalling. That is, the IL-11 binding receptors do not promote IL-11 mediated signalling. The IL-11 binding receptors do not bind to IL-11 to form IL-11 containing complexes capable of binding to cell membrane bound receptor for IL-11 to initiate IL-11 mediated signalling.

This is preferably achieved through binding of the IL-11 binding receptor to the region of IL-11 which is required for binding to cell membrane bound gp130. That is, IL-11 binding receptors capable of binding to IL-11 in the region bound by gp130 reduce the amount of IL-11 and IL-11 containing species available to bind to and activate signalling through cell membrane bound receptors for IL-11 (e.g. gp130 and IL-11Rα:gp130 receptor complexes).

Accordingly, in some embodiments, the IL-11 binding receptor is capable of binding to IL-11 in the region of IL-11 which is bound by gp130. In some embodiments, the IL-11 binding receptor is capable of binding to IL-11 in the same region of IL-11, or an overlapping region of IL-11, as the region of IL-11 which is bound by gp130. Ability to bind to IL-11 in the same region or an overlapping region of as the region bound by gp130 can be analysed using a competitive binding assay, such as a competition ELISA. In such assay, observation of a reduction/decrease in the level of interaction between IL-11 or IL-11:IL-11Rα and e.g. gp130, or IL-11Rα:gp130 in the presence of—or following incubation of one or both of the interaction partners with—the IL-11 binding receptor, as compared to the level of interaction in the absence of the IL-11 binding receptor indicates that the IL-11 binding receptor binds to the same region or overlapping region of IL-11 as the region bound by gp130. Whether an IL-11 binding receptor according to the present invention binds to IL-11 in the same or same region or overlapping region of IL-11 as the region bound by gp130 can also be determined by analysis of interaction using various methods well known in the art, including X-ray co-crystallography analysis of receptor-ligand complexes, peptide scanning, mutagenesis mapping, hydrogen-deuterium exchange analysis by mass spectrometry, phage display and proteolysis-based 'protection' methods. Such methods are described, for example, in Gershoni et al., BioDrugs, 2007, 21(3):145-156, which is hereby incorporated by reference in its entirety.

In some embodiments, the IL-11 binding receptor comprises, or consists of, an amino acid sequence corresponding to the cytokine binding module of gp130. Herein, "an amino acid sequence corresponding to the cytokine binding module of gp130" may be the amino acid sequence of the cytokine binding module of gp130, or an amino acid sequence which is capable of binding to IL-11 and having at least 60%, e.g. one of at least 65%, 70%, 75%, 80%, 85%, 90%, 91%, 92%, 93%, 94%, 95%, 96%, 97%, 98% or 99% sequence identity to the amino acid sequence of the cytokine binding module of gp130. The gp130 and IL-11 may be from any species, and includes isoforms, fragments, variants or homologues from any species.

In some embodiments, the IL-11 binding receptor comprises, or consists of, the cytokine binding module of gp130. In some embodiments, the IL-11 binding receptor comprises, or consists of, an amino acid sequence having at least 70% sequence identity to the cytokine binding module (CBM) of gp130.

The cytokine binding module of human gp130 corresponds to positions 26 to 321 of human gp130 (Genbank accession no. NP_002175.2) shown in SEQ ID NO:17, that is shown in FIG. 31.

The skilled person is well able to identify cytokine binding module for a given homologue of human gp130 by routine methods. For example, FIG. 20B shows an alignment of the cytokine binding module of human gp130 with the homologous mouse protein.

In some embodiments the IL-11 binding receptor comprises, or consists of, an amino acid sequence having at least 60%, 65%, 70%, 75%, 80%, 85%, 90%, 91%, 92%, 93%, 94%, 95%, 96%, 97%, 98% or 99% sequence identity to the cytokine binding module (CBM) of gp130. In some embodiments the IL-11 binding receptor comprises, or consists of, an amino acid sequence having greater than 70%, 75%, 80%, 85%, 90%, 91%, 92%, 93%, 94%, 95%, 96%, 97%, 98% or 99% sequence identity to the cytokine binding module (CBM) of gp130.

Sequence identity between amino acid sequences can be determined by methods known to the person skilled in the art. For example, to determine the percent identity of two amino acid sequences, the sequences to be compared can be aligned (e.g., gaps can be introduced in one or both of a first and a second amino acid sequence for optimal alignment), and the amino acids at corresponding positions can be compared. When a position in the first sequence is occupied by the same amino acid as the corresponding position in the second sequence, the sequences have "identity" at that position. The percent identity between two sequences is a function of the number of identical positions, taking into account the number of gaps, and the length of each gap, which need to be introduced for optimal alignment of the sequences. Sequence identity is preferably determined over the full length of the amino acid sequences being compared.

The IL-11 binding receptor according to the present invention may be capable of binding to IL-11 in the region of IL-11 bound by IL-11Rα.

In some embodiments, the IL-11 binding receptor is capable of binding to IL-11 in the same region of IL-11, or an overlapping region of IL-11, as the region of IL-11 which is bound by IL-11Rα. Ability to bind to IL-11 in the same region or an overlapping region of as the region bound by IL-11Rα can be analysed using a competitive binding assay, such as a competition ELISA. In such assay, observation of a reduction/decrease in the level of interaction between IL-11 and e.g. IL-11Rα or IL-11Rα:gp130 in the presence of—or following incubation of one or both of the interaction partners with—the IL-11 binding receptor, as compared to the level of interaction in the absence of the IL-11 binding receptor indicates that the IL-11 binding receptor binds to the same region or overlapping region of IL-11 as the region bound by IL-11Rα. Whether an IL-11 binding receptor according to the present invention binds to IL-11 in the same or same region or overlapping region of IL-11 as the region bound by IL-11Rα can also be determined e.g. by X-ray co-crystallography analysis of receptor-ligand complexes, peptide scanning, mutagenesis mapping, hydrogen-deuterium exchange analysis by mass spectrometry, phage display and proteolysis-based 'protection' methods (described, for example, in Gershoni et al., BioDrugs, 2007, 21(3):145-156, incorporated by reference hereinabove).

In some embodiments, the IL-11 binding receptor comprises an amino acid sequence corresponding to the cytokine binding module of IL-11Rα. Herein, "an amino acid sequence corresponding to the cytokine binding module of IL-11Rα" may be the amino acid sequence of the cytokine binding module of IL-11Rα, or an amino acid sequence which is capable of binding to IL-11 and having at least 60%, e.g. one of at least 65%, 70%, 75%, 80%, 85%, 90%, 91%, 92%, 93%, 94%, 95%, 96%, 97%, 98% or 99% sequence identity to the amino acid sequence of the cytokine binding module of IL-11Rα. The IL-11Rα and IL-11 may be from any species, and includes isoforms, fragments, variants or homologues from any species.

In some embodiments, the IL-11 binding receptor comprises the cytokine binding module of IL-11Rα. In some embodiments, the IL-11 binding receptor comprises an amino acid sequence having at least 70% sequence identity to the cytokine binding module (CBM) of IL-11Rα.

The cytokine binding module of human IL-11Rα corresponds to positions 112 to 317 of human IL-11Rα (Genbank accession no. NP_001136256.1; UniProt Q14626) shown in SEQ ID NO:18, that is: FIG. 32.

The skilled person is well able to identify cytokine binding module for a given homologue of human IL-11Rα by routine methods. For example, FIG. 21B shows an alignment of the cytokine binding module of human IL-11Rα with the homologous mouse protein.

In some embodiments the IL-11 binding receptor comprises an amino acid sequence having at least 60%, 65%, 70%, 75%, 80%, 85%, 90%, 91%, 92%, 93%, 94%, 95%, 96%, 97%, 98% or 99% sequence identity to the cytokine binding module (CBM) of IL-11Rα. In some embodiments the IL-11 binding receptor comprises an amino acid sequence having greater than 70%, 75%, 80%, 85%, 90%, 91%, 92%, 93%, 94%, 95%, 96%, 97%, 98% or 99% sequence identity to the cytokine binding module (CBM) of IL-11Rα.

The IL-11 binding receptor according to the present invention may be capable of binding to IL-11 in the region of IL-11 bound by gp130, and may also be capable of binding to IL-11 in the region of IL-11 bound by IL-11Rα.

IL-11 binding receptor molecules capable of such binding interact with IL-11 with high affinity, to form stable complexes. IL-11 binding receptors capable of binding to IL-11 in the regions bound by both gp130 and IL-11Rα reduce the amount of IL-11 and IL-11 containing species available to bind to and activate signalling through cell membrane bound receptors for IL-11 (e.g. gp130 and IL-11Rα:gp130 receptor complexes).

In some embodiments, the IL-11 binding receptor is capable of binding to IL-11 in the same region of IL-11, or an overlapping region of IL-11, as the region of IL-11 which is bound by gp130; and is capable of binding to IL-11 in the same region of IL-11, or an overlapping region of IL-11, as the region of IL-11 which is bound by IL-11Rα.

In some embodiments, the IL-11 binding receptor comprises, or consists of, an amino acid sequence corresponding to the cytokine binding module of gp130 and an amino acid sequence corresponding to the cytokine binding module of IL-11Rα.

In some embodiments, the IL-11 binding receptor comprises, or consists of, the cytokine binding module of gp130 and the cytokine binding module of IL-11Rα. In some embodiments, the IL-11 binding receptor comprises, or consists of, an amino acid sequence having at least 70% sequence identity to the cytokine binding module (CBM) of gp130 and an amino acid sequence having at least 70% sequence identity to the cytokine binding module (CBM) of IL-11Rα.

In some embodiments the IL-11 binding receptor comprises or consists of: an amino acid sequence having at least 60%, 65%, 70%, 75%, 80%, 85%, 90%, 91%, 92%, 93%, 94%, 95%, 96%, 97%, 98% or 99% sequence identity to the cytokine binding module (CBM) of gp130; and an amino acid sequence having at least 60%, 65%, 70%, 75%, 80%, 85%, 90%, 91%, 92%, 93%, 94%, 95%, 96%, 97%, 98% or 99% sequence identity to the cytokine binding module (CBM) of IL-11Rα. In some embodiments the IL-11 binding receptor comprises or consists of: an amino acid sequence having greater than 70%, 75%, 80%, 85%, 90%, 91%, 92%, 93%, 94%, 95%, 96%, 97%, 98% or 99% sequence identity to the cytokine binding module (CBM) of gp130; and an amino acid sequence having greater than 70%, 75%, 80%, 85%, 90%, 91%, 92%, 93%, 94%, 95%, 96%, 97%, 98% or 99% sequence identity to the cytokine binding module (CBM) of IL-11Rα.

In some embodiments, the IL-11 binding receptor comprises, or consists of, an amino acid sequence having at least 70% sequence identity to a cytokine binding module of a decoy IL-11 receptor as described herein, e.g. decoy IL-11 receptor 1 (D11R1) or decoy IL-11 receptor 2 (D11R2). The amino acid sequences for D11R1 and D11R2 are shown in FIGS. 17A and 17B, respectively.

In some embodiments, the cytokine binding module (CBM) of gp130 comprises or consists of an amino acid sequence as shown in SEQ ID NO:19 or SEQ ID NO:4.

In some embodiments the IL-11 binding receptor comprises, or consists of, an amino acid sequence having at least 60%, 65%, 70%, 75%, 80%, 85%, 90%, 91%, 92%, 93%, 94%, 95%, 96%, 97%, 98% or 99% sequence identity to SEQ ID NO:19 or 4. In some embodiments the IL-11 binding receptor comprises, or consists of, an amino acid sequence having greater than 70%, 75%, 80%, 85%, 90%, 91%, 92%, 93%, 94%, 95%, 96%, 97%, 98% or 99% sequence identity to SEQ ID NO:19 or 4.

In some embodiments, the cytokine binding module (CBM) of IL-11Rα comprises or consists of an amino acid sequence as shown in SEQ ID NO:20 or SEQ ID NO:6.

In some embodiments the IL-11 binding receptor comprises an amino acid sequence having at least 60%, 65%, 70%, 75%, 80%, 85%, 90%, 91%, 92%, 93%, 94%, 95%, 96%, 97%, 98% or 99% sequence identity to SEQ ID NO:20 or 6. In some embodiments the IL-11 binding receptor comprises an amino acid sequence having greater than 70%, 75%, 80%, 85%, 90%, 91%, 92%, 93%, 94%, 95%, 96%, 97%, 98% or 99% sequence identity to SEQ ID NO:20 or 6.

In some embodiments the IL-11 binding receptor comprises, or consists of, an amino acid sequence having at least 60%, 65%, 70%, 75%, 80%, 85%, 90%, 91%, 92%, 93%, 94%, 95%, 96%, 97%, 98% or 99% sequence identity to SEQ ID NO:19 or 4 and an amino acid sequence having at least 60%, 65%, 70%, 75%, 80%, 85%, 90%, 91%, 92%, 93%, 94%, 95%, 96%, 97%, 98% or 99% sequence identity to SEQ ID NO:20 or 6. In some embodiments the IL-11 binding receptor comprises, or consists of, an amino acid sequence having greater than 70%, 75%, 80%, 85%, 90%, 91%, 92%, 93%, 94%, 95%, 96%, 97%, 98% or 99% sequence identity to SEQ ID NO:19 or 4 and an amino acid sequence having greater than 70%, 75%, 80%, 85%, 90%, 91%, 92%, 93%, 94%, 95%, 96%, 97%, 98% or 99% sequence identity to SEQ ID NO:20 or 6.

In some embodiments, the IL-11 binding receptor comprises or consists essentially of:

(i) a region corresponding to the cytokine binding module of gp130; and (ii) a region corresponding to the cytokine binding module of IL-11Rα.

In some embodiments, the IL-11 binding receptor is a polypeptide comprising or consisting essentially of a region corresponding to the cytokine binding module of gp130, and a region corresponding to the cytokine binding module of IL-11Rα.

The IL-11 binding receptor may be a single polypeptide or fusion protein comprising, or consisting of, a region corresponding to the cytokine binding module of gp130 (as described herein), optionally a linker, and a region corresponding to the cytokine binding module of IL-11Rα (as described herein).

In some embodiments, the IL-11 binding receptor comprises an amino acid sequence having at least 70% sequence identity to the cytokine binding module (CBM) of gp130 and an amino acid sequence having at least 70% sequence identity to the cytokine binding module (CBM) of IL-11Rα in a single polypeptide.

In some embodiments the IL-11 binding receptor comprises, or consists of:
(i) an amino acid sequence having at least 60%, 65%, 70%, 75%, 80%, 85%, 90%, 91%, 92%, 93%, 94%, 95%, 96%, 97%, 98% or 99% sequence identity to SEQ ID NO:19 or 4, or the cytokine binding module (CBM) of gp130; and
(ii) an amino acid sequence having at least 60%, 65%, 70%, 75%, 80%, 85%, 90%, 91%, 92%, 93%, 94%, 95%, 96%, 97%, 98% or 99% sequence identity to SEQ ID NO:20 or 6, or the cytokine binding module (CBM) of IL-11Rα.

In some embodiments the IL-11 binding receptor comprises, or consists of:
(i) In some embodiments the IL-11 binding receptor comprises an amino acid sequence having greater than 70%, 75%, 80%, 85%, 90%, 91%, 92%, 93%, 94%, 95%, 96%, 97%, 98% or 99% sequence identity to SEQ ID NO:19 or 4, or the cytokine binding module (CBM) of gp130; and
(ii) an amino acid sequence having greater than 70%, 75%, 80%, 85%, 90%, 91%, 92%, 93%, 94%, 95%, 96%, 97%, 98% or 99% sequence identity to SEQ ID NO:20 or 6, or the cytokine binding module (CBM) of IL-11Rα.

In some embodiments, the IL-11 binding receptor comprises a linker between the IL-11 binding sequences. The linker may comprise or consist of an amino acid sequence, and may be covalently bonded (e.g. by peptide bonds) to ends of the sequences according to (i) and (ii). As such, the IL-11 binding receptor may comprise, or consist of, a contiguous amino acid sequence having an amino acid sequence encoding the cytokine binding module of gp130, an amino acid sequence encoding a linker and an amino acid sequence encoding the cytokine binding module of IL-11Rα, where the amino acid sequence encoding the linker is positioned between the amino acid sequences encoding the respective cytokine binding domains.

The linker may be a peptide or polypeptide linker. The linker may be a flexible linker. Amino acid sequences of flexible linkers are known to the skilled person, and are described, for example in Chen et al., Adv Drug Deliv Rev (2013) 65(10): 1357-1369, which is hereby incorporated by reference in its entirety. In some embodiments the flexible linker sequence comprises serine and glycine residues.

The linker may be any length and form as long as it does not substantially constrain the amino acid sequences of (i) and/or (ii) so as to inhibit their ability to interact with IL-11. In some embodiments the linker is a peptide/polypeptide consisting of an amino acid sequence of 1-500, 1-400, 1-300, 1-200, 1-100, 5-75, or 10-60 amino acid residues.

In some embodiments, the linker sequence of IL-11 binding receptor according to the present invention comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:5 or 8.

In some embodiments, the IL-11 binding receptor according to the present invention comprises a leader sequence (also known as a signal peptide or signal sequence). Leader sequences normally consist of a sequence of 5-30 hydrophobic amino acids, which form a single alpha helix. Secreted proteins and proteins expressed at the cell surface often comprise leader sequences. The leader sequence may be present at the N-terminus of the IL-11 binding receptor, and may be present in the newly synthesized receptor. The leader sequence provides for efficient intracellular trafficking and secretion of the IL-11 binding receptor. Leader sequences are often removed by cleavage, and thus are not comprised in the mature IL-11 binding receptor.

Leader sequences are known for many proteins, and are recorded in databases such as GenBank, UniProt, Swiss-Prot, TrEMBL, Protein Information Resource, Protein Data Bank, Ensembl, and InterPro. and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

In some embodiments, the leader sequence of the IL-11 binding receptor of the present invention comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:3.

In some embodiments, the IL-11 binding receptor according to the present invention may be provided with a relative arrangement of amino acid sequences encoding a gp130 cytokine binding module, an IL-11Rα cytokine binding module and a linker according to one of the following:

N term-[signal sequence]-[gp130 CBM][linker]-[IL-11Rα CBM]-C term;
N term-[gp130 CBM]-[linker]-[IL-11Rα]-C term;
N term-[signal sequence][IL-11Rα CBM]-[linker]-[gp130 CBM]-C term; or
N term[IL-11Rα CBM]-[linker]-[gp130 CBM]-C term.

In some embodiments, the IL-11 binding receptor according to the present invention may comprise a linker having an amino acid sequence comprising or consisting of the amino acid sequence of SEQ ID NO:5 or 8.

IL-11 binding receptors according to the present invention are distinct from naturally-occurring IL-11 binding molecules, e.g. a naturally occurring receptor for IL-11 or IL-11 containing complex (e.g. IL-11:IL-11Rα).

For example, in some embodiments, the IL-11 binding receptor comprises amino acid sequence corresponding only to the cytokine binding module of gp130, and not other regions of gp130. The IL-11 binding receptor of the present invention preferably lacks amino acid sequence corresponding to regions of gp130 other than the cytokine binding module of gp130 (i.e. D1 to D3). In some embodiments, the IL-11 binding receptor lacks amino acid sequence corresponding to the intracellular domain of gp130 and/or the transmembrane domain of gp130. In some embodiments the IL-11 binding receptor lacks amino acid sequence corresponding to the stalk region of gp130.

In some embodiments, the IL-11 binding receptor of the present invention preferably lacks amino acid sequence corresponding to regions of gp130 other than positions 23 to 321 of SEQ ID NO:17. In some embodiments the IL-11 binding receptor lacks amino acid sequence corresponding to positions 322 to 619 of SEQ ID NO:17.

Herein, an amino acid sequence which 'corresponds' to a reference region or sequence of a given peptide/polypeptide has at least 60%, e.g. one of at least 65%, 70%, 75%, 80%, 85%, 90%, 91%, 92%, 93%, 94%, 95%, 96%, 97%, 98% or 99% sequence identity to the amino acid sequence of the reference region/sequence.

Similarly, in some embodiments, the IL-11 binding receptor comprises amino acid sequence corresponding only to the cytokine binding module of IL-11Rα, and not other regions of IL-11Rα. That is, the IL-11 binding receptor of the present invention preferably lacks amino acid sequence corresponding to regions of IL-11Rα other than the cytokine binding module of IL-11Rα (i.e. D2 to D3). In some embodiments, the IL-11 binding receptor lacks amino acid sequence corresponding to the intracellular domain of IL-11Rα and/or the transmembrane domain of IL-11Rα. In some embodiments the IL-11 binding receptor lacks amino acid sequence corresponding to the stalk region of IL-11Rα. In some embodiments the IL-11 binding receptor lacks amino acid sequence corresponding to D1 of IL-11Rα.

In some embodiments, the IL-11 binding receptor of the present invention preferably lacks amino acid sequence corresponding to regions of IL-11Rα other than positions 112 to 317 of SEQ ID NO:18. In some embodiments the IL-11 binding receptor lacks amino acid sequence corresponding to positions 27 to 110 of SEQ ID NO:18.

In some embodiments, the IL-11 binding receptor may comprise further functional amino acid sequences. For example, the IL-11 binding receptor may comprise amino acid sequence(s) to facilitate expression, folding, trafficking, processing, purification or detection of the IL-11 binding receptor. For example, the IL-11 binding receptor may comprise a sequence encoding a protein tag, e.g. a FLAG, His, (e.g. 6×His), Myc, GST, MBP, HA, E, or Biotin tag, optionally at the N- or C-terminus.

In some embodiments, the IL-11 binding receptor of the present invention comprises, or consists of, an amino acid sequence having at least 60%, 65%, 70%, 75%, 80%, 85% 86%, 87%, 88%, 89%, 90%, 91%, 92%, 93%, 94%, 95%, 96%, 97%, 98%, 99%, or 100% sequence identity to the amino acid sequence of SEQ ID NO:1 or 2.

IL-11 binding receptors according to the present invention may comprise or consist of an amino acid sequence that has a high percentage sequence identity to one or more of the nucleic acid sequences described herein, or nucleic acid sequence encoding the same amino acid sequence as a result of codon degeneracy. For example, IL-11 binding receptors according to the present invention include IL-11 binding receptors encoded by a nucleic acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the IL-11 binding receptor encoded by the nucleic acid sequence of SEQ ID NO:9 or 10, or nucleic acid sequence encoding the same amino acid sequence as SEQ ID NO:9 or 10 as a result of codon degeneracy.

IL-11 binding receptors according to the present invention may be detectably labelled or, at least, capable of detection. For example, the IL-11 binding receptor may be labelled with a radioactive atom or a coloured molecule or a fluorescent molecule or a molecule which can be readily detected in any other way. Suitable detectable molecules include fluorescent proteins, luciferase, enzyme substrates, radiolabels and binding moieties. Labelling may be by conjugation to the IL-11 binding receptor. The IL-11 binding receptor may be directly labelled with a detectable label or it may be indirectly labelled. In some embodiments, the label may be selected from: a radio-nucleotide, positron-emitting radionuclide (e.g. for positron emission tomography (PET)), MRI contrast agent or fluorescent label.

IL-11 binding receptors according to the present invention may be conjugated to a drug moiety, e.g. a cytotoxic small molecule. Such conjugates are useful for the targeted killing of cells expressing the antigen molecule.

Functional Properties of the IL-11 Binding Receptors

The IL-11 binding receptors of the present invention may be characterised by reference to certain functional properties. In particular, an IL-11 binding receptor according to the present invention may possess one or more of the following properties:

a) Specific binding to IL-11 (e.g. human IL-11 and/or mouse IL-11);
b) Inhibition of interaction between IL-11 and IL-11Rα;
c) Inhibition of interaction between IL-11 and gp130;
d) Inhibition of interaction between IL-11 and IL-11Rα: gp130 receptor complex;
e) Inhibition of interaction between IL-11:IL-11Rα complex and gp130;
f) Inhibition of signalling mediated by IL-11;
g) Inhibition of signalling mediated by binding of IL-11 to IL-11Rα:gp130 receptor complex;
h) Inhibition of signalling mediated by binding of IL-11: IL-11Rα complex to gp130 (i.e. IL-11 trans signalling);
i) Inhibition of fibroblast proliferation;
j) Inhibition of myofibroblast generation from fibroblasts;
k) Inhibition of a pathological process mediated by IL-11;
l) Inhibition of fibrosis;
m) Inhibition of gene or protein expression in fibroblasts of one or more of collagen, fibronectin, periostin, IL-6, IL-11, αSMA, TIMP1, MMP2, e.g. following stimulation with a profibrotic factor;
n) Inhibition of extracellular matrix production by fibroblasts
o) Inhibition of proliferation and/or survival of cells of a cancer;
p) Inhibition of tumour growth.

An IL-11 binding receptor which is capable of binding to IL-11 preferably binds IL-11 with greater affinity, and/or with greater duration than it binds to proteins other than IL-11.

In some embodiments the present IL-11 binding receptors may bind with greater affinity to IL-11 than to one or more other members of the IL-6 cytokine family. In some embodiments, the present IL-11 binding receptors may bind with greater affinity to IL-11 than to one or more of IL-6, leukemia inhibitory factor (LIF), oncostatin M (OSM), cardiotrophin-1 (CT-1), ciliary neurotrophic factor (CNTF), and cardiotrophin-like cytokine (CLC).

In some embodiments, the extent of binding to a protein other than IL-11 is less than about 10% of the binding of the IL-11 binding receptor to IL-11 as measured, e.g., by ELISA, SPR, Bio-Layer Interferometry (BLI), MicroScale Thermophoresis (MST), or by a radioimmunoassay (RIA). Alternatively, the binding specificity for IL-11 may be reflected in terms of binding affinity, where the IL-11 binding receptor of the present invention binds to IL-11 with a KD that is at least 0.1 order of magnitude (i.e. $0.1 \times 10n$, where n is an integer representing the order of magnitude) greater than the KD towards another, non-target molecule. This may optionally be one of at least 0.2, 0.3, 0.4, 0.5, 0.6, 0.7, 0.8, 0.9, 1.0, 1.5, or 2.0.

Binding affinity may be expressed in terms of dissociation constant (KD). Binding affinity can be measured by methods known in the art, such as by ELISA (for example, as described in Antibody Engineering, vol. 1 (2nd Edn), Springer Protocols, Springer (2010), Part V, pp 657-665.), Surface Plasmen Resonance (SPR; see e.g. Hearty et al., Methods Mol Biol (2012) 907:411-442; or Rich et al., Anal Biochem. 2008 Feb. 1; 373(1):112-20), Bio-Layer Interferometry (see e.g. Lad et al., (2015) J Biomol Screen 20(4): 498-507; or Concepcion et al., Comb Chem High Throughput Screen. 2009 September; 12(8):791-800), MicroScale Thermophoresis (MST) analysis (see e.g. Jerabek-Willemsen et al., Assay Drug Dev Technol. 2011 August; 9(4): 342-353), or by a radiolabelled antigen binding assay (RIA).

In some embodiments, the IL-11 binding receptor according to the present invention binds to IL-11 with a KD of 5 µM or less, preferably one of ≤1 µM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM.

In some embodiments, the IL-11 binding receptor according to the present invention binds to IL-11 with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml.

The IL-11 binding receptors according to the present invention inhibit IL-11 mediated signalling. Herein, 'inhibition' refers to a reduction, decrease or lessening relative to a control condition. For example, inhibition of a process by an IL-11 binding receptor refers to a reduction, decrease or lessening of the extent/degree of that process in the absence of the IL-11 binding receptor, and/or in the presence of an appropriate control receptor.

The skilled person is able to identify an appropriate control condition for a given assay. For example, a control receptor may be a receptor directed against a target protein which is known not to have a role involved in the property being investigated in the assay.

Inhibition may herein also be referred to as neutralisation or antagonism. That is, an IL-11 binding receptor which is capable of inhibiting a function or process (e.g. interaction, signalling or other activity mediated by IL-11 or an IL-11-containing complex) may be said to be a 'neutralising' or 'antagonist' IL-11 binding receptor with respect to the relevant function or process. For example, IL-11 binding receptor which is capable of inhibiting IL-11 mediated signalling may be referred to as an IL-11 binding receptor which is capable of neutralising IL-11 mediated signalling, or may be referred to as an antagonist of IL-11 mediated signalling.

IL-11 binding receptors according to the present invention preferably compete for binding to IL-11 with one or more naturally occurring receptors for IL-11, e.g. gp130, IL-11Rα, or a variant/isoform/homologue or IL-11 binding fragment of gp130 or IL-11Rα. In some embodiments, an IL-11 binding receptor according to the present invention is a competitive inhibitor of binding of one of more of gp130, IL-11Rα, and variants/isoforms/homologues and IL-11 binding fragments of gp130 and/or IL-11Rα. That is, in some embodiments, the IL-11 binding receptor is capable of inhibiting interaction between IL-11 and one or more naturally occurring receptors for IL-11.

As used herein, a 'naturally occurring receptor' is a receptor which is found in nature. A naturally occurring receptor and/or the constituent peptides/polypeptides thereof may the product of transcription, mRNA processing (e.g. splicing), translation, and post-translational processing (e.g. proteolytic cleavage, glycosylation) from endogenous nucleic acid of a given host species.

In some embodiments, the IL-11 binding receptor according to the present invention binds to IL-11 in the region bound by one or more naturally occurring receptors for IL-11. In some embodiments, the IL-11 binding receptor binds to the same region, or overlapping region, of IL-11 as the region bound by one or more naturally occurring receptors for IL-11.

The ability of an IL-11 binding receptor to compete with a naturally occurring receptor for IL-11 (e.g. gp130, IL-11Rα, or variants/isoforms/homologues or IL-11 binding fragments of gp130 or IL-11Rα) for binding to IL-11 (i.e. inhibit interaction between IL-11 and the naturally occurring receptor), can be determined for example by analysis of interaction between IL-11 and the naturally occurring receptor in the presence of, or following incubation of IL-11, or IL-11 and the naturally occurring receptor, with the IL-11 binding receptor.

An example of a suitable assay to determine whether a given IL-11 binding receptor competes with gp130, IL-11Rα, or a variant/isoform/homologue or IL-11 binding fragment of gp130 or IL-11Rα for binding to IL-11 is a competitive binding assay, such as a competition ELISA assay.

An IL-11 binding receptor which is capable of inhibiting a given interaction (e.g. between IL-11 and gp130, or between IL-11 and IL-11Rα, or between IL-11 and IL-11Rα:gp130, or between IL-11:IL-11Rα and gp130) is identified by the observation of a reduction/decrease in the level of interaction between the interaction partners in the presence of—or following incubation of one or both of the interaction partners with—the IL-11 binding receptor, as compared to the level of interaction in the absence of the IL-11 binding receptor (or in the presence of an appropriate control receptor). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the IL-11 binding receptor may be labelled or used in conjunction with a detectable entity for the purposes of detecting and/or measuring the level of interaction.

In some embodiments, the IL-11 binding receptor according to the present invention inhibits interaction between human IL-11 and human gp130. In some embodiments, the IL-11 binding receptor inhibits interaction between human IL-11 in complex with human IL-11Rα (i.e. human IL-11: IL-11Rα) and human gp130. In some embodiments, the IL-11 binding receptor inhibits interaction between human IL-11 and human gp130:IL-11Rα receptor complex. In some embodiments, the IL-11 binding receptor inhibits interaction between human IL-11:IL-11Rα and human gp130:IL-11Rα receptor complex.

Such assays are also useful to determine whether an IL-11 binding receptor binds to the same region or overlapping region of IL-11 as the region bound by one or more naturally occurring receptors for IL-11. That is, observation of a reduction/decrease in the level of interaction between IL-11 or IL-11:IL-11Rα and e.g. gp130, IL-11Rα, or IL-11Rα: gp130 in the presence of—or following incubation of one or both of the interaction partners with—the IL-11 binding receptor, as compared to the level of interaction in the absence of the IL-11 binding receptor suggests that IL-11 binding receptor binds to the same region or overlapping region of IL-11 as the region bound by one or more naturally occurring receptors for IL-11.

Whether an IL-11 binding receptor according to the present invention binds to IL-11 in the same or same region or overlapping region of IL-11 as the region bound by a naturally occurring receptor for IL-11 can also be determined by analysis of interaction using various methods well known in the art, including X-ray co-crystallography analysis of receptor-ligand complexes, peptide scanning, mutagenesis mapping, hydrogen-deuterium exchange analysis by mass spectrometry, phage display and proteolysis-based 'protection' methods. Such methods are described, for example, in Gershoni et al., BioDrugs, 2007, 21(3):145-156, incorporated by reference hereinabove. The region of IL-11 bound by naturally occurring receptors for IL-11 can also be determined by reference e.g. to Griffin et al. 2013, Cytokine 63(3) 267 and/or Putoczki et al., 2014, Acta Crystallogr D Biol Crystallogr 70(Pt 9):2277-85.

Ability of an IL-11 binding receptor to inhibit interaction between two interaction partners can also be determined by analysis of the downstream functional consequences of the interaction, e.g. receptor signalling. For example, downstream functional consequences of interaction between IL-11 and IL-11Rα:gp130 or between IL-11:IL-11Rα and gp130 may include proliferation of fibroblasts, myofibroblast generation from fibroblasts, or gene or protein expression of one or more of collagen, fibronectin, periostin, IL-6, IL-11, αSMA, TIMP1, MMP2.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the IL-11 binding receptor, the fibroblasts may be cardiac fibroblasts (e.g. atrial fibroblasts), skin fibroblasts, lung fibroblasts, kidney fibroblasts or liver fibroblasts. Fibroblasts may be characterised by gene or protein expression of one or more of COL1A, ACTA2, prolyl-4-hydroxylase, MAS516, and FSP1.

Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

In some embodiments, the IL-11 binding receptor according to the present invention may inhibit protein expression of one or more markers of fibrosis, e.g. protein expression of one or more of collagen, fibronectin, periostin, IL-6, IL-11, αSMA, TIMP1, MMP2.

The ability of an IL-11 binding receptor to inhibit interaction between IL-11 and IL-11Rα:gp130 can, for example, be analysed by stimulating fibroblasts with TGFβ1, incubating the cells in the presence of the IL-11 binding receptor and analysing the proportion of cells having αSMA-positive phenotype after a defined period of time. In such example, inhibition of interaction between IL-11 and IL-11Rα:gp130 can be identified by observation of a lower proportion of cells having an αSMA-positive phenotype as compared to positive control condition in which cells are treated with TGFβ1 in the absence of the IL-11 binding receptor (or in the presence of an appropriate control receptor), or in the presence of an appropriate control receptor.

Such assays are also suitable for analysing the ability of the IL-11 binding receptor to inhibit IL-11-mediated signalling.

In some embodiments, the IL-11 binding receptor according to the present invention is capable of inhibiting interaction between IL-11 and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the IL-11 binding receptor (or in the presence of an appropriate control receptor). In some embodiments, the IL-11 binding receptor according to the present invention is capable of inhibiting interaction between IL-11 and gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the IL-11 binding receptor (or in the presence of an appropriate control receptor).

In some embodiments, the IL-11 binding receptor according to the present invention is capable of inhibiting interaction between IL-11 and IL-11Rα to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the IL-11 binding receptor (or in the presence of an appropriate control receptor). In some embodiments, the IL-11 binding receptor according to the present invention is capable of inhibiting interaction between IL-11 and IL-11Rα to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα in the absence of the IL-11 binding receptor (or in the presence of an appropriate control receptor).

In some embodiments, the IL-11 binding receptor according to the present invention is capable of inhibiting interaction between IL-11 and IL-11Rα:gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the IL-11 binding receptor (or in the presence of an appropriate control receptor). In some embodiments, the IL-11 binding receptor according to the present invention is capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα:gp130 in the absence of the IL-11 binding receptor (or in the presence of an appropriate control receptor).

In some embodiments, the IL-11 binding receptor according to the present invention is capable of inhibiting interaction between IL-11:IL-11Rα complex and gp130 to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the IL-11 binding receptor (or in the presence of an appropriate control receptor). In some embodiments, the IL-11 binding receptor is capable of inhibiting interaction between IL-11:IL-11Rα complex and gp130 to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the IL-11 binding receptor (or in the presence of an appropriate control receptor).

Inhibition of IL-11 mediated signalling can be analysed using $^3$H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

As used herein, 'IL-11 mediated signalling' and/or processes mediated by IL-11 includes signalling mediated by fragments of IL-11 and polypeptide complexes comprising IL-11 or fragments thereof. IL-11 mediated signalling may be signalling mediated by human IL-11 and/or mouse IL-11. Signalling mediated by IL-11 may occur following binding of IL-11 or an IL-11 containing complex to a receptor to which IL-11 or said complex binds.

In some embodiments, IL-11 binding receptors according to the present invention are capable of inhibiting the biological activity of IL-11 or an IL-11-containing complex. In some embodiments, the IL-11 binding receptor binds to IL-11 or the IL-11-containing complex in a region which is important for binding to a receptor for the IL-11 or IL-11-containing complex, e.g. gp130 or IL-11Rα, and thereby disrupts binding to and/or signalling through the receptor.

In some embodiments, the IL-11 binding receptor according to the present invention is an antagonist of one or more signalling pathways which are activated by signal transduction through receptors comprising IL-11Rα and/or gp130, e.g. IL-11Rα:gp130. In some embodiments, the IL-11 binding receptor is capable of inhibiting signalling through one or more immune receptor complexes comprising IL-11Rα and/or gp130, e.g. IL-11Rα:gp130.

In some embodiments, the IL-11 binding receptor according to the present invention is capable of inhibiting IL-11-mediated signalling to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the IL-11 binding receptor (or in the presence of an appropriate control receptor). In some embodiments, the IL-11 binding receptor is capable of reducing IL-11 mediated signalling to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the IL-11 binding receptor (or in the presence of an appropriate control receptor).

In some embodiments, the IL-11 mediated signalling may be signalling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for IL-11 binding receptor for inhibition of IL-11 mediated signalling may be determined, e.g. by culturing Ba/F3 cells expressing IL-11Rα and gp130 in the presence of human IL-11 and the IL-11 binding agent, and measuring $^3$H-thymidine incorporation into DNA.

In some embodiments, the IL-11 binding receptor of the present invention may exhibit an $IC_{50}$ of 10 μg/ml or less, preferably one of ≤5 μg/ml, ≤4 μg/ml, ≤3.5 μg/ml, ≤3 μg/ml, ≤2 μg/ml, ≤1 μg/ml, ≤0.9 μg/ml, ≤0.8 μg/ml, ≤0.7 μg/ml, ≤0.6 μg/ml, or ≤0.5 μg/ml in such an assay.

In some embodiments, the IL-11 mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment, and IL-11. In some embodiments, the soluble IL-11Rα is a soluble (secreted) isoform of IL-11Rα, or is the liberated product of proteolytic cleavage of the extracellular domain of cell membrane bound IL-11Rα.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα (e.g. hyper IL-11 as described herein).

In some embodiments, the IL-11 binding receptor according to the present invention is capable of inhibiting signalling mediated by binding of IL-11:IL-11Rα complex to gp130, and is also capable of inhibiting signalling mediated by binding of IL-11 to IL-11Rα:gp130 receptor.

In some embodiments, the IL-11 binding receptor is capable of inhibiting fibroblast proliferation. Proliferation of fibroblasts can be determined by analysing cell division over a period of time. Cell division for a given population of fibroblasts can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells (e.g. proliferating fibroblasts) may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the IL-11 binding receptor, the fibroblasts may be cardiac fibroblasts (e.g. atrial fibroblasts), skin fibroblasts, lung fibroblasts, kidney fibroblasts or liver fibroblasts.

In some embodiments, the IL-11 binding receptor according to the present invention is capable of inhibiting fibroblast proliferation to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibroblast proliferation in the absence of the IL-11 binding receptor (or in the presence of an appropriate control receptor). In some embodiments, the IL-11 binding receptor is capable of reducing fibroblast proliferation to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibroblast proliferation in the absence of the IL-11 binding receptor (or in the presence of an appropriate control receptor).

In some embodiments, the IL-11 binding receptor according to the present invention is capable of inhibiting a pathological process mediated by IL-11, e.g. following stimulation with a profibrotic factor (e.g. TGFβ1). Pathological processes mediated by IL-11 include fibrosis, and can be evaluated either in vitro or in vivo.

In some embodiments, the IL-11 binding receptor according to the present invention is capable of inhibiting fibrosis. Fibrosis may be of a particular tissue or several tissues, e.g. liver, lung, kidney, heart, blood vessel, eye, skin, pancreas, spleen, bowel (e.g. large or small intestine), brain, or bone marrow. Fibrosis may be measured by means well known to the skilled person, for example by analysing gene or protein expression of one or more myofibroblast markers and/or gene or protein expression of one or more markers of fibrosis in a given tissue or tissues.

Myofibroblast markers may include one or more of increased αSMA, vimentin, palladin, cofilin or desmin. Markers of fibrosis include increased level of collagen, fibronectin, periostin, IL-6, IL-11, αSMA, TIMP1 and MMP2, extracellular matrix components, number/proportion of myofibroblasts, and organ weight.

Inhibition of fibrosis can be measured in vitro or in vivo. For example, whether an IL-11 binding receptor is capable of inhibiting fibrosis in a given tissue can be analysed in vitro by treating fibroblasts derived from that tissue with a profibrotic stimulus, and then analysing whether the IL-11 binding receptor can reduce myofibroblast generation from the fibroblasts (or e.g. some other marker of fibrosis). Whether an IL-11 binding receptor is capable of inhibiting fibrosis can be analysed in vivo, for example, by administering the IL-11 binding receptor to a subject (e.g. a subject that has been exposed to a profibrotic stimulus), and analysing tissue(s) for one or more markers of fibrosis.

In some embodiments, the IL-11 binding receptor according to the present invention is capable of inhibiting fibrosis to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibrosis in the absence of the IL-11 binding receptor (or in the presence of an appropriate control receptor. In some embodiments, the IL-11 binding receptor is capable of reducing fibrosis to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibrosis in the absence of the IL-11 binding receptor (or in the presence of an appropriate control receptor).

In some embodiments, the IL-11 binding receptor according to the present invention is capable of inhibiting myofibroblast generation from fibroblasts, e.g. following exposure of the fibroblasts to profibrotic factor. Myofibroblast generation from fibroblasts can be investigated by analysis for myofibroblast markers. A profibrotic factor according to the present disclosure may be e.g. TGFβ1, IL-11, IL-13, PDGF, ET-1, oncostatin M (OSM) or ANG2 (AngII).

In some embodiments, the IL-11 binding receptor is capable of inhibiting gene or protein expression in fibroblasts, or fibroblast-derived cells (e.g. myofibroblasts), of one or more of collagen, fibronectin, periostin, IL-6, IL-11, αSMA, TIMP1, MMP2, e.g. following stimulation with a profibrotic factor. In some embodiments, the IL-11 binding receptor is capable of inhibiting gene or protein expression in fibroblasts, or fibroblast-derived cells (e.g. myofibroblasts), of one or more extracellular matrix components, e.g. following stimulation with a profibrotic factor.

In the experimental examples herein, myofibroblast generation from fibroblasts is analysed by measuring αSMA protein expression levels using Operetta High-Content Imaging System following stimulation of the fibroblasts with TGFβ1.

In some embodiments, the IL-11 binding receptor according to the present invention is capable of inhibiting myofibroblast generation from fibroblasts to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of myofibroblast generation from fibroblasts in the absence of the IL-11 binding receptor (or in the presence of an appropriate control receptor). In some embodiments, the IL-11 binding receptor is capable of reducing myofibroblast generation from fibroblasts to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of myofibroblast generation from fibroblasts in the absence of the IL-11 binding receptor (or in the presence of an appropriate control receptor).

In some embodiments, the IL-11 binding receptor according to the present invention is capable of inhibiting gene or protein expression in fibroblasts of one or more of collagen, fibronectin, periostin, IL-6, IL-11, αSMA, TIMP1, MMP2, e.g. following stimulation with a profibrotic factor (e.g. TGFβ1). In some embodiments, the IL-11 binding receptor according to the present invention is capable of inhibiting gene or protein expression to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of gene or protein expression in the absence of the IL-11 binding receptor (or in the presence of an appropriate control receptor). In some embodiments, the IL-11 binding receptor is capable of reducing gene or protein expression to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of gene or protein expression in the absence of the IL-11 binding receptor (or in the presence of an appropriate control receptor).

In some embodiments, the IL-11 binding receptor according to the present invention is capable of inhibiting extracellular matrix production by fibroblasts, e.g. following stimulation with a profibrotic factor (e.g. TGFβ1). Extracellular matrix production can be evaluated, for example, by measuring the level of an extracellular matrix component. Extracellular matrix components according to the present invention include e.g. proteoglycan, heparan sulphate, chondroitin sulphate, keratan sulphate, hyaluronic acid, collagen, periostin, fibronectin, vitronectin, elastin, fibronectin, laminin, nidogen, gelatin and aggrecan.

In some embodiments, the IL-11 binding receptor according to the present invention is capable of inhibiting extracellular matrix production by fibroblasts to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of extracellular matrix production by fibroblasts in the absence of the IL-11 binding receptor (or in the presence of an appropriate control receptor). In some embodiments, the IL-11 binding receptor is capable of reducing extracellular matrix production by fibroblasts to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of extracellular matrix production in the absence of the IL-11 binding receptor (or in the presence of an appropriate control receptor).

In some embodiments, the IL-11 binding receptor according to the present invention is capable of inhibiting proliferation and/or survival of cells of a cancer. The skilled person is able to determine whether an IL-11 binding receptor is capable of inhibiting proliferation and/or survival of cells of a cancer for example by analysing the effect of the IL-11 binding receptor on cells of the cancer. For example, proliferation of cells can be measured as described herein, e.g. by $^3$H thymidine incorporation or CFSE dilution assays. Cell survival can be analysed by measuring cells for markers of cell viability/cell death following treatment with the IL-11 binding receptor.

In some embodiments, the IL-11 binding receptor according to the present invention is capable of inhibiting proliferation and/or survival of cells of a cancer to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of proliferation and/or survival of cells of a cancer in the absence of the IL-11 binding receptor (or in the presence of an appropriate control receptor). In some embodiments, the IL-11 binding receptor is capable of reducing proliferation and/or survival of cells of a cancer to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of proliferation and/or survival of cells of a cancer in the absence of the IL-11 binding receptor (or in the presence of an appropriate control receptor).

In some embodiments, the IL-11 binding receptor according to the present invention is capable of inhibiting tumour growth to less than 100%, e.g. one of 99% or less, 95% or less, 90% or less, 85% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of tumour growth in the absence of the IL-11 binding receptor (or in the presence of an appropriate control receptor). In some embodiments, the IL-11 binding receptor is capable of reducing tumour growth to less than 1 times, e.g. one of ≤0.99 times, ≤0.95 times, ≤0.9 times, ≤0.85 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of tumour growth in the absence of the IL-11 binding receptor (or in the presence of an appropriate control receptor).

Therapeutic Applications

IL-11 binding receptors according to the present invention and compositions comprising such agents may be provided for use in methods of medical treatment or prevent of a disease/disorder, or alleviation of the symptoms of a disease/disorder. The IL-11 binding receptors of the present invention may be administered to subjects having a disease/condition in need of treatment, and/or to subjects at risk of such developing or contracting the disease/disorder.

Treatment, prevention or alleviation of fibrosis according to the present invention may be of fibrosis that is associated with an upregulation of IL-11 and/or IL-11Rα, e.g. an upregulation of IL-11 in cells or tissue in which the disease/disorder occurs or may occur, or upregulation of extracellular IL-11 or IL-11Rα. In some embodiments, IL-11 or IL-11Rα expression is locally or systemically upregulated in the subject.

Treatment or alleviation of a disease/disorder may be effective to prevent progression of the disease/disorder, e.g. to prevent worsening of the condition or to slow the rate of development. In some embodiments treatment or alleviation may lead to an improvement in the disease/disorder, e.g. a reduction in the symptoms of the disease/disorder or reduction in some other correlate of the severity/activity of the disease/disorder.

Prevention of a disease/disorder may refer to prevention of a worsening of the condition or prevention of the development of the disease/disorder, e.g. preventing an early stage disease/disorder developing to a later, chronic, stage.

The IL-11 binding receptors of the present invention are preferably able to bind to and inhibit the biological activity of IL-11 and IL-11-containing molecules/complexes (e.g. IL-11:IL-11Rα complex). Accordingly, the IL-11 binding receptors of the present invention find use in the treatment or prevention of diseases and disorders in which IL-11 and/or IL-11Rα is implicated in the pathology of the disease/disorder. That is, the IL-11 binding receptors of the present invention find use in the treatment or prevention of diseases and disorders associated with IL-11/IL-11R signalling.

In some embodiments, the disease/disorder may be associated with increased IL-11. IL-11Rα and/or gp130 gene or protein expression, e.g. as compared to the control (i.e. non-diseased) state. In some embodiments, the disease/disorder may be associated with an increased level of IL-11/IL-11R signalling as compared to the control state. In some embodiments, the disease/disorder may be associated with an increased level of signalling through ERK and/or STAT3 pathways as compared to the control state. In some embodiments, the increased expression/activity of IL-11, IL-11Rα and/or gp130, and/or the increased level of IL-11/IL-11R signalling, may be observed in effector cells of the disease/disorder (e.g. for a cancer, the cancerous cells). In some embodiments, the increased expression/activity of IL-11, IL-11Rα and/or gp130, and/or the increased level of IL-11/IL-11R signalling, may be observed in cells other than the effector cells.

Signalling through ERK can be measured e.g. using an assay for ERK phosphorylation such as an assay described in Assay Guidance Manual: Phospho-ERK Assays, Kim E. Garbison, Beverly A. Heinz, Mary E. Lajiness, Jeffrey R. Weidner, and G. Sitta Sittampalam, Eli Lilly & Company, Sittampalam G S, Coussens N P, Nelson H, et al., editors Bethesda (Md.): Eli Lilly & Company and the National Center for Advancing Translational Sciences; 2004. Signalling through STAT3 can be measured e.g. using an assay for phosphorylation of STAT3, such as the Phospho-STAT3 (Tyr705) Cellular Assay Kit (Cisbio Assays).

In some embodiments, the treatment is of a disease/disorder for which a reduction in IL-11/IL-11R signalling is therapeutic. In some embodiments, the treatment is of a disease/disorder associated with excess ERK and/or STAT3 signalling. In some embodiments, the treatment is of a disease/disorder associated with excess proliferation or hyperactivation of fibroblasts, or associated with an excess of myofibroblasts.

In some embodiments, the treatment may be aimed at preventing or treating a disease/disorder by decreasing the number or proportion of myofibroblasts or αSMA-positive fibroblasts.

In some embodiments, the disease/disorder may be fibrosis, a fibrotic condition, or a disease/disorder characterised by fibrosis. As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety. The main cellular effectors of fibrosis are myofibroblasts, which produce a collagen-rich extracellular matrix.

In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June; 25(6): 700-6). Environmental injury/stimuli may include exposure to asbestos fibres or silica.

Fibrosis can occur in many tissues of the body. For example, fibrosis can occur in the lung, liver (e.g. cirrhosis), kidney, heart, blood vessels, eye, skin, pancreas, spleen, bowel (e.g. large or small intestine), brain, and bone marrow. Fibrosis may also occur in multiple organs at once.

In embodiments herein, fibrosis may involve an organ of the gastrointestinal system, e.g. of the liver, small intestine, large intestine, or pancreas. In some embodiments, fibrosis may involve an organ of the respiratory system, e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

In some preferred embodiments, the fibrosis is cardiac or myocardial fibrosis, hepatic fibrosis, or renal fibrosis. In some embodiments cardiac or myocardial fibrosis is associated with dysfunction of the musculature or electrical properties of the heart, or thickening of the walls or valves of the heart. In some embodiments fibrosis is of the atrium and/or ventricles of the heart. Treatment or prevention of atrial or ventricular fibrosis may help reduce risk or onset of atrial fibrillation, ventricular fibrillation, or myocardial infarction.

In some preferred embodiments hepatic fibrosis is associated with chronic liver disease or liver cirrhosis. In some preferred embodiments renal fibrosis is associated with chronic kidney disease.

Diseases/disorders characterised by fibrosis in accordance with the present invention include but are not limited to: respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, primary biliary cirrhosis (PBC), schistosomal liver disease, liver cirrhosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS); chronic graft versus host disease; diseases/disorders of the eye and associated processes, such as Grave's opthalmopathy, epiretinal fibrosis (e.g. diabetic retinopathy (DR)), glaucoma, subretinal fibrosis (e.g. associated with macular degeneration (e.g. wet age-related macular degeneration (AMD))), macular edema, drusen formation, post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

It will be appreciated that many of the diseases/conditions listed above are interrelated. For example, fibrosis of the ventricle may occur post myocardial infarction, and is associated with DCM, HCM and myocarditis.

In particular embodiments, the disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Chron's disease, post-surgical fibrosis or retinal fibrosis, e.g. associated with wet age-related macular degeneration (AMD).

Fibrosis can lead directly or indirectly to, and/or increase susceptibility to development of, diseases/disorders. For example, more than 80% of hepatocellular carcinomas (HCCs) develop in fibrotic or cirrhotic livers (Affo et al. 2016, Annu Rev Pathol.), suggesting an important role for liver fibrosis in the premalignant environment (PME) of the liver.

Accordingly, the antibodies/fragments of the present invention find use in methods for the treatment and prevention of diseases/disorders associated with fibrosis, and/or for which fibrosis is a risk factor. In some embodiments, the disease/disorder associated with fibrosis, or for which fibrosis is a risk factor, is a cancer, e.g. cancer of the liver (e.g. hepatocellular carcinoma).

IL-11/IL-11R signalling is also implicated in the pathology of other diseases/disorders, and the IL-11 binding receptors of the present invention accordingly find use in methods to treat, prevent and/or alleviate the symptoms of these diseases/disorders also.

IL-11/IL-11R signalling has been implicated in the development and progression of various cancers. Studies suggest that IL-11/IL-11R signalling is important for promoting chronic gastric inflammation and associated gastric, colonic, hepatocellular and breast cancer tumorogenesis through excessive activation of STAT3 (Ernst M, et al. J Clin Invest. (2008); 118:1727-1738), that IL-11/IL-11R signalling may promote tumorigenesis by triggering the JAK-STAT intracellular signalling pathway, and may also promote metastasis via signalling through the PI3K-AKT-mTORC1 pathway (Xu et al., Cancer Letters (2016) 373(2): 156-163). Through STAT3, IL-11 promotes survival, proliferation, invasion angiogenesis and metastasis, the IL-11/GP130/JAK/STAT3 signalling axis may be rate-limiting for the progression of gastrointestinal tumors, and elevated IL-11 expression is associated with poor prognosis of breast cancer patients (Johnstone et al., Cytokine & Growth Reviews (2015) 26(5): 489-498). IL-11/IL-11R signalling has also been shown to influence breast cancer stem cell dynamics and tumor heterogeneity (Johnstone et al., Cytokine & Growth Reviews (2015) 26(5): 489-498). Recently, IL-11 signalling has been implicated in chemoresistance of lung adenocarcinoma; cancer associated fibroblasts were found to upregulate IL-11, and confer chemoresistance to lung cancer cells through activation of the IL-11/IL-11R/STAT3 anti-apoptotic signalling pathway (Tao et al. 2016, Sci Rep. 6; 6:38408). IL-11 signalling may promote the fibroblast-to-myofibroblast transition and extracellular matrix production by fibroblasts in the pre-malignant environment (PME) and tumour micro-environment (TME).

In some embodiments, the IL-11 binding receptors of the present invention are provided for use in methods to treat/prevent a cancer. In some embodiments, the cancer may be a cancer which leads directly or indirectly to inflammation and/or fibrosis.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue.

In some embodiments, the IL-11 binding receptors of the present invention are provided for use in methods to treat/prevent a cancer, e.g. an epithelial cell cancer, breast cancer, gastrointestinal cancer (e.g. esophageal cancer, stomach cancer, pancreatic cancer, liver cancer, gallbladder cancer, colorectal cancer, anal cancer, gastrointestinal carcinoid tumor), and lung cancer (e.g. non-small cell lung cancer (NSCLC) or small cell lung cancer (SCLC))). In some embodiments, the cancer is a cancer for which acute and/or chronic inflammation is a risk factor.

In some embodiments, the cancer may be associated with increased IL-11, IL-11Rα and/or gp130 gene or protein expression. For example, cells of the cancer may have increased expression of IL-11, IL-11Rα and/or gp130 as compared to comparable, non-cancerous cells, or may be associated with increased expression of IL-11, IL-11Rα and/or gp130 by other cells (e.g. non-cancerous cells) as compared to the level of expression by comparable cells in the absence of a cancer (e.g. in a healthy control subject). In some embodiments, cells of the cancer may be determined to have an increased level of signalling through ERK and/or STAT3 pathways as compared to comparable non-cancerous cells.

In some embodiments, the cancer may be associated with a mutation in IL-11, IL-11Rα and/or gp130. In some embodiments, such mutation may be associated with increased level of gene or protein expression, or may be associated with an increased level of IL-11/IL-11R signalling relative to the level of expression/signalling observed in the absence of the mutation.

IL-11/IL-11R signalling has also been implicated in diseases/disorders characterised by inflammation. Intra-articular injection of IL-11 has been shown to cause joint inflammation (Wong et al., Cytokine (2005) 29:72-76), and IL-11 has been shown to be proinflammatory at sites of IL-13-mediated tissue inflammation (Chen et al., J Immunol (2005) 174:2305-2313). IL-11 expression has also been observed to be significantly increased in chronic skin lesions in atopic dermatitis, and is known to be involved in bronchial inflammation (Toda et al., J Allergy Clin Immunol (2003) 111: 875-881). IL-11/IL-11R signalling is implicated in inflammatory bowel disease (IBD) and asthma (Putoczki and Ernst, J Leuko Biol (2010) 88(6)1109-1117). IL-11 has also been identified as a risk factor for multiple sclerosis; IL-11 is elevated in the cerebrospinal fluid of patients with clinically isolated syndrome (CIS) as compared to control subjects, and serum levels of IL-11 are higher during relapses for patients with relapsing-remitting multiple sclerosis, and IL-11 may promote differentiation of CD4+ T cells to a $T_H17$ phenotype—T$_H$17 cells are important cells in the pathogenesis of multiple sclerosis (Zhang et al., Oncotarget (2015) 6(32): 32297-32298).

In some embodiments, the IL-11 binding receptors of the present invention are provided for use in methods to treat/prevent a disease/disorder characterised by inflammation. In some embodiments, a disease or disorder characterised by inflammation may be a disease/disorder which leads directly or indirectly to a cancer and/or fibrosis. Diseases characterised by inflammation include e.g. allergic inflammation such as allergic asthma and bronchial inflammation, atopic dermatitis, allergic rhinitis and ocular allergic diseases, and autoimmune diseases such as multiple sclerosis, systemic lupus erythematosus, rheumatoid arthritis, chronic active hepatitis, type 1 diabetes mellitus, celiac disease, Grave's disease, uveitis, pemphigus, psoriasis, Crohn's disease, ulcerative colitis, inflammatory bowel disease, anaemia and autoimmune thyroiditis.

In some embodiments, the IL-11 binding receptors of the present invention are provided for use in methods to treat/prevent a disease/disorder associated with infection, in particular where infection leads directly or indirectly to fibrosis, cancer or inflammation. A disease associated with infection may be a disease which is caused or exacerbated by infection with the relevant infectious agent, or may be a disease for which infection with the relevant infectious agent is a risk factor.

An infection may be any infection or infectious disease, e.g. bacterial, viral, fungal, or parasitic infection. In particular embodiments, the disease/disorder may be associated with a viral infection. In some embodiments it may be particularly desirable to treat chronic/persistent infections, e.g. where such infections are associated with inflammation, cancer and/or fibrosis.

The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori* and *Mycobacterium tuberculosis* infection of the lung. Examples of viral infections include infection with EBV, HPV, HIV, hepatitis B or hepatitis C.

The treatment may involve ameliorating, treating, or preventing the disease/disorder by inhibiting the biological activity of IL-11 or an IL-11-containing complex. Such methods may include the administration of the IL-11 binding receptors/compositions according to the present invention to bind to and inhibit the biological activity of IL-11 or an IL-11-containing complex. Herein, inhibiting the biological activity of IL-11 or an IL-11-containing complex may be referred to as 'neutralising'.

Methods of treatment may optionally include the co-administration of biological adjuvants (e.g., interleukins, cytokines, Bacillus Comette-Guerin, monophosphoryl lipid A, etc.) in combination with conventional therapies for treating cancer such as treatment with an agent for treating cancer (e.g. chemotherapy), radiation, or surgery. Methods of treatment may involve administering a composition according to the present invention as a vaccine that works by activating the immune system to prevent or destroy cancer cell growth. Methods of medical treatment may also involve in vivo, ex vivo, and adoptive immunotherapies, including those using autologous and/or heterologous cells or immortalized cell lines.

The treatment may be aimed at prevention of a disease/disorder associated with overactive/elevated IL-11/IL-11R mediated signalling. As such, the IL-11 binding receptors may be used to formulate pharmaceutical compositions or medicaments and subjects may be prophylactically treated against development of a disease state. This may take place before the onset of symptoms of the disease state, and/or may be given to subjects considered to be at greater risk of the disease or disorder.

Treatment may comprise co-therapy with a vaccine, which may involve simultaneous, separate or sequential therapy, or combined administration of vaccine and the IL-11 binding receptor or composition according to the invention.

Administration of receptor is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

IL-11 binding receptors according to the present invention may be formulated as pharmaceutical compositions or medicaments for clinical use and may comprise a pharmaceutically acceptable carrier, diluent, excipient or adjuvant.

The composition may be formulated for topical, parenteral, systemic, intracavitary, intravenous, intra-arterial, intramuscular, intrathecal, intraocular, intraconjunctival, intratumoral, subcutaneous, oral or transdermal routes of administration which may include injection or infusion. Suitable formulations may comprise the IL-11 binding receptor in a sterile or isotonic medium. Medicaments and pharmaceutical compositions may be formulated in fluid, including gel, form. Fluid formulations may be formulated for administration by injection or via catheter to a selected region of the human or animal body.

In accordance with the present invention methods are also provided for the production of pharmaceutically useful compositions, such methods of production may comprise one or more steps selected from: isolating an IL-11 binding receptor as described herein; and/or mixing an isolated receptor as described herein with a pharmaceutically acceptable carrier, adjuvant, excipient or diluent.

For example, a further aspect of the present invention relates to a method of formulating or producing a medicament or pharmaceutical composition for use in a method of medical treatment, the method comprising formulating a pharmaceutical composition or medicament by mixing an IL-11 binding receptor as described herein with a pharmaceutically acceptable carrier, adjuvant, excipient or diluent.

Methods of Detection

IL-11 binding receptors described herein may be used in methods that involve the binding of the IL-11 binding receptor to IL-11. Such methods may involve detection of the bound complex of receptor and IL-11. As such, in one embodiment a method is provided, the method comprising contacting a sample containing, or suspected to contain, IL-11 with an IL-11 binding receptor as described herein and detecting the formation of a complex of the IL-11 binding receptor, and IL-11.

Suitable method formats are well known in the art, including immunoassays such as sandwich assays, e.g. ELISA. The method may involve labelling the IL-11 binding receptor, or IL-11, or both, with a detectable label, e.g. fluorescent, luminescent or radio-label. IL-11 expression may be measured by immunohistochemistry (IHC), for example of a tissue sample obtained by biopsy. In some embodiments, the label may be selected from: a radionucleotide, positron-emitting radionuclide (e.g. for positron emission tomography (PET)), MRI contrast agent or fluorescent label.

Analysis in vitro or in vivo of processes mediated by IL-11 may involve analysis by positron emission tomography (PET), magnetic resonance imaging (MRI), or fluorescence imaging, e.g. by detection of appropriately labelled species.

Methods of this kind may provide the basis of a method of diagnosis of a disease or condition requiring detection and or quantitation of IL-11 or an IL-11-containing complex. Such methods may be performed in vitro on a subject sample, or following processing of a subject sample. Once the sample is collected, the subject is not required to be present for the in vitro method of diagnosis to be performed and therefore the method may be one which is not practised on the human or animal body.

Such methods may involve determining the amount of IL-11 or IL-11-containing complex present in a subject sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of IL-11 or IL-11-containing complex present in a subject sample may be indicative that a subject may respond to treatment with an IL-11 binding receptor, e.g. an IL-11 binding receptor or composition according to the present invention. The presence of a high level of IL-11 or IL-11-containing complex in a sample may be used to select a subject for treatment with an IL-11 binding receptor or composition described herein. The IL-11 binding receptors of the present invention may therefore be used to select a subject for treatment with IL-11 binding receptor therapy.

Detection in a sample of IL-11 or IL-11-containing complex may be used for the purpose of diagnosis of an infectious disease, autoimmune disorder or a cancerous condition in the subject, diagnosis of a predisposition to an infectious disease, autoimmune disorder or a cancerous condition or for providing a prognosis (prognosticating) of an infectious disease, autoimmune disorder or a cancerous condition. The diagnosis or prognosis may relate to an existing (previously diagnosed) infectious, inflammatory or autoimmune disease/disorder or cancerous condition.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/disorder (e.g. tissue or tissues in which symptoms of the disease manifest, or which are involved in the pathogenesis of the disease/disorder).

Methods according to the present invention may preferably be performed in vitro. The term "in vitro" is intended to encompass experiments with cells in culture whereas the term "in vivo" is intended to encompass experiments with and/or treatment of intact multi-cellular organisms.

Combination Therapies

IL-11 binding receptors and compositions according to the present invention may be administered alone or in combination with other treatments. Administration of such combination may be simultaneous or sequential, depending on the disease/disorder to be treated. The other treatment with which the IL-11 binding receptor or composition is administered may be aimed at treating or preventing the disease/disorder. In some embodiments, the other treatment with which the IL-11 binding receptor or composition is administered may be aimed at treating or preventing e.g. infection, inflammation and/or cancer.

Simultaneous administration refers to administration of the IL-11 binding receptor and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the IL-11 binding receptor or therapeutic agent followed after a given time interval by separate administration of the other agent. It is not required that the two agents are administered by the same route, although this is the case in some embodiments. The time interval may be any time interval.

In some embodiments, treatment with an IL-11 binding receptor or composition of the present invention may be accompanied by an agent for treating or preventing infection (e.g. an antibiotic, anti-viral, anti-fungal or anti-parasitic agent). In some embodiments, treatment with an IL-11 binding receptor or composition of the present invention may be accompanied by an agent for treating or preventing inflammation (e.g. a non-steroidal anti-inflammatory drug (NSAID). In some embodiments, treatment with an IL-11 binding receptor or composition of the present invention may be accompanied by radiotherapy (i.e. treatment with ionising radiation, e.g. X-rays or γ-rays) and/or an agent for treating or preventing cancer (e.g. a chemotherapeutic agent). In some embodiments, the IL-11 binding receptor or composition of the present invention may be administered as part of a combination treatment with an immunotherapy.

A treatment may involve administration of more than one drug. A drug may be administered alone or in combination with other treatments, either simultaneously or sequentially dependent upon the condition to be treated.

Routes of Administration

IL-11 binding receptors, medicaments and pharmaceutical compositions according to aspects of the present invention may be formulated for administration by a number of routes, including but not limited to, parenteral, intravenous, intra-arterial, intraocular, intraconjunctival, intramuscular, subcutaneous, intradermal, intratumoral injection or infusion, and oral administration. IL-11 binding receptors, polypeptides and other therapeutic agents, may be formulated in fluid or solid form. Fluid formulations may be formulated for administration by injection or infusion to a selected region of the human or animal body.

Kits

In some aspects of the present invention a kit of parts is provided. In some embodiments the kit may have at least one container having a predetermined quantity of the IL-11 binding receptor or composition. The kit may provide the IL-11 binding receptor in the form of a medicament or pharmaceutical composition, and may be provided together with instructions for administration to a subject in order to treat a specified disease/disorder. The IL-11 binding receptor or composition may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

In some embodiments the subject may be at risk of developing/contracting a disease or disorder.

Protein Expression

Molecular biology techniques suitable for producing the proteins (e.g. the IL-11 binding receptors) according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing polypeptides according to the invention. The cell may be a prokaryote or eukaryote. Suitable prokaryotic cells include *E. coli*. Examples of eukaryotic cells include a yeast cell, a plant cell, insect cell or a mammalian cell (e.g. Chinese Hamster Ovary (CHO) cells). In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides from cell culture known in the art may be used. In order to isolate a polypeptide of interest from a culture, it may be necessary to first separate the cultured cells from media containing the polypeptide of interest. If the polypeptide of interest is secreted from the cells, the cells may be separated from the culture media that contains the secreted polypeptide by centrifugation. If the polypeptide of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide of interest.

It may then be desirable to isolate the polypeptide of interest from the supernatant or culture medium, which may contain other protein and non-protein components. A common approach to separating polypeptide components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures, in which:

FIG. 17. Amino acid sequences of decoy IL-11 receptors, and component sequences thereof. (A) Amino acid sequences for Decoy IL-11 Receptor 1 (D11R1). (B) Amino acid sequences for Decoy IL-11 Receptor 2 (D11R2).

FIG. 18. Nucleotide sequences of vector inserts encoding decoy IL-11 receptors, and component sequences thereof. EcoRI, Kozak and HindIII sequences are indicated (underlined). (A) Nucleotide sequences for Decoy IL-11 Receptor 1 (D11R1). (B) Nucleotide sequences for Decoy IL-11 Receptor 2 (D11R2).

FIG. 20. Amino acid sequence alignment of human and murine gp130 sequences. (A) alignment of extracellular domain (ECD) regions of human and murine gp130. (B) alignment of cytokine binding modules (i.e. D1 to D3) of human and murine gp130.

FIG. 21. Amino acid sequence alignment of human and murine IL-11Rα sequences. (A) alignment of extracellular domain (ECD) regions of human and murine IL-11Rα. (B) alignment of cytokine binding modules (i.e. D2 and D3) of human and murine IL-11Rα.

FIG. 29. Sequence of Human gp130 (Genbank accession no. NP_002175.2). Signal peptide (residues 1-22); extracellular domain (residues 23-619); D1 (residues 26-112); D2 (residues 121-215); D3 (residues 222-321); transmembrane domain (residues 620-641); intracellular domain (residues 642-918).

FIG. 30. Sequence of Human IL-11 Ra (Genbank accession no. NP_001136256.1; UniProt Q14626). Signal peptide (residues 1-22); extracellular domain (residues 23-370); D1 (residues 27-110); D2 (residues 112-219); D3 (residues 220-317); transmembrane domain (residues 371-391); intracellular domain (residues 392-422).

FIG. 31. Sequence corresponding to SEQ ID NO: 17.D1 (residues 26-112 of SEQ ID NO:17); D2 (residues 121-215 of SEQ ID NO:17); D3 (residues 222-321 of SEQ ID NO: 17).

FIG. 32. Sequence corresponding to SEQ ID NO: 18. D2 (residues 112-219 of SEQ ID NO:18); D3 (residues 220-317 of SEQ ID NO:18).

EXAMPLES

In the following Examples, the inventors identify a role for IL-11/IL-11 R signalling in fibrosis in a variety of tissues, and describe the design, production and functional characterisation of decoy IL-11 receptors.

Example 1: A Role for IL-11 in Fibrosis 1.1 IL-11 is Upregulated in Fibrosis

Figure 1:
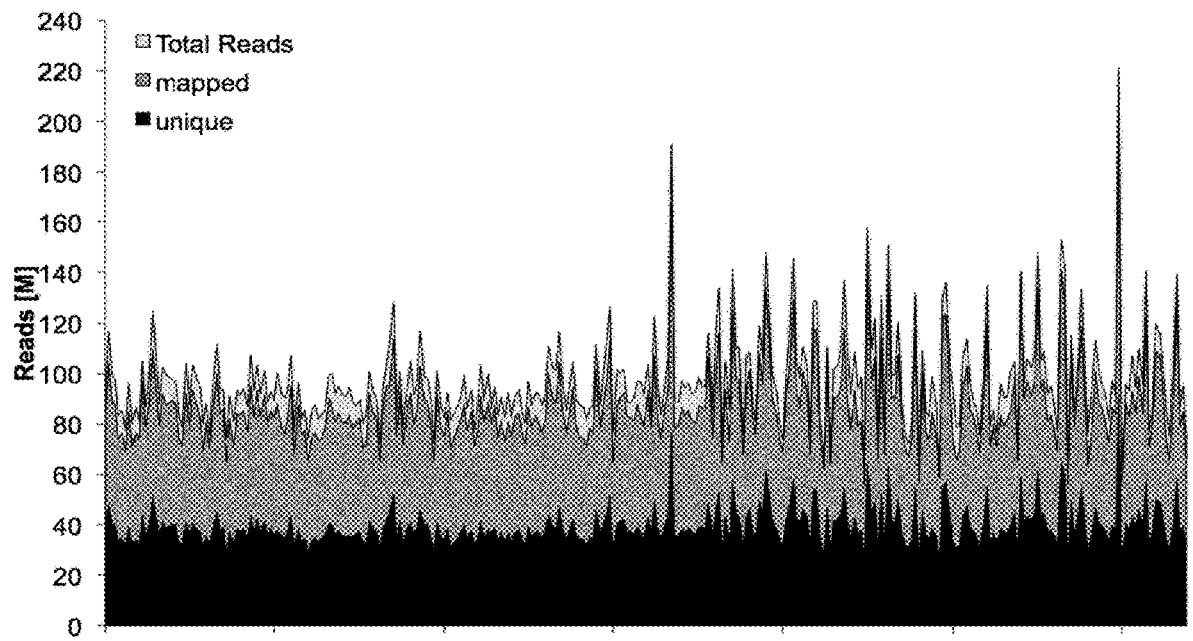
FIG. 1. Graph showing read depth for whole transcriptome sequencing of human atrial fibroblasts from 160 individuals with and without stimulation with TGFβ1.
Figure 2A:
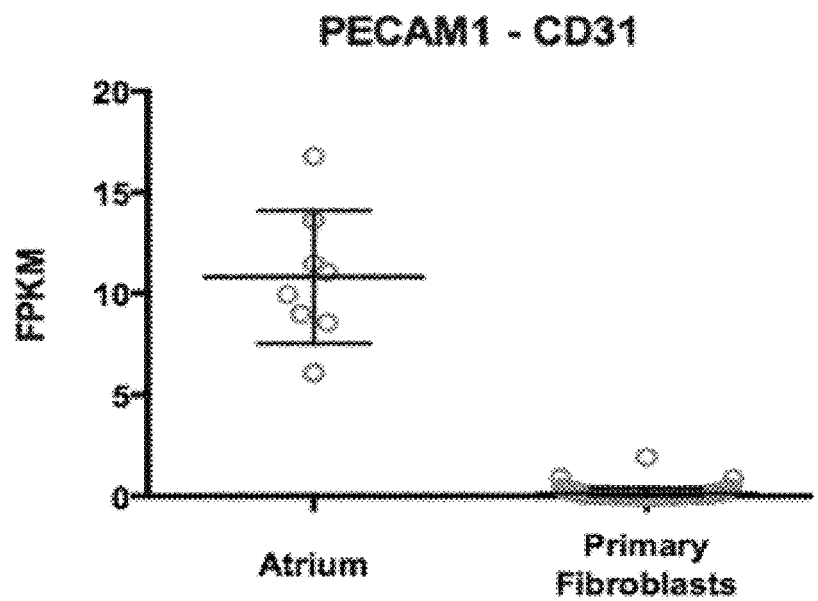
FIG. 2. Graphs showing expression of endothelial, cardiomyocyte and fibroblast marker genes as determined by RNA-seq of the tissue of origin (human atrial tissues samples, n=8) and primary, unstimulated fibroblast cultures. (A) PECAM1, (B) MYH6 (C) TNNT2, (D) COL1A2, and (E) ACTA2.
Figure 2B:
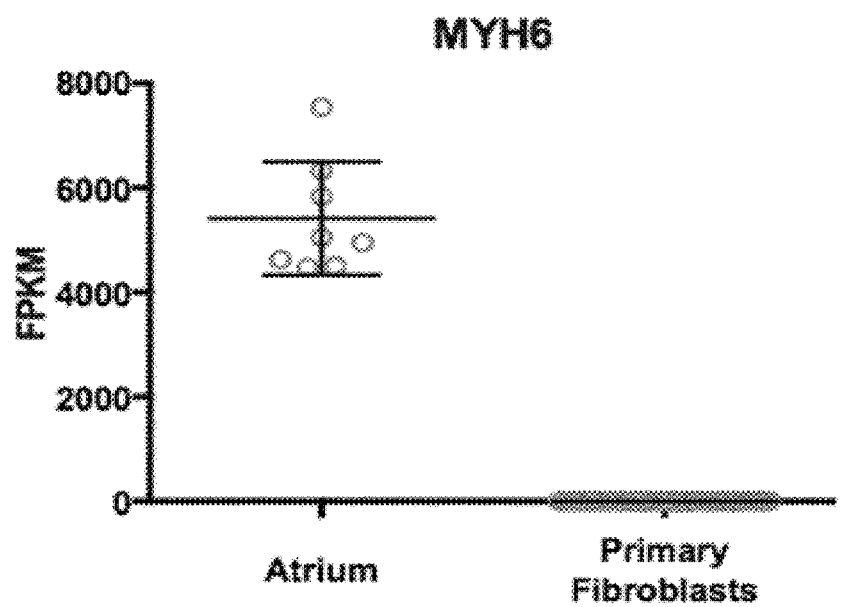
Figure 2C:
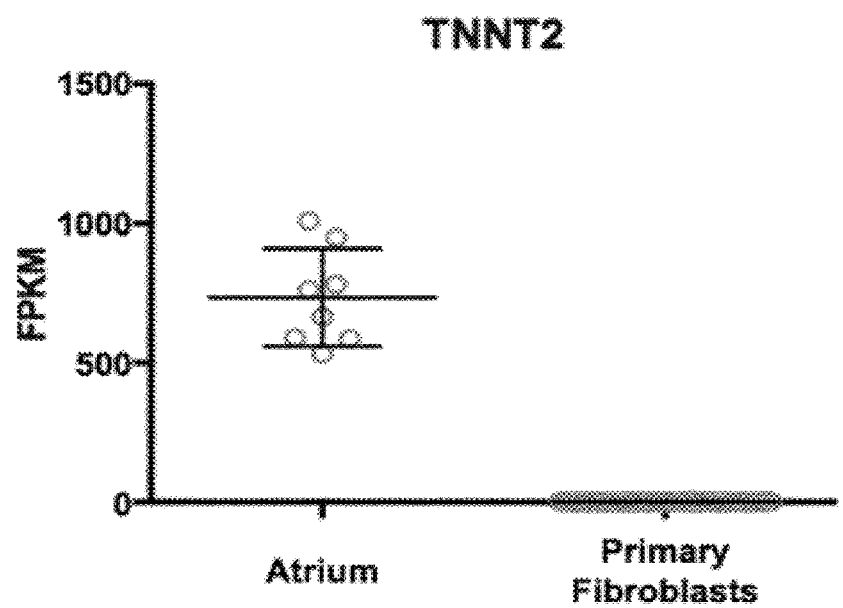
Figure 2D:
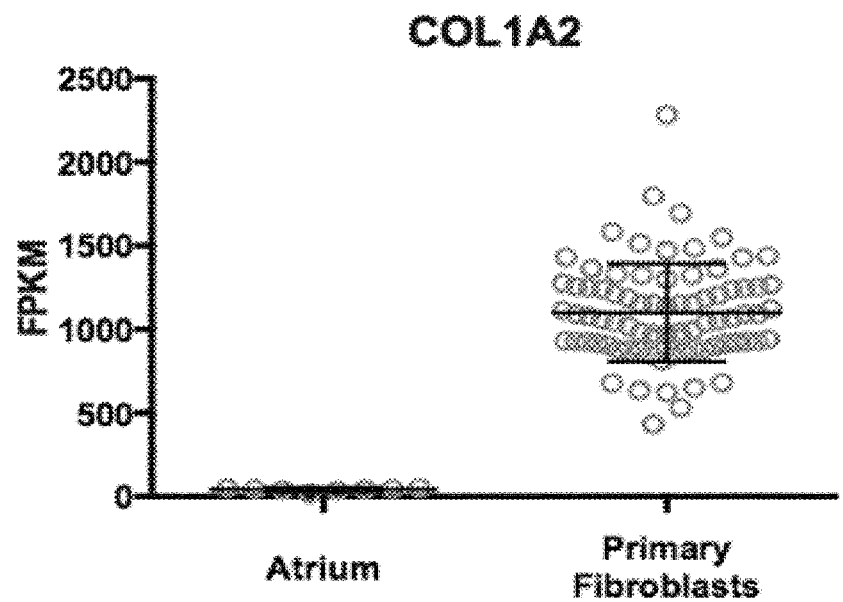
Figure 2E:
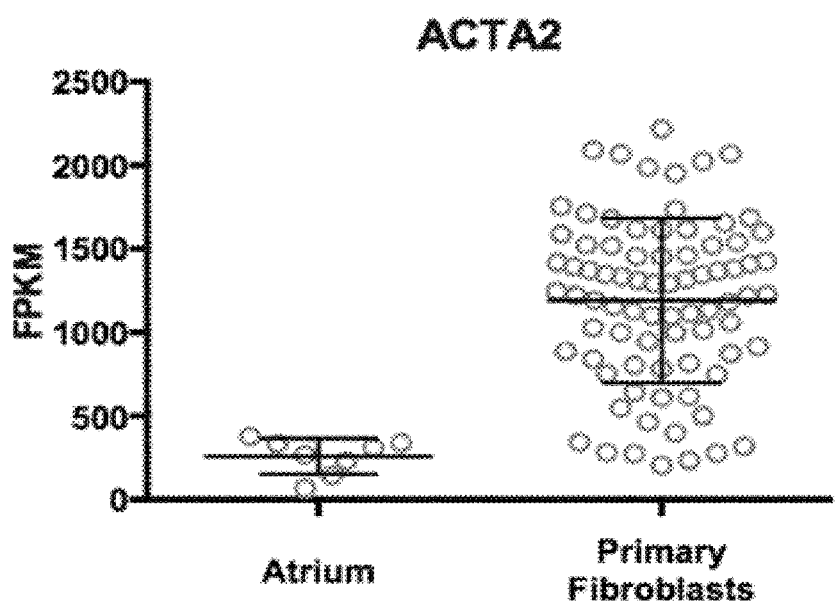

To understand the molecular processes underlying the transition of fibroblasts to activated myofibroblasts, atrial tissue was obtained from more than 200 patients that underwent cardiac bypass surgery at the National Heart Centre Singapore. Cells were cultured in vitro at low passage (passage<4), and either not stimulated or stimulated with TGFβ1 for 24 h. We subsequently performed high-throughput RNA sequencing (RNA-seq) analysis of unstimulated fibroblasts and cells stimulated with the prototypic pro-fibrotic stimulus TGFβ1 across 160 individuals; average read depth was ~70M reads per sample (paired-end 100 bp; FIG. 1).

To ensure the purity of the atrial fibroblast cell cultures, we analysed expression of endothelial cell, cardiomyocyte and fibroblast cell type marker genes from the atrium (Hsu et al., 2012 Circulation Cardiovasc Genetics 5, 327-335) in the RNA-seq dataset.

The results are shown in FIGS. 2A to 2E, and confirm the purity of the atrial fibroblast cultures.

Gene expression was assessed by RNA-seq of the tissue of origin (human atrial tissues samples, n=8) and primary, unstimulated fibroblast cultures. No/very low expression of the endothelial cell marker PECAM1 (FIG. 2A), and the cardiomyocyte markers MYH6 (FIG. 2B) and TNNT2 (FIG. 2C) was detected in the fibroblast cell culture samples. Markers for fibroblasts COL 1A2 (FIG. 2D) and ACTA2 (FIG. 2E) were highly expressed compared to the tissue of origin.

Next, the RNA-seq data was analysed to identify genes whose expression was increased or decreased upon stimulation with TGFβ1, and this information was integrated with the large lRNA-seq dataset across 35+ human tissues provided by the GTEx project (The GTEx Consortium, 2015 Science 348, 648-660). This enabled the identification of gene expression signatures that were specific to the fibroblast-myofibroblast transition.

Figure 3A:
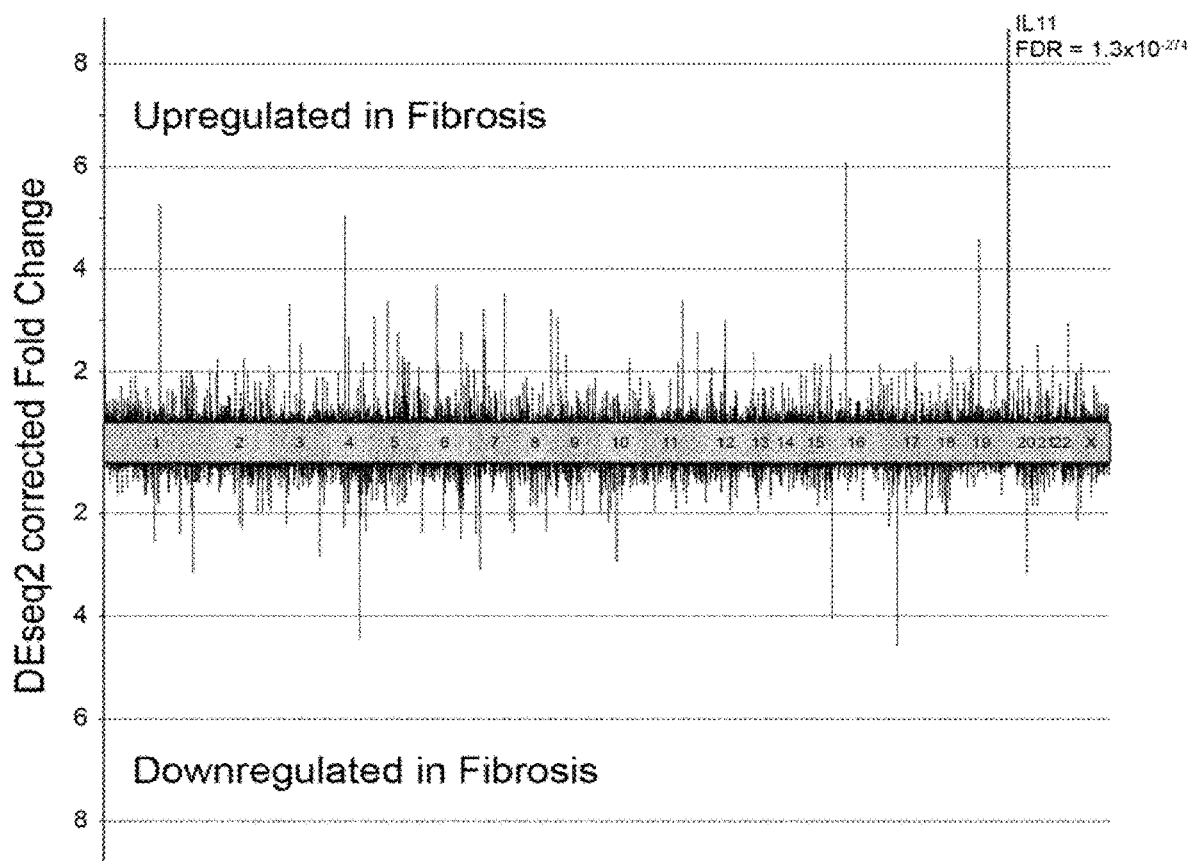
FIG. 3. Graphs showing upregulation of IL-11 expression in fibroblasts in response to stimulation with TGFβ1. (A and B) Graphs showing fold change in gene expression in fibrosis; IL-11 is the most upregulated gene in response to TGFβ1 treatment. (C) IL-11 secretion by fibroblasts in response to stimulation with TGFβ1 (D) Comparison of IL-11 gene expression in tissues of healthy individuals and in atrial fibroblasts, with or without TGFβ1 stimulation. (E) Correspondence of fold change in IL-11 expression as determined by RNA-seq vs. qPCR.
Figure 3B:
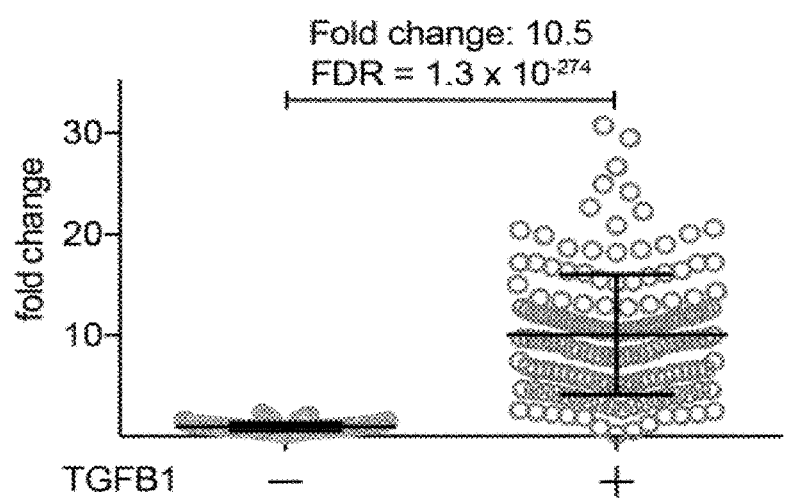

The results are shown in FIGS. 3A to 3E. Across the 10000+ genes expressed in the fibroblasts, IL-11 was the most strongly upregulated gene in response to stimulation with TGFβ1, and on average across the 160 individuals was upregulated more than 10-fold (FIG. 3B).

Figure 3C:
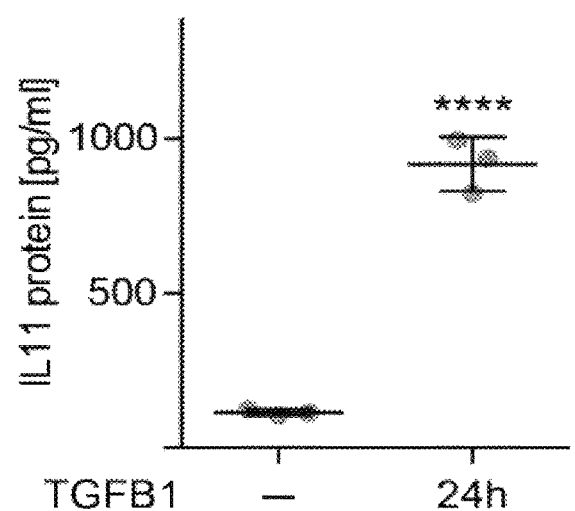
Figure 3D:
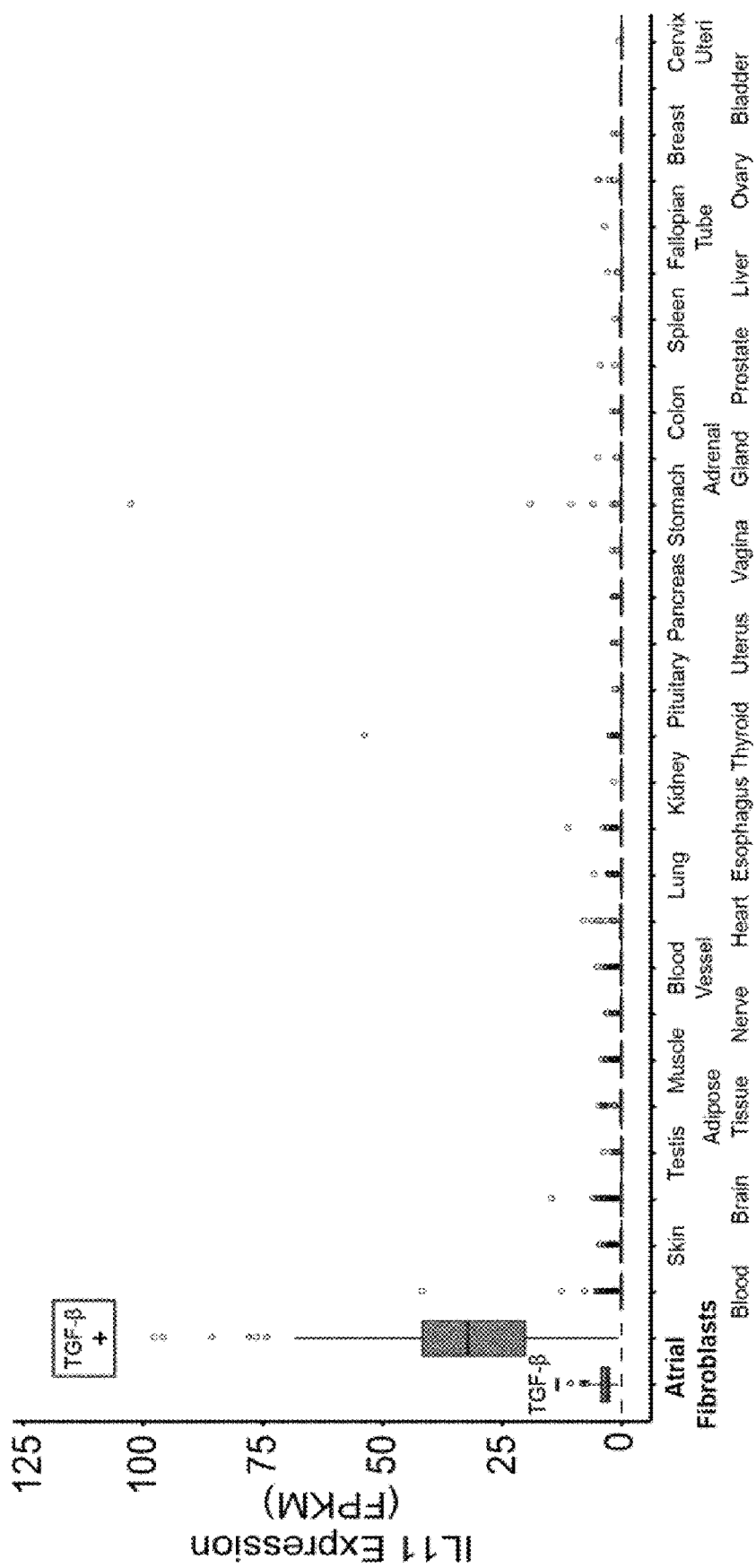
Figure 3E:
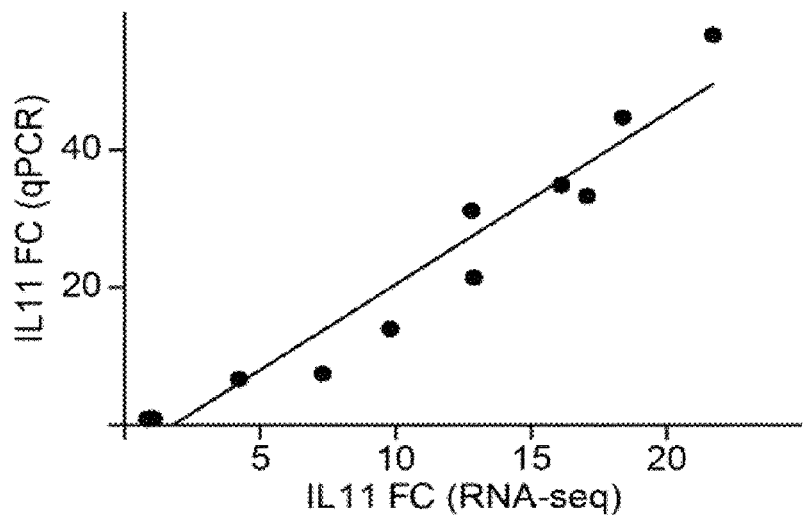

Upregulation of IL-11 expression was confirmed by ELISA analysis of the cell culture supernatant of TGFβ1 stimulated fibroblasts (FIG. 3C). As compared to the level of expression level of IL-11 in other tissues of healthy individuals, this response was observed to be highly specific to activated fibroblasts (FIG. 3D). Various fold changes of IL-11 RNA expression were also confirmed by qPCR analysis (FIG. 3E).

Next, fibroblasts were cultured in vitro and stimulated with several other known pro-fibrotic factors: ET-1, ANGIi, PDGF, OSM and IL-13, and also with human recombinant IL-11. For analysing upregulation of IL-11 produced in response to stimulation with IL-11, it was confirmed that the ELISA was only able to detect native IL-11 secreted from cells and does not detect recombinant IL-11 used for the stimulations (FIG. 4B).

Figure 4A:
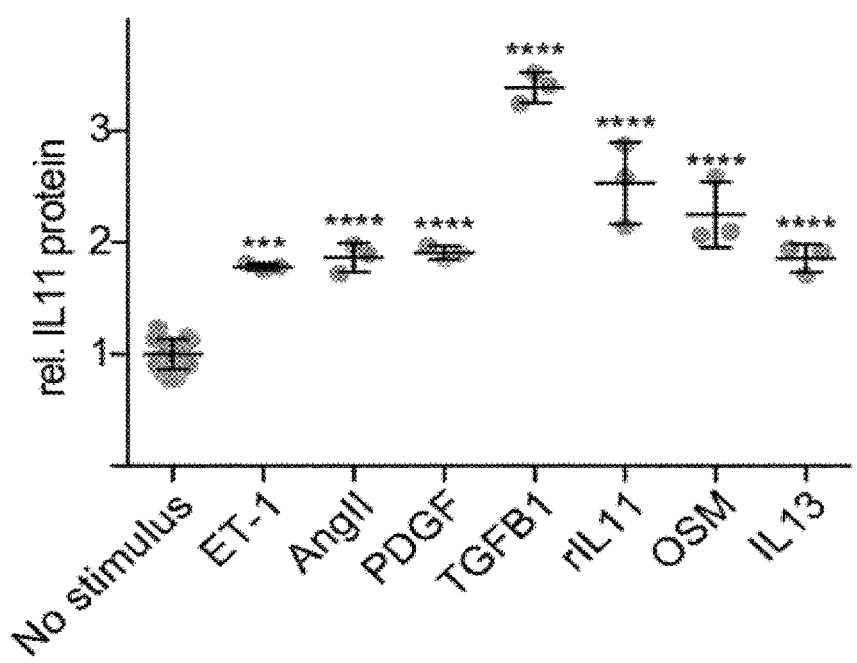
FIG. 4. Graphs showing induction of IL-11 secretion in primary fibroblasts by various profibrotic cytokines, as determined by ELISA. (A) TGFβ1, ET-1, AngII, PDGF, OSM and IL-13 induce IL-11 secretion, and IL-11 also induces IL-11 expression in a positive feedback loop. (B) Graph showing that the ELISA only detects native IL-11 secreted from cells, and does not detect recombinant IL-11 used for the IL-11 stimulation condition. (C) and (D) Cells were stimulated with recombinant IL-11, IL-11 RNA was measured and the native IL-11 protein level was measured in the cell culture supernatant by ELISA at the indicated time points.
Figure 4B:
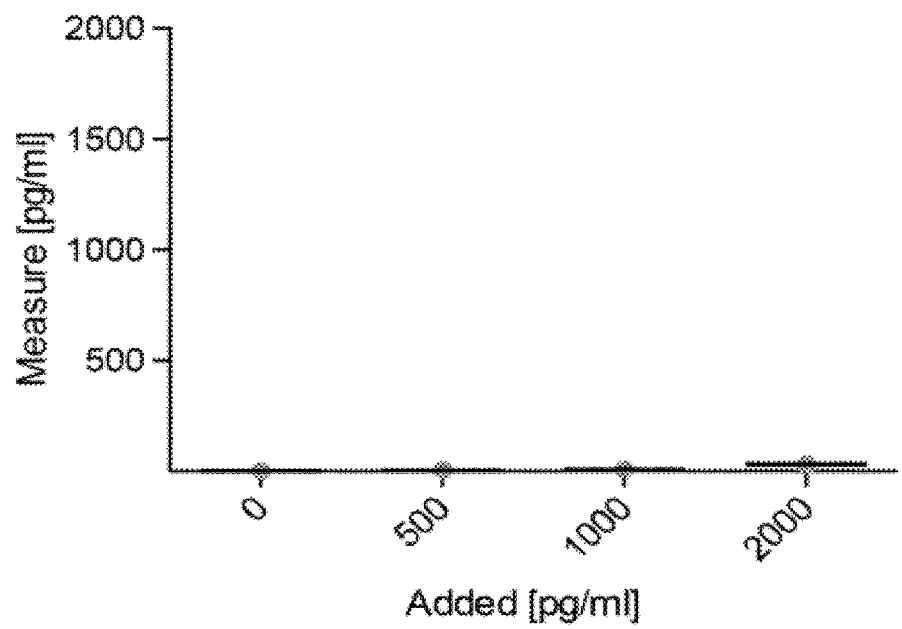
Figure 4C:
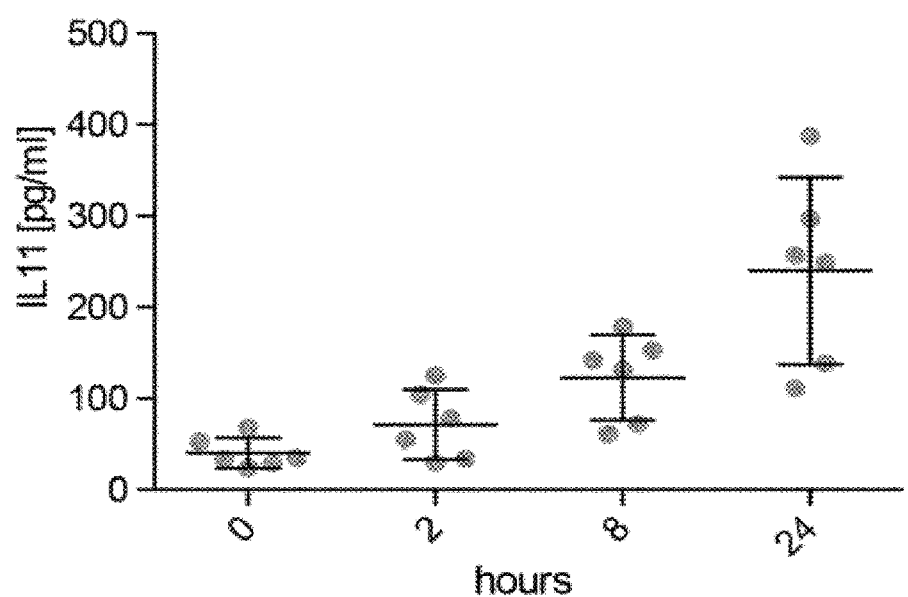

The results are shown in FIG. 4A. Each factor was found to significantly induce IL-11 secretion from fibroblasts. IL-11 is shown to act in an autocrine loop in fibroblasts, which can result in an upregulation of IL-11 protein as much as 100-fold after 72 hours (FIG. 4D).

Interestingly, this autocrine loop for IL-11 is similar to the autocrine production of IL-6. IL-6 is from the same cytokine family and also signals via the gp130 receptor (Garbers and Scheller, 2013 Biol Chem 394, 1145-1161), which is proposed to ensure the continued survival and growth of lung and breast cancer cells (Grivennikov and Karin, 2008 Cancer Cell 13, 7-9).

Figure 4D:
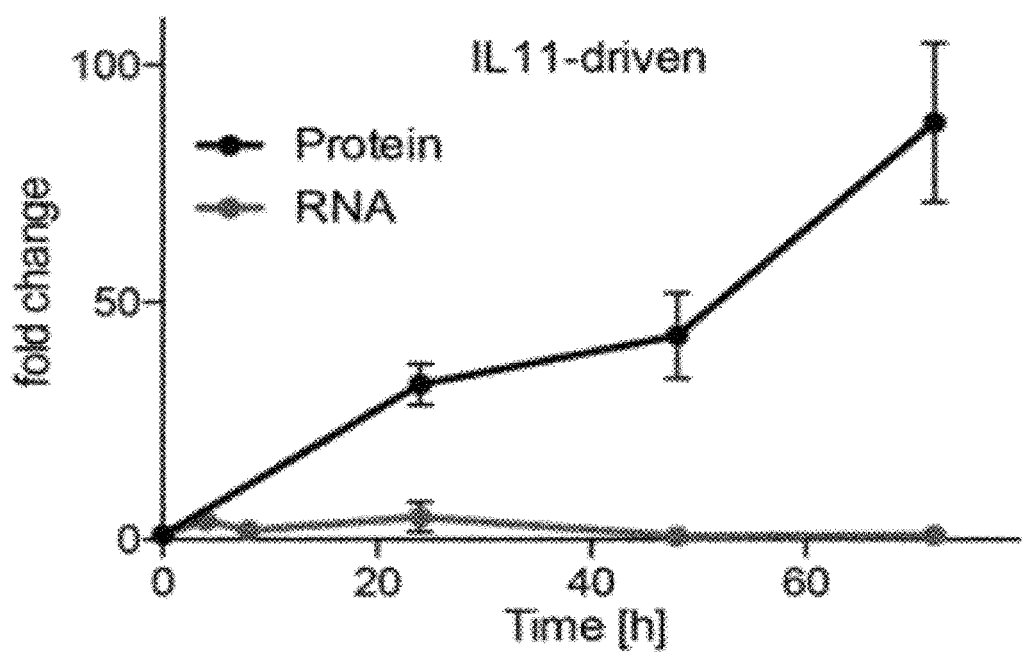

No increase in IL-11 RNA level was detected in response to stimulation with IL-11 (FIG. 4D). Unlike TGFβ1, which increases IL-11 expression at both the RNA and protein level, therefore IL-11 seems to upregulate IL-11 expression only at the post-transcriptional level.

1.2 IL-11 has a Profibrotic Role in Fibrosis of Heart Tissue

To explore whether the autocrine production of IL-11 is pro- or anti-fibrotic, fibroblasts were cultured in vitro with recombinant IL-11, and the fraction of myofibroblasts (αSMA-positive cells) and extracellular matrix production was analysed.

The expression of αSMA, collagen and periostin was monitored with the Operetta High-Content Imaging System in an automated, high-throughput fashion. In parallel, secretion of fibrosis marker proteins such as MMP2. TIMP1 and IL-6 was analysed by ELISA assays, and the levels of collagen were confirmed by calorimetric Sirius Red analysis of the cell culture supernatant.

Briefly, atrial fibroblasts derived from 3 individuals were incubated in 2 wells each for 24 h without stimulation, with TGFβ1 (5 ng/ml), or with IL-11 (5 ng/ml). Following incubation, cells were stained to analyse α-SMA content to estimate the fraction of myofibroblasts, and for collagen and periostin to estimate ECM production. Fluorescence was measured in 7 fields per well. The supernatant of 2 wells per individual was also assessed for collagen content by Sirius Red staining. The signal was normalized to the control group without stimulation. Secretion of the fibrosis markers IL-6, TIMP1 and MMP2 was analysed via ELISA.

Figure 5A:
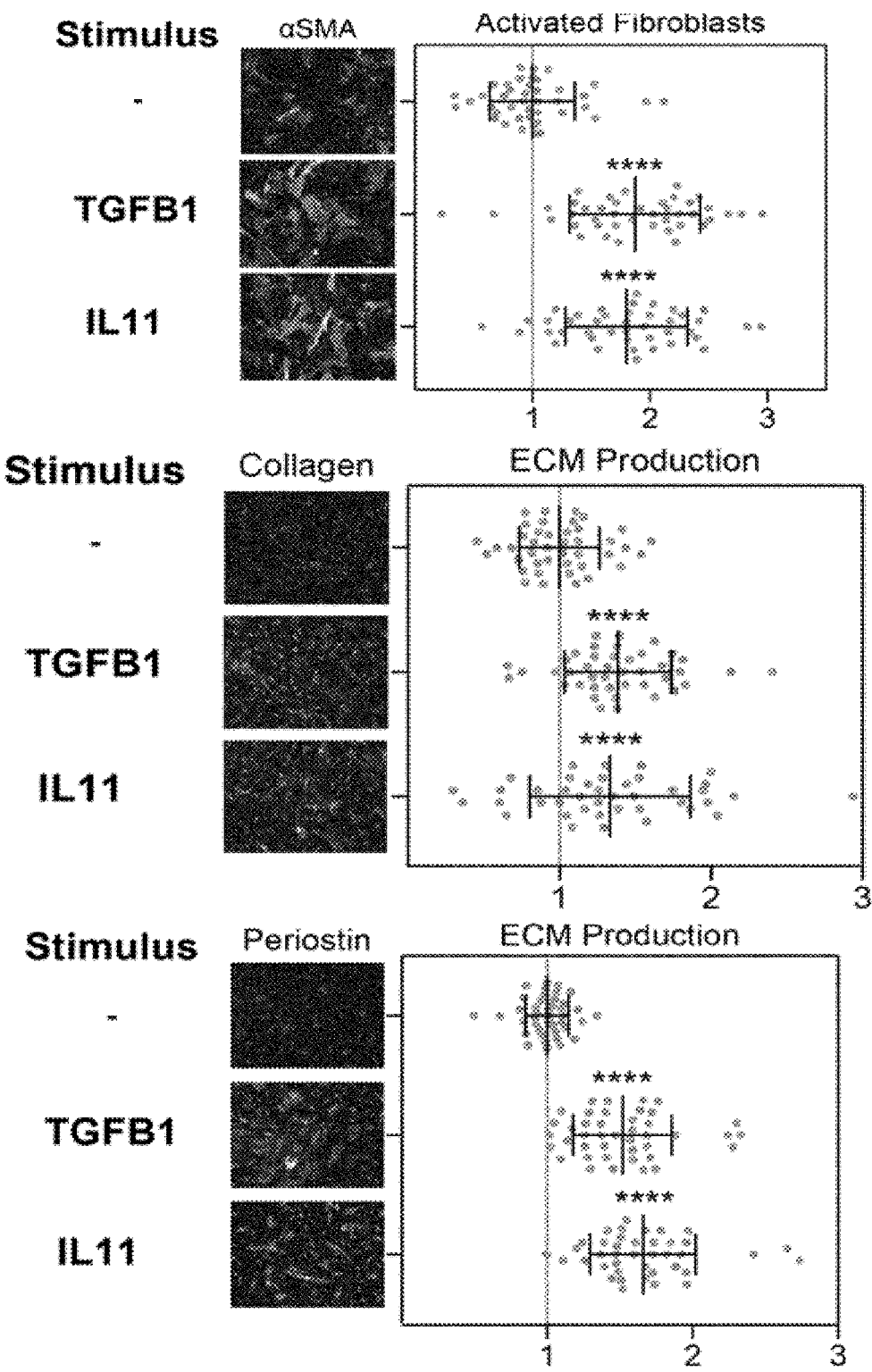
FIG. 5. Graphs and images showing myofibroblast generation from, and production of ECM and cytokine expression by, atrial fibroblasts in response to stimulation with TGFβ1 or IL-11. (A) myofibroblast generation and ECM production by primary atrial fibroblasts following stimulation with TGFβ1 or IL-11, as measured by fluorescence microscopy following staining for a α-SMA, collagen or periostin. (B) Collagen content of cell culture supernatant as determined by Sirius Red staining. Secretion of the fibrosis markers (C) IL-6, (D) TIMP1 and (E) MMP2 as measured by ELISA. (F) Activation of murine fibroblasts by stimulation with human or mouse recombinant IL-11. $*P<0.05$, $P<0.01$, $*P<0.001$, $****P<0.0001$ [Mean±SD, Dunnett].
Figure 5B:
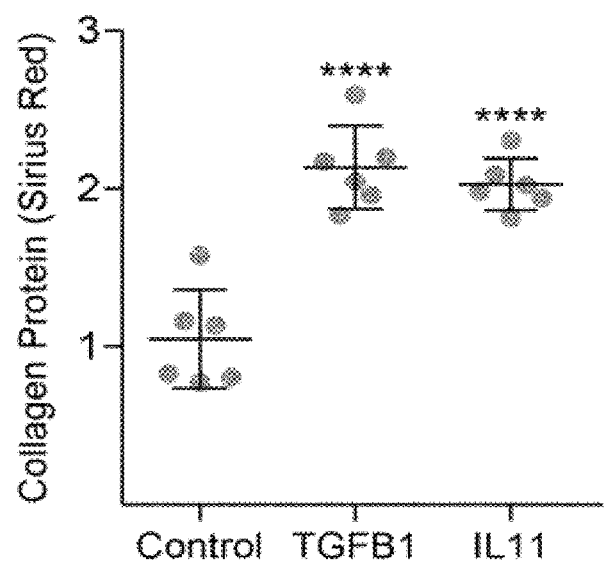
Figure 5C:
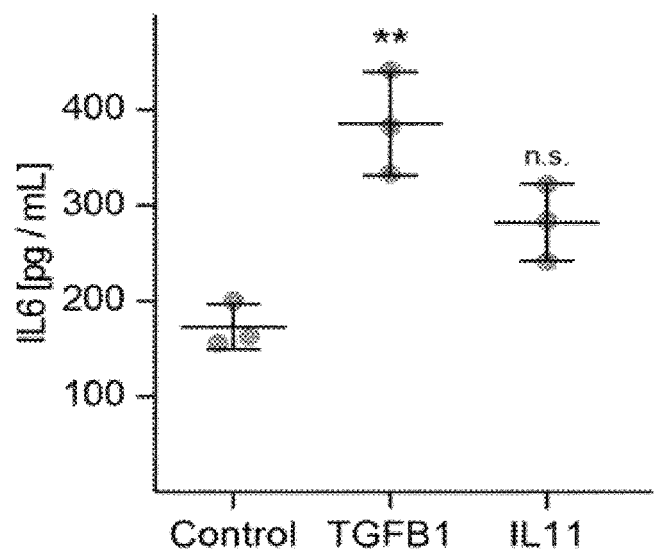
Figure 5D:
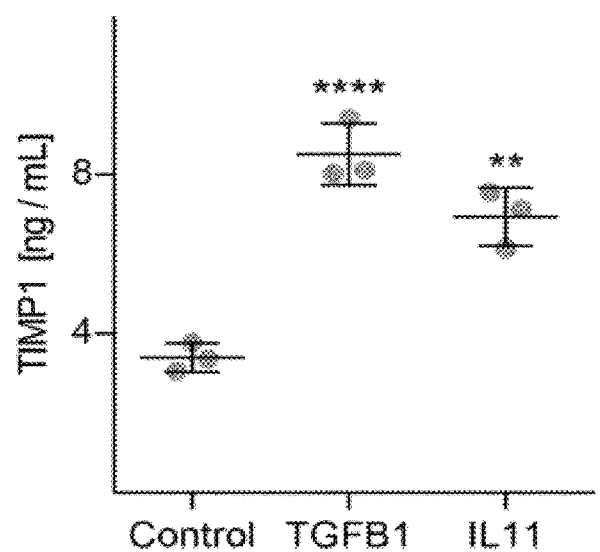
Figure 5E:
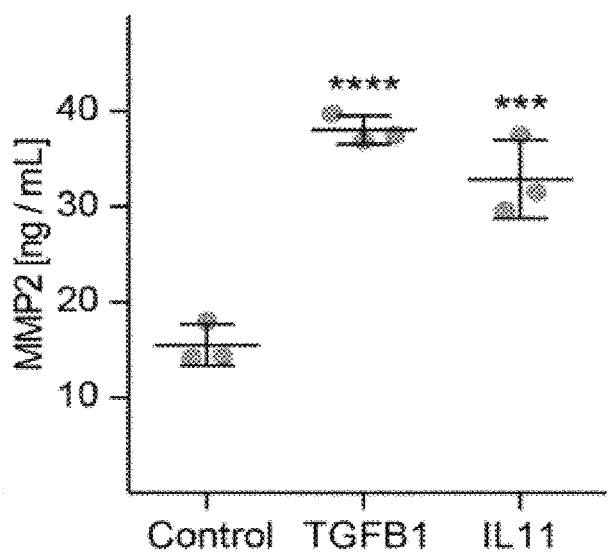

The results are shown in FIGS. 5A to 5F. TGFβ1 activated fibroblasts and increased ECM production (FIG. 5A). Unexpectedly, and in contrast with the anti-fibrotic role described for IL-11 in heart tissue in the scientific literature, recombinant IL-11 caused an increase in the fraction of myofibroblasts in fibroblast cultures, and also promoted the production of extracellular matrix proteins collagen and periostin to the same extent as TGFβ1 (FIG. 5A). Both of IL-11 and TGFβ1 cytokines also significantly increased the secretion of pro-fibrotic markers IL-6, TIMP1 and MMP2 (FIGS. 5B to 5E), and to a similar level.

The inventors hypothesized that the contradiction between the present finding that IL-11 is profibrotic in heart tissue and the antifibrotic role described in the literature might be related to the use of human IL-11 in rodents in those previous studies (Obana et al., 2010, 2012; Stangou et al., 2011; Trepicchio and Dorner, 1998).

Figure 5F:
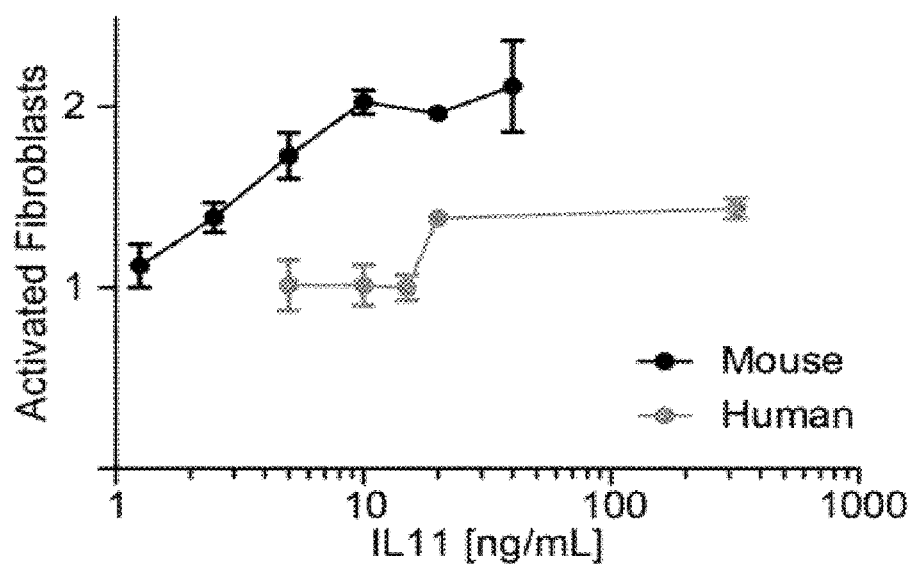

To investigate this hypothesis, serial dilutions of both human and mouse IL-11 were performed, and the activation of human atrial fibroblasts was monitored (FIG. 5F). No activation of fibroblasts was observed at low concentrations of human IL-11 on mouse cells, suggesting that previous insights into IL-11 function may in part be due to IL-11-non-specific observations.

1.3 IL-11 has a Profibrotic Role in Fibrosis of a Variety of Tissues

To test whether the profibrotic action of IL-11 was specific to atrial fibroblasts, human fibroblasts derived from several different tissues (heart, lung, skin, kidney and liver)

were cultured in vitro, stimulated with human IL-11, and fibroblast activation and ECM production was analysed as described above. Increased fibroblast activation and production of ECM was observed as compared to non-stimulated cultures in fibroblasts derived from each of the tissues analysed.

1.3.1 Liver Fibrosis

To test whether IL-11 signalling is important in liver fibrosis, human primary liver fibroblasts (Cell Biologics, Cat #: H-6019) were cultured at low passage in wells of 96-well plates and either not stimulated, stimulated with TGFβ1 (5 ng/ml, 24 h), IL-11 (5 ng/ml, 24 h) or incubated with both TGFβ1 (5 ng/ml) and a neutralising IL-11 antibody (2 µg/ml), or TGFβ1 (5 ng/ml) and an Isotype control antibody. Fibroblast activation (αSMA positive cells), cell proliferation (EdU positive cells) and ECM production (periostin and collagen) was analysed using the Operetta platform.

The results of the experiments with primary human liver fibroblasts are shown in FIGS. 22A to 22D. IL-11 was found to activate liver fibroblasts, and IL-11 signalling was found to be necessary for the profibrotic action of TGFβ1 in liver fibroblasts. Both activation and proliferation of fibroblasts was inhibited by neutralising anti-IL-11 antibody.

1.3.2 Skin Fibrosis

To test whether IL-11 signalling is important in skin fibrosis, primary mouse skin fibroblasts were cultured at low passage in wells of 96-well plates and either not stimulated, stimulated with TGFβ1 (5 ng/ml, 24 h) or incubated for 24 h with both TGFβ1 (5 ng/ml) and a neutralising IL-11 antibody (2 µg/ml). Fibroblast activation (αSMA positive cells) was then analysed using the Operetta platform.

Figure 23:
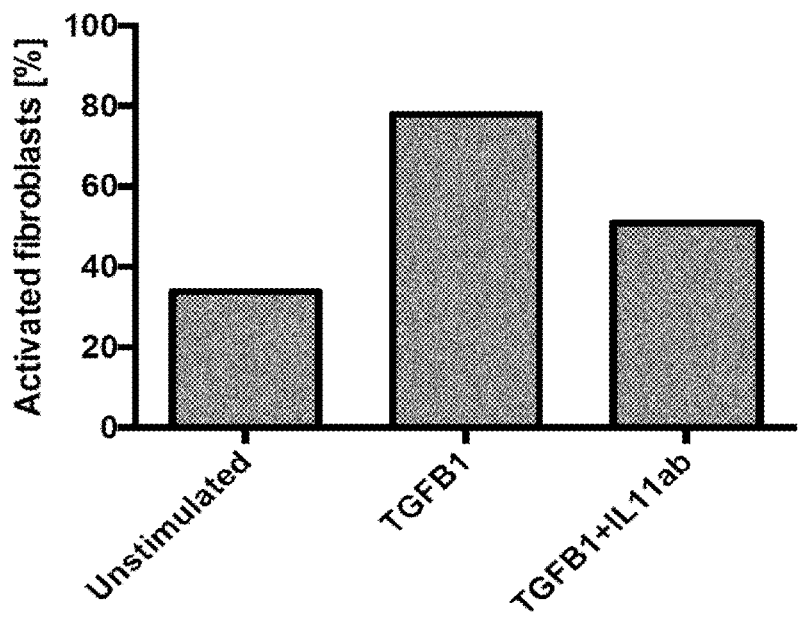
FIG. 23. Bar chart showing that IL-11 is required for the pro-fibrotic effects of TGFβ1 in skin fibroblasts. Activation of mouse skin fibroblasts, with or without stimulation with TGFβ1, and in the presence/absence of neutralising anti-IL-11 antibody, as measured by analysis of the percentage of α-SMA positive cells (activated fibroblasts).

The results are shown in FIG. 23. TGFβ1-mediated activation of skin fibroblasts was inhibited by neutralising anti-IL-11 antibody.

1.3.3 Fibrosis in Multiple Organs

Next, mouse recombinant IL-11 was injected (100 µg/kg, 3 days/week, 28 days) into mice to test whether IL-11 can drive global tissue fibrosis in vivo.

Figure 6A:
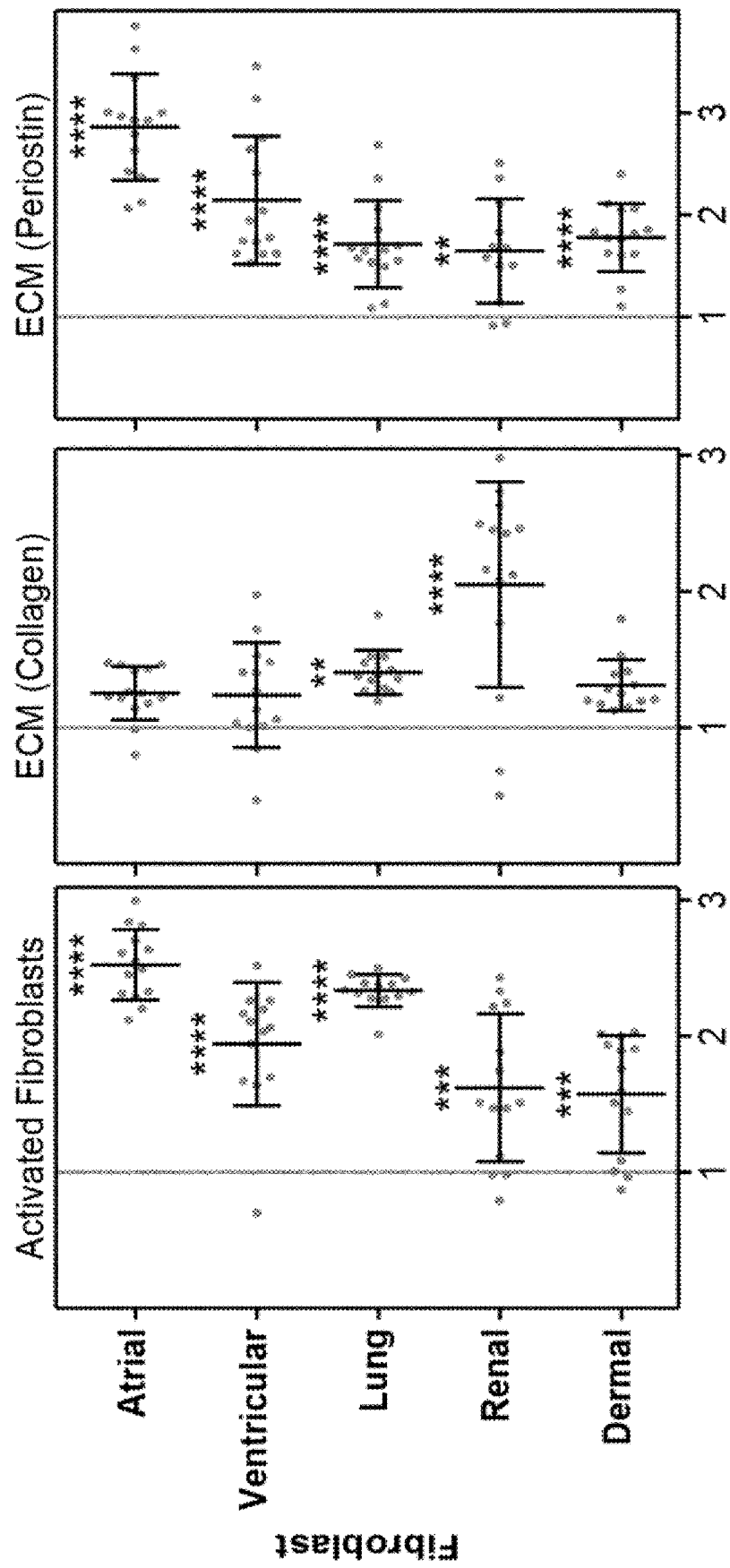
FIG. 6. Graphs showing the profibrotic effect of IL-11. (A) Mouse fibroblasts from different tissues of origin can be activated by IL-11 and display increased ECM production. [Mean±SD, Dunnett]. Injection of mice with recombinant IL-11 or AngII results in (B) an increase in organ weight [Mean±SEM], and (C) an increase in collagen content (as determined by HPA assay). $*P<0.05$, $P<0.01$, $*P<0.001$, $****P<0.0001$ [Mean±SD, Dunnett].
Figure 6B:
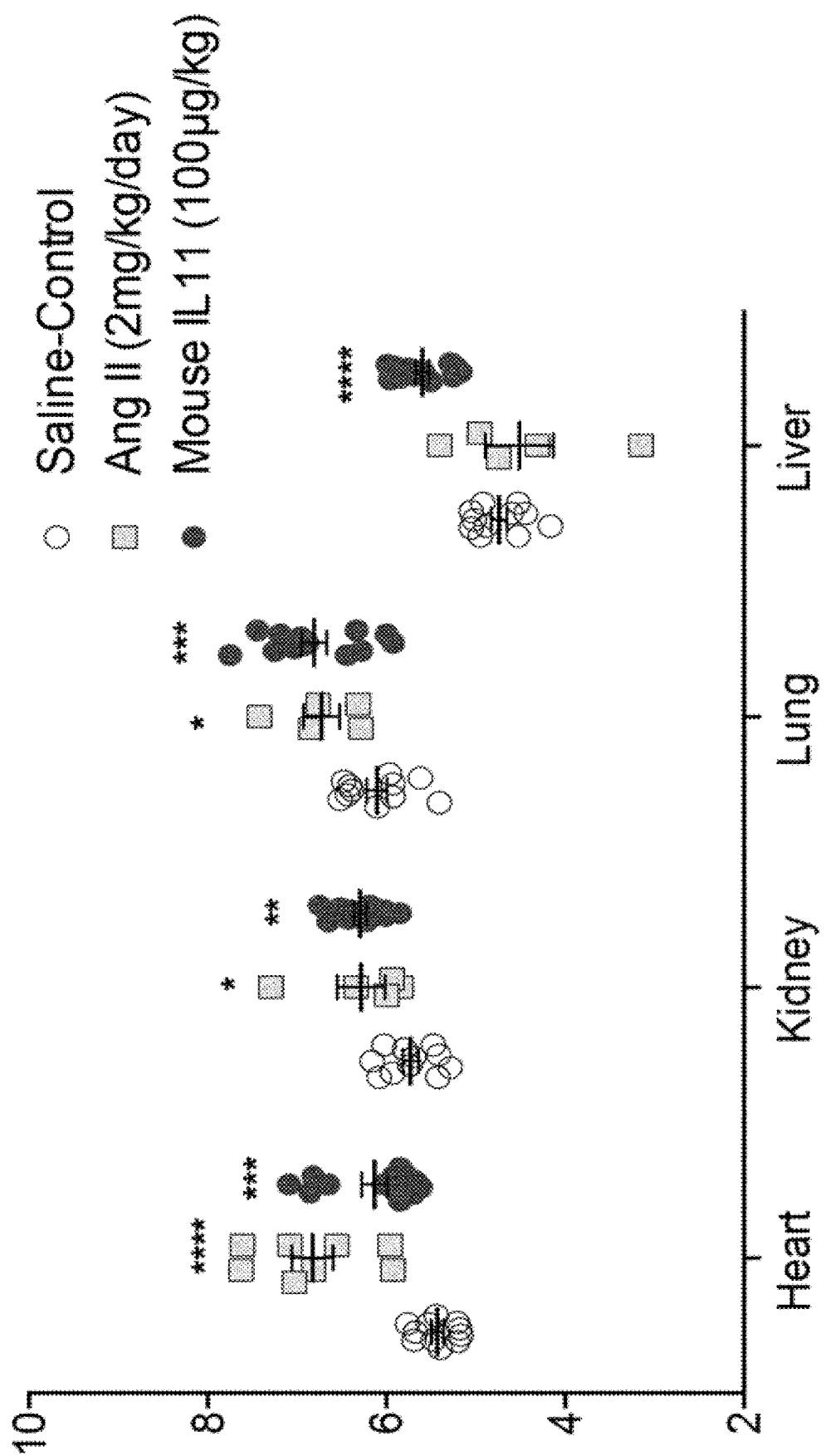
Figure 6C:
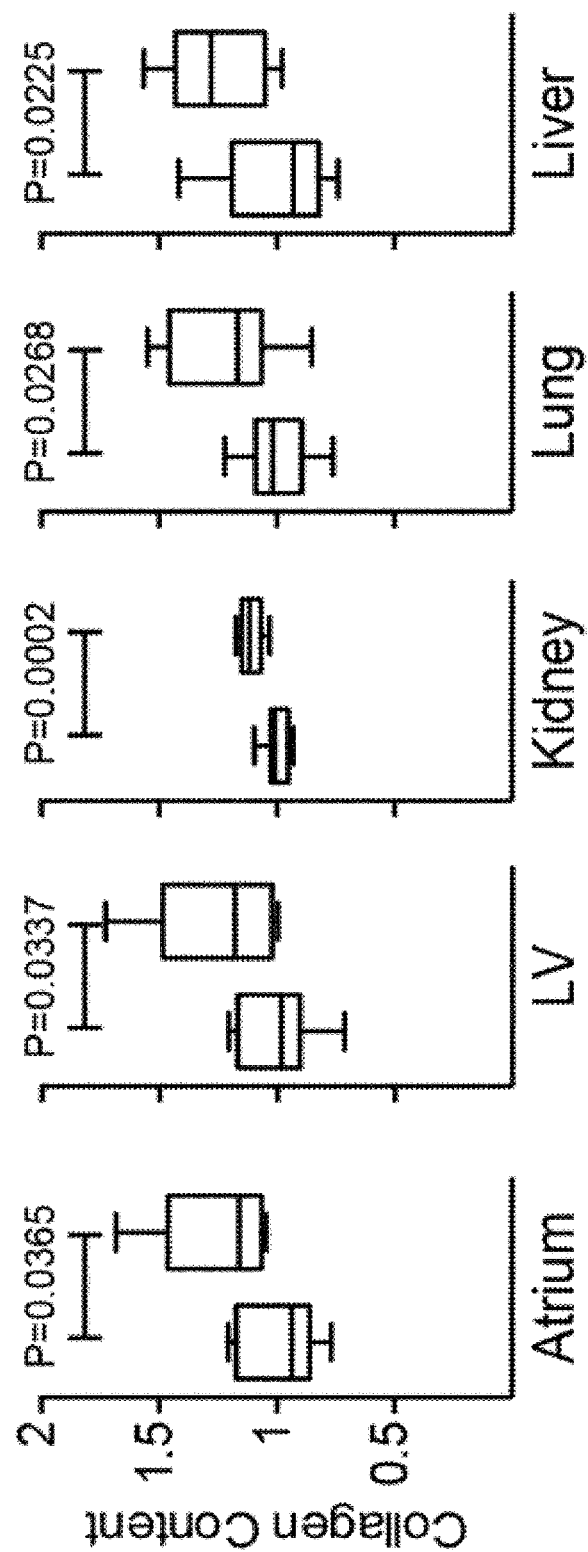
Figure 7A:
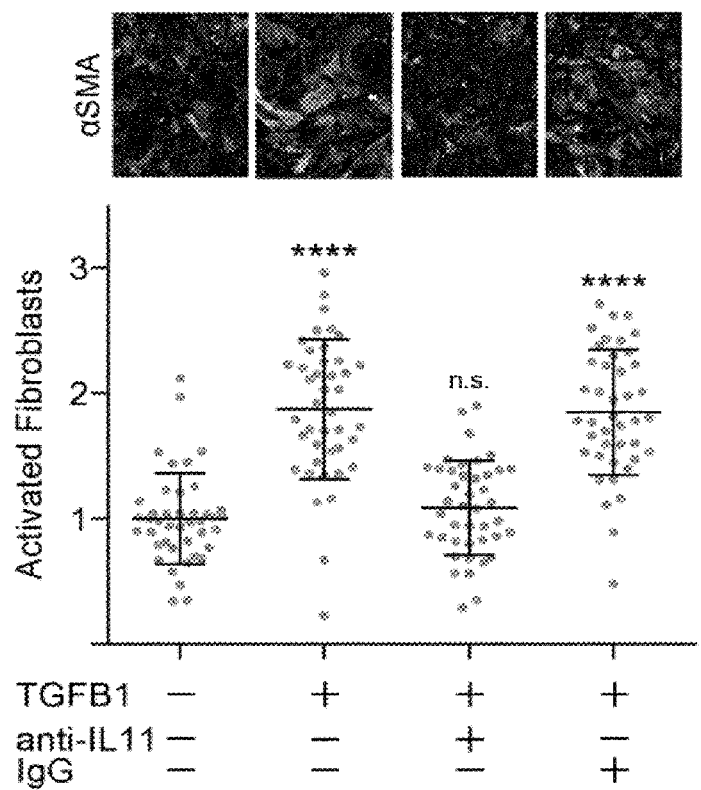
FIG. 7. Graphs and images showing that IL-11 is required the pro-fibrotic effects of TGFβ1 on fibroblasts. (A) myofibroblast generation and ECM production by primary atrial fibroblasts, with or without stimulation with TGFβ1, and in the presence/absence of neutralising anti-IL-11 antibody or isotype control IgG, as measured by fluorescence microscopy following staining for (A) α-SMA, (B) EdU or (C) Periostin. (D to F) Secretion of the fibrosis markers (D) IL-6, (E) TIMP1, and (F) MMP2 was analysed by ELISA. Fluorescence was normalized to the control group without stimulation. [Mean±SD, Dunnett] $*P<0.05$, $P<0.01$, $*P<0.001$ or $****P<0.0001$.
Figure 7B:
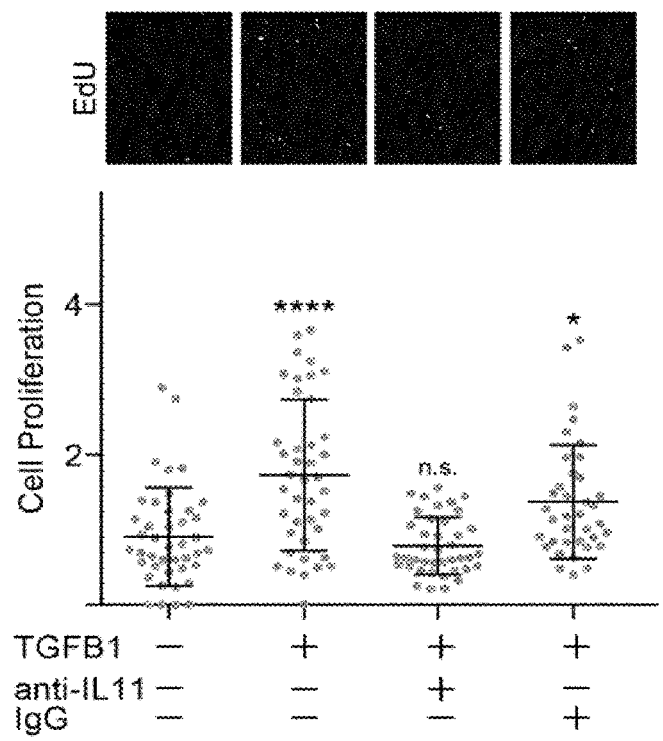
Figure 7C:
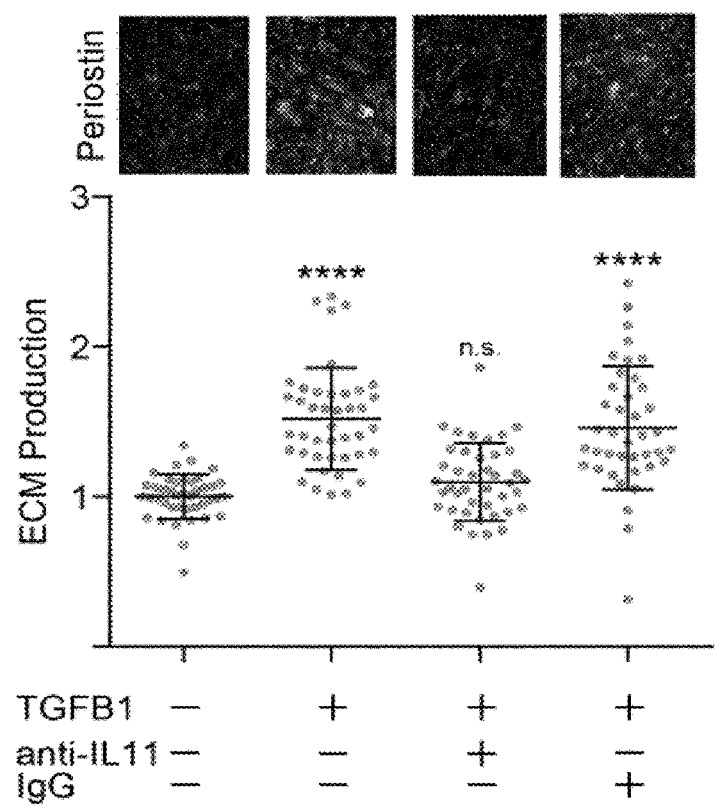
Figure 7D:
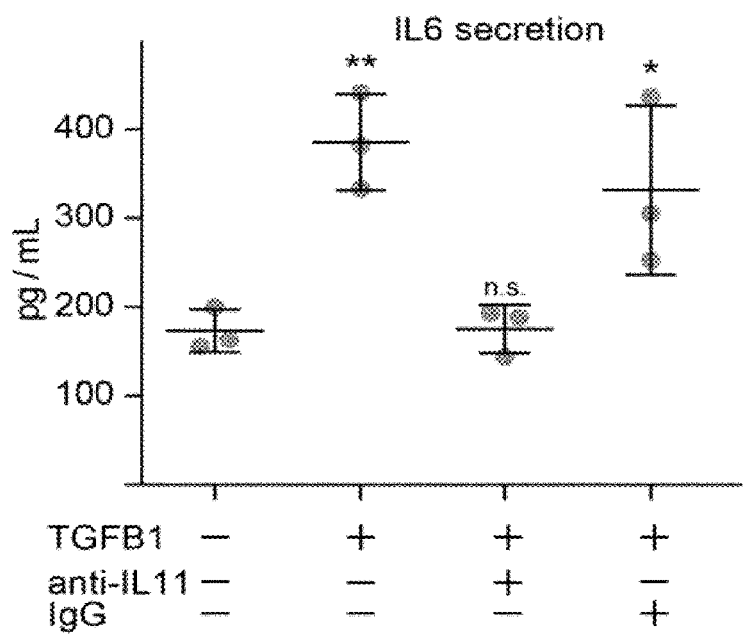
Figure 7E:
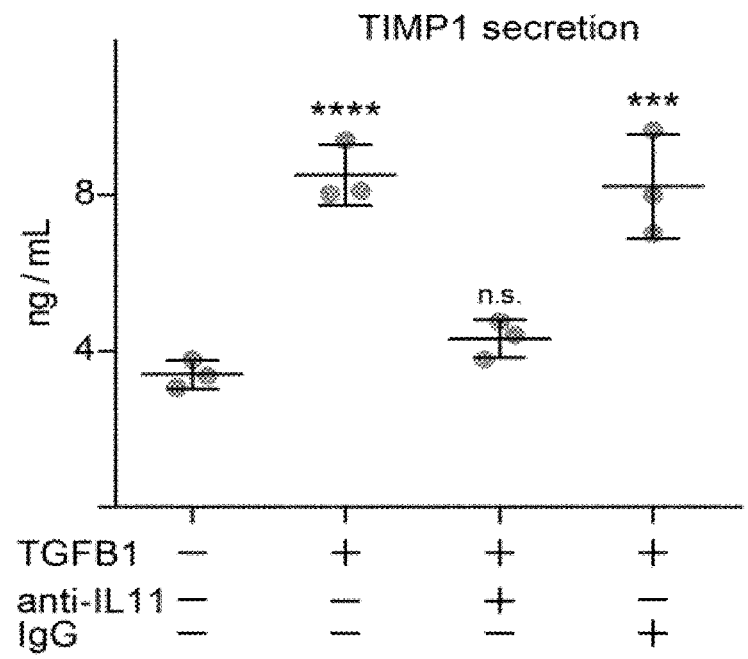
Figure 7F:
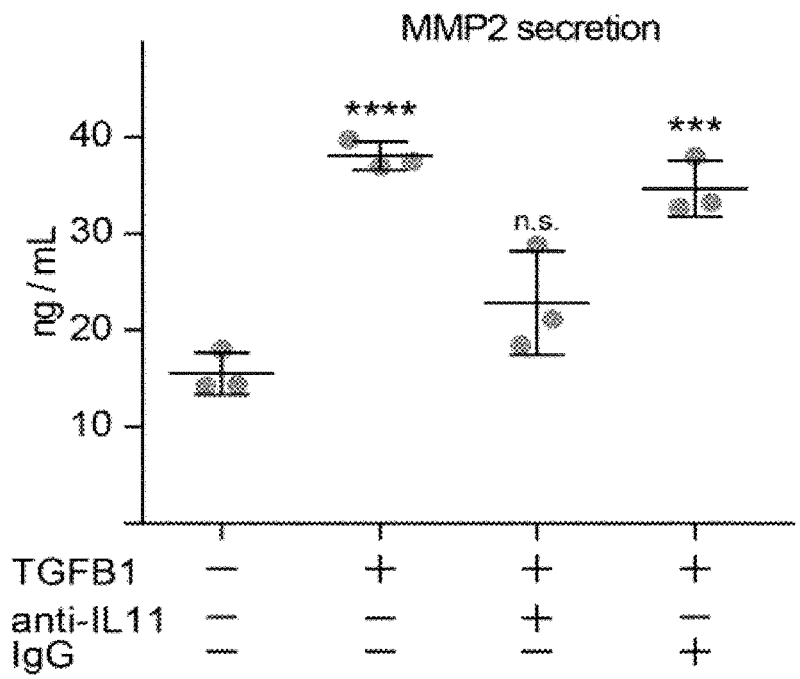

The results are shown in FIG. 6. Compared to injection of AngII (a cytokine that causes an elevation in blood pressure and hypertrophy of the heart), IL-11 also increased the heart weight but also kidney, lung and liver weight indexed to body weight (FIG. 6B). Assessing collagen content in these issues by hydroxyproline assay revealed an upregulation of collagen production in these tissues, indicating fibrosis as the likely cause for the increase in organ weight (FIG. 6C). Expression of fibrosis marker genes ACTA2 (=αSMA), Col1a1, Col3a1, Fn1, Mmp2 and Timp1 was also detected by qPCR analysis of RNA isolated from heart, kidney, lung and liver tissues of these animals Example 2: Therapeutic Potential of IL-11/IL-11R Antagonism 2.1 Inhibition of the Fibrotic Response Using Neutralising Antagonists of IL-11/IL-11R Next it was investigated whether the autocrine loop of IL-11 secretion was required for the pro-fibrotic effect of TGFβ1 on fibroblasts.

IL-11 was inhibited using a commercially available neutralizing antibody (Monoclonal Mouse IgG2A; Clone #22626; Catalog No. MAB218; R&D Systems, MN, USA). Fibroblasts were treated with TGFβ1 in the presence or absence of the antibody, and fibroblast activation, the proportion of proliferating cells and ECM production and markers of the fibrotic response were measured.

Briefly, atrial fibroblasts derived from 3 individuals were incubated for 24 h with TGFβ1 (5 ng/ml) or TGFβ1 in the presence of neutralising anti-IL-11 antibody or isotype control antibody. Following incubation, cells were stained for αSMA to determine the fraction of myofibroblasts, the proportion of proliferating cells was determined by analysing the cells for EdU incorporation, and periostin was measured to determine ECM production. Fluorescence was measured with the Operetta platform for 14 fields across 2 wells for each individual. Secretion of the fibrosis markers IL-6, TIMP1 and MMP2 was also analysed by ELISA. Fluorescence was normalized to the control group without stimulation.

The results are shown in FIGS. 7A to 7F. IL-11 inhibition was found to ameliorate TGFβ1-induced fibrosis, and it was shown that IL-11 is essential for the pro-fibrotic effect of TGFβ1. Inhibition of IL-11 was found to 'rescue' the TGFβ1 phenotype at the protein level.

Collagen production was also analysed. Cardiac fibroblasts derived from 3 individuals were incubated for 24 h with TGFβ1 (5 ng/ml) or TGFβ1 and a neutralizing IL-11 antibody. Following incubation the cells were stained for collagen using the Operetta assay and florescence was quantified as described above. Secreted collagen levels in the cell culture supernatant were assessed by Sirius Red staining.

Figure 8A:
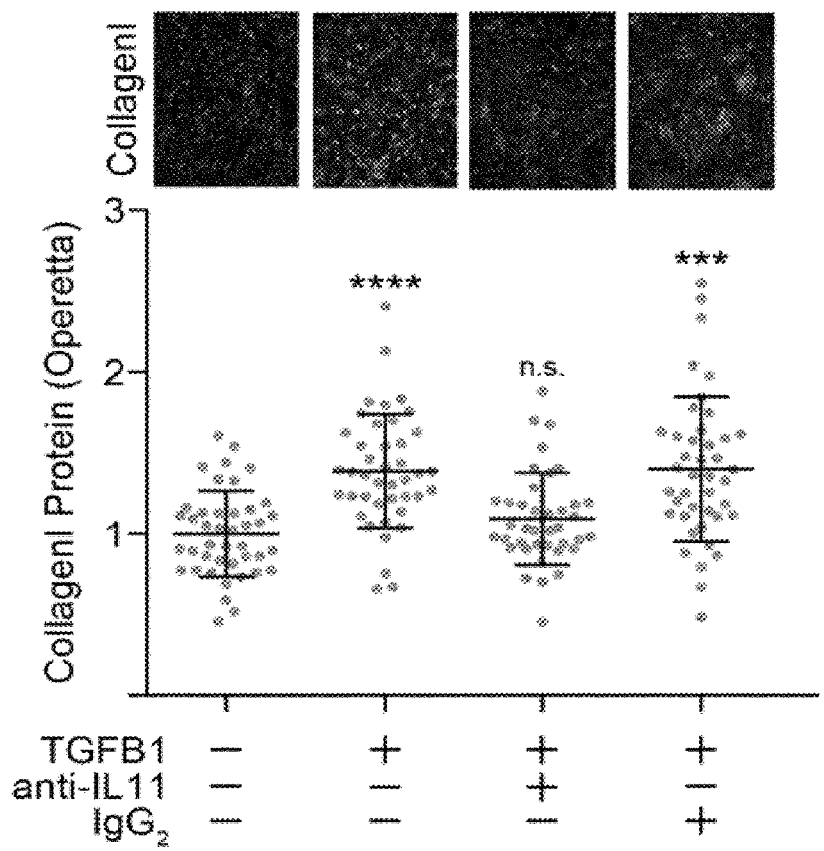
FIG. 8. Graphs and images showing the effect of neutralisation of IL-11 on collagen production triggered by TGFβ1. Collagen production by cardiac fibroblasts with or without stimulation with TGFβ1, and in the presence/absence of neutralising anti-IL-11 antibody or isotype control IgG, as determined by (A) Operetta assay or (B) Sirius Red staining. [Mean±SD, Dunnett] $*P<0.05$, $P<0.01$, $*P<0.001$ or $****P<0.0001$.
Figure 8B:
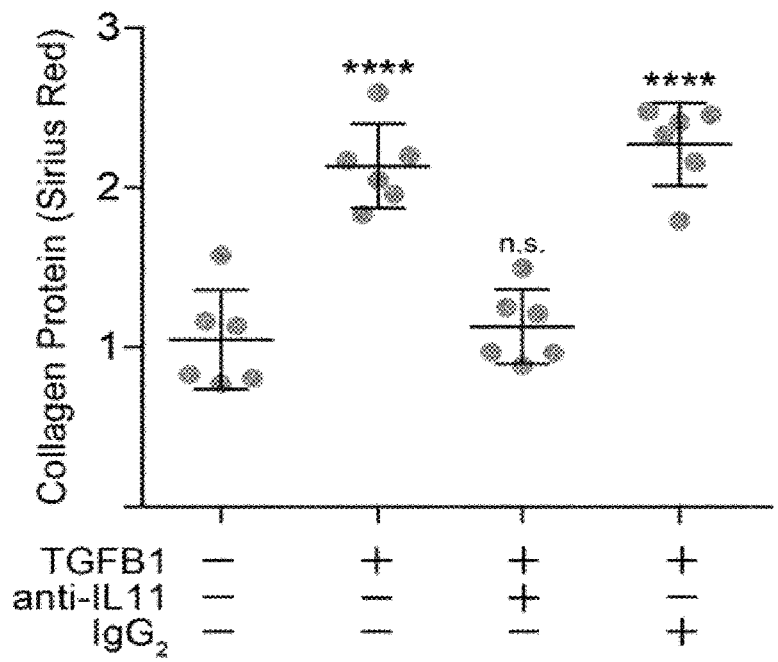

The results are shown in FIGS. 8A and 8B, and confirm the anti-fibrotic effect of inhibition of IL-11 using a neutralising antibody.

Next, the ability of several other IL-11/IL-11R antagonists to inhibit fibrosis was analysed in vitro using the atrial fibroblast, TGFβ1-induced myofibroblast transition assay described herein above.

Briefly, human atrial fibroblasts cells were cultured in vitro, stimulated for 24 h with TGFβ1 (5 ng/ml) or left unstimulated, in the presence/absence of: (i) neutralising anti-IL-11 antibody, (ii) neutralising anti-IL-11RA antibody, (iii) treatment with siRNA directed against IL-11 or (iv) treatment with siRNA directed against IL-11RA. The proportion of activated fibroblasts (myofibroblasts) was analysed by evaluating αSMA content as described above.

Figure 9:
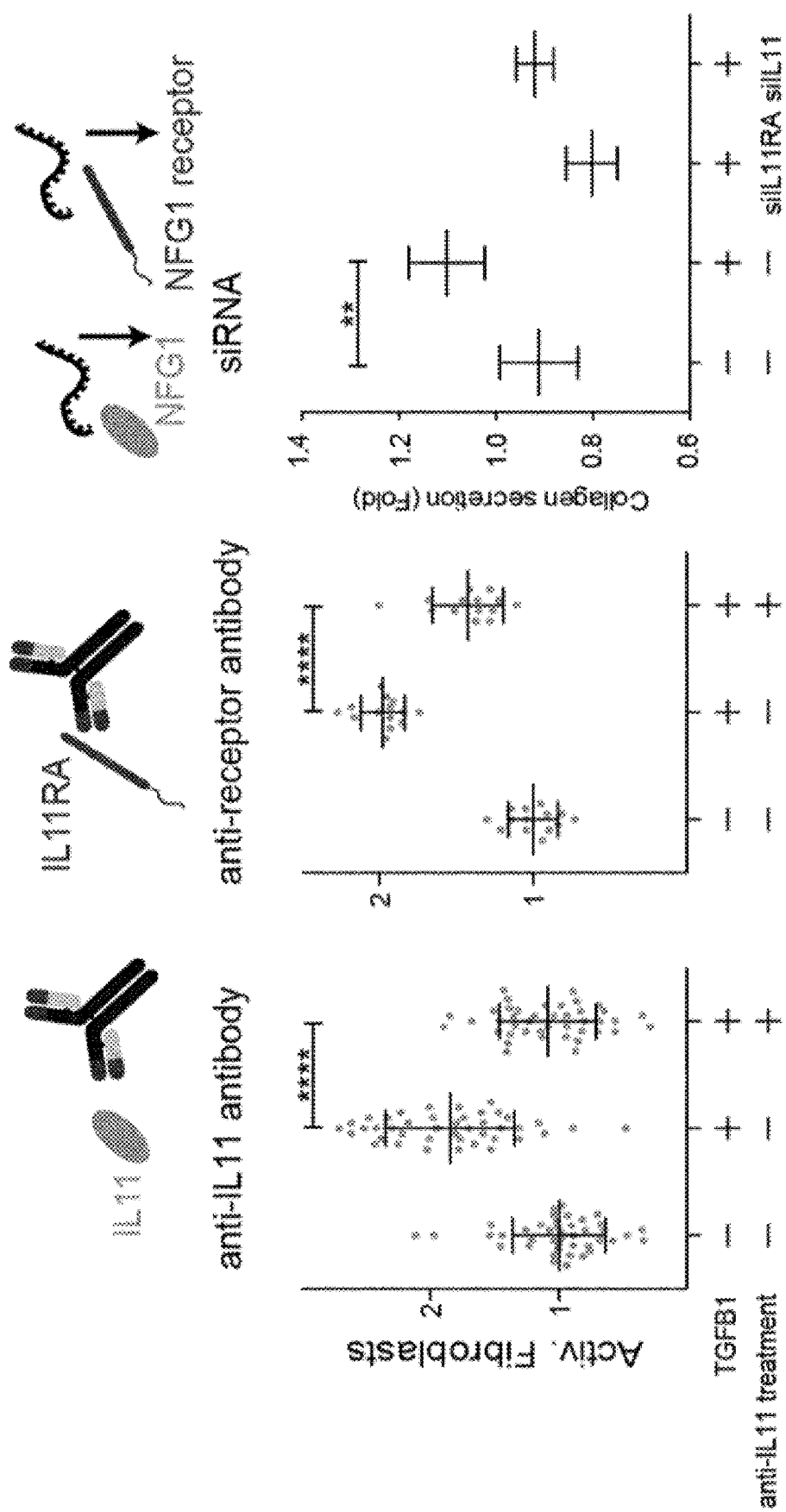
FIG. 9. Graphs showing the ability of various IL-11 and IL-11Rα antagonists to inhibit fibrosis. Human atrial fibroblasts were treated with neutralizing antibody against IL-11, neutralizing antibody against IL-11Rα, siRNA that downregulates IL-11 expression or siRNA that downregulates IL-11RA expression and the effect on the TGFβ1-driven pro-fibrotic response in fibroblasts in vitro was analysed. [Mean±SD, Dunnett] $*P<0.05$, $P<0.01$, $*P<0.001$ or $****P<0.0001$.
Figure 10A:
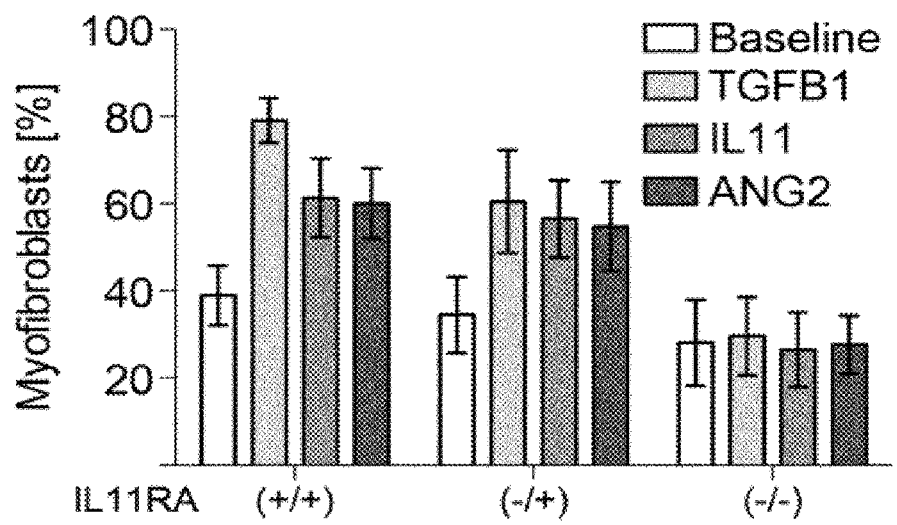
FIG. 10. Bar charts showing the response of fibroblasts from IL-11-RA knockout mice to pro-fibrotic treatment. Fibroblasts derived from IL-11RA WT (+1+), Heterozygous (+/−) and Homozygous null (−/−) mice were incubated for 24 h with TGFβ1, IL-11 or AngII (5 ng/ml). (A) Percentage of myofibroblasts as determined by analysis αSMA content, (B) Percentage proliferating cells as determined by staining for EdU, (C) Collagen content and (D) ECM production as measured by detection of periostin [Mean±SD].
Figure 10B:
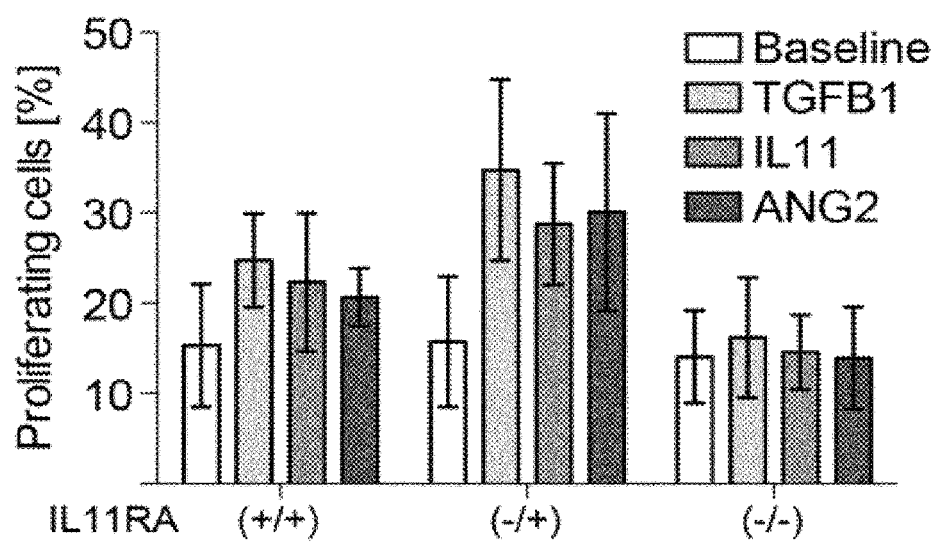
Figure 10C:
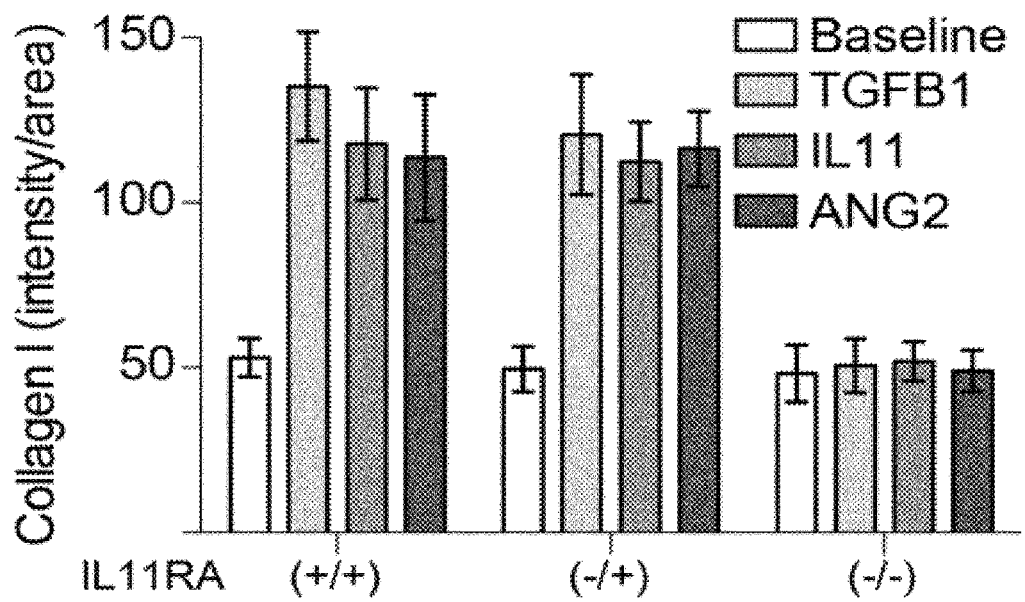
Figure 10D:
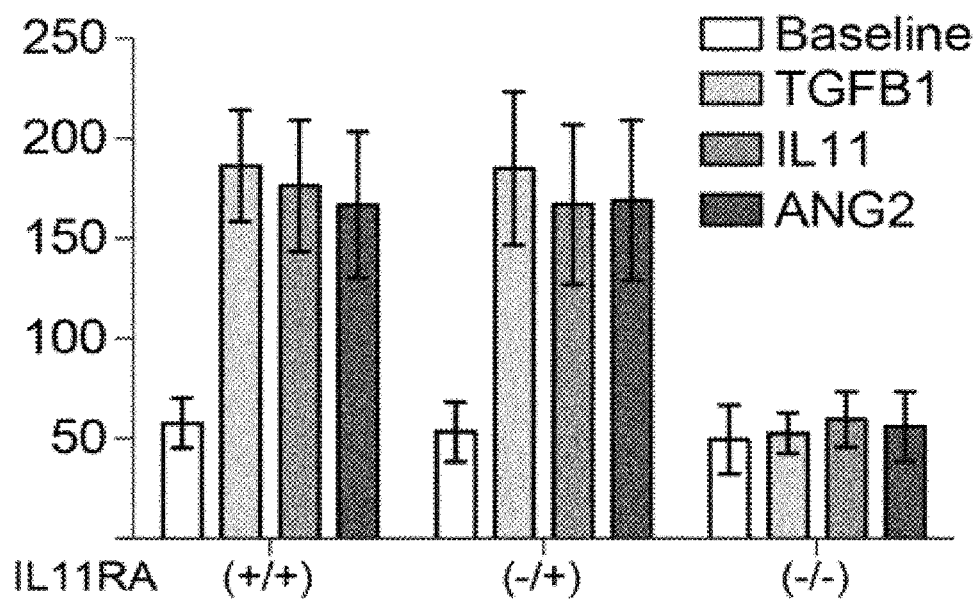

The results are shown in FIG. 9. Each of the antagonists of IL-11/IL-11R signalling was found to be able to abrogate TGFβ1-mediated profibrotic response.

Example 3: In Vivo Confirmation of a Profibrotic Role for IL-11/IL-11R Signalling 3.1 In Vitro Studies Using Cells Derived from IL-11RA Gene Knock-Out Mice All mice were bred and housed in the same room and provided food and water ad libitum. Mice lacking functional alleles for IL-11Rα (IL-11RA1 KO mice) were on C57Bl/6 genetic background. Mice were of 9-11 weeks of age and the weight of animals did not differ significantly.

To further confirm the anti-fibrotic effect of inhibition of IL-11 signalling, primary fibroblasts were generated from IL-11RA gene knock-out mice and incubated with primary fibroblast cells harvested from IL-11RA+/+ (i.e. wildtype), IL-11RA+/− (i.e. heterozygous knockout) and IL-11RA−/− (i.e. homozygous knockout) animals with TGFβ1, IL-11 or AngII. Activation and proliferation of fibroblasts and ECM production was analysed.

Fibroblasts derived from IL-11RA+/+, IL-11RA+/− and IL-11RA−/− mice were incubated for 24 hours with TGFβ1, IL-11 or AngII (5 ng/ml). Following incubation, cells were stained for αSMA content to estimate the fraction of myofibroblasts, for EdU to identify the fraction of proliferating cells, and for collagen and periostin to estimate ECM production. Fluorescence was measured using the Operetta platform.

The results are shown in FIGS. 10A to 10D. IL-11RA−/− mice were found not to respond to pro-fibrotic stimuli. These results suggested that IL-11 signalling is also required for AngII-induced fibrosis.

Next, it was investigated whether this was also true for other pro-fibrotic cytokines.

Briefly, fibroblasts were cultured in vitro in the presence/absence of various different pro-fibrotic factors (ANG2, ET-1 or PDGF), and in the presence/absence of neutralising anti-IL-11 antibody or pan anti-TGFβ antibody. After 24 hours, collagen production by the cells was determined by analysis using the Operetta system as described above, and myofibroblast generation was determined by analysis of αSMA expression as described above.

Figure 11A:
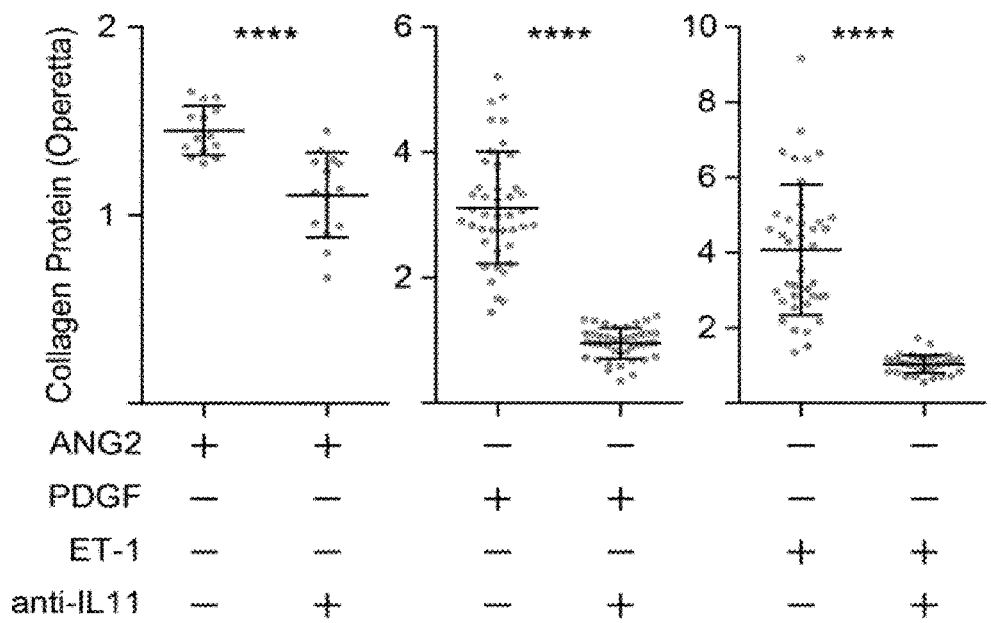
FIG. 11. Graphs showing the effect of IL-11 neutralisation on fibrosis in response to various pro-fibrotic stimuli. Fibroblasts were cultured in vitro in the presence/absence of various different pro-fibrotic factors, and in the presence/absence of neutralising anti-IL-11 antibody or pan anti-TGFβ antibody (A) Collagen production and (B) myofibroblast generation as determined by analysis of αSMA expression. [Mean±SD, Dunnett] *P<0.05, P<0.01, *P<0.001 or ****P<0.0001.
Figure 11B:
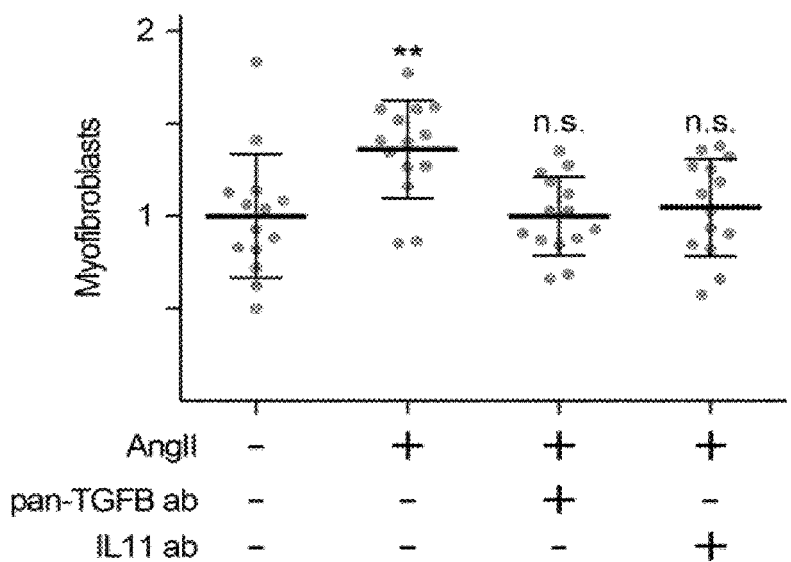
Figure 12A:
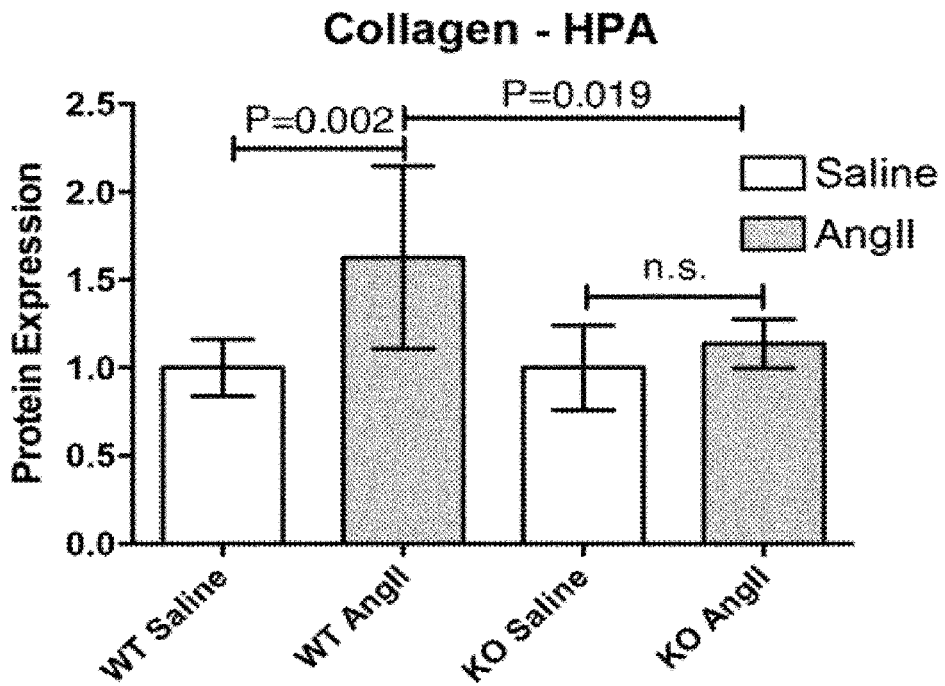
FIG. 12. Bar charts showing expression of markers of fibrosis in the atrium and heart of WT and IL-11RA (−/−) animals following treatment with AngII treatment. (A) Collagen content, as measured by hydroxyproline assay. (B) Collagen (Col1A2) expression. (C) αSMA (ACTA2) expression. (D) Fibronectin (Fn1) expression.
Figure 12B:
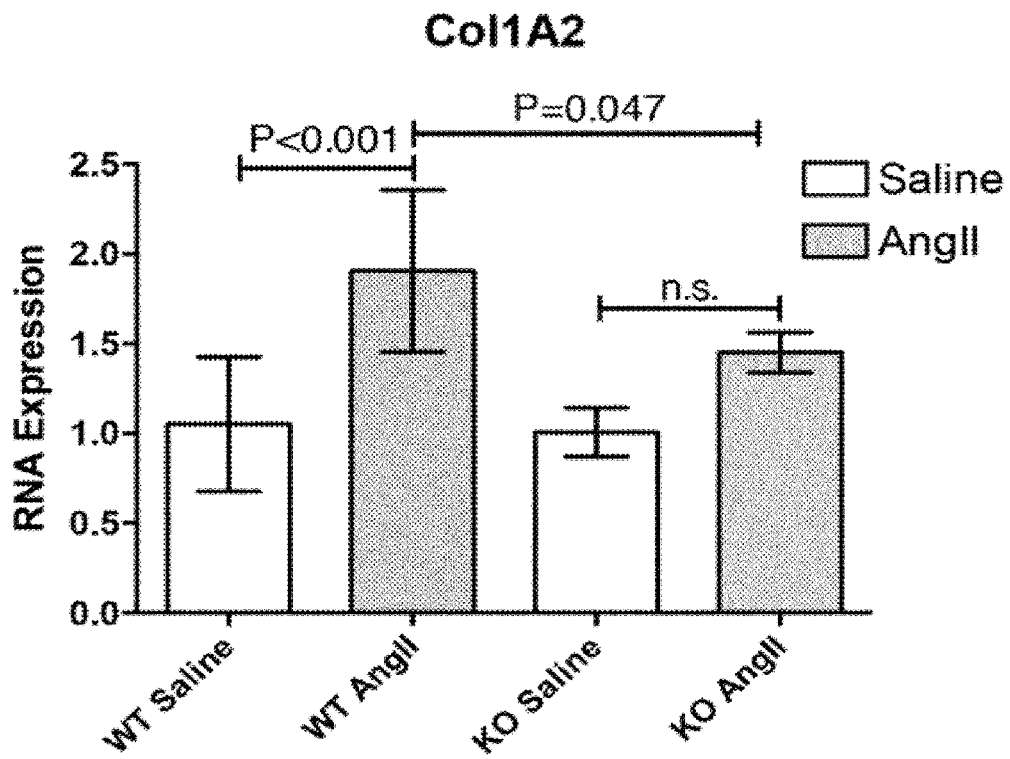
Figure 12C:
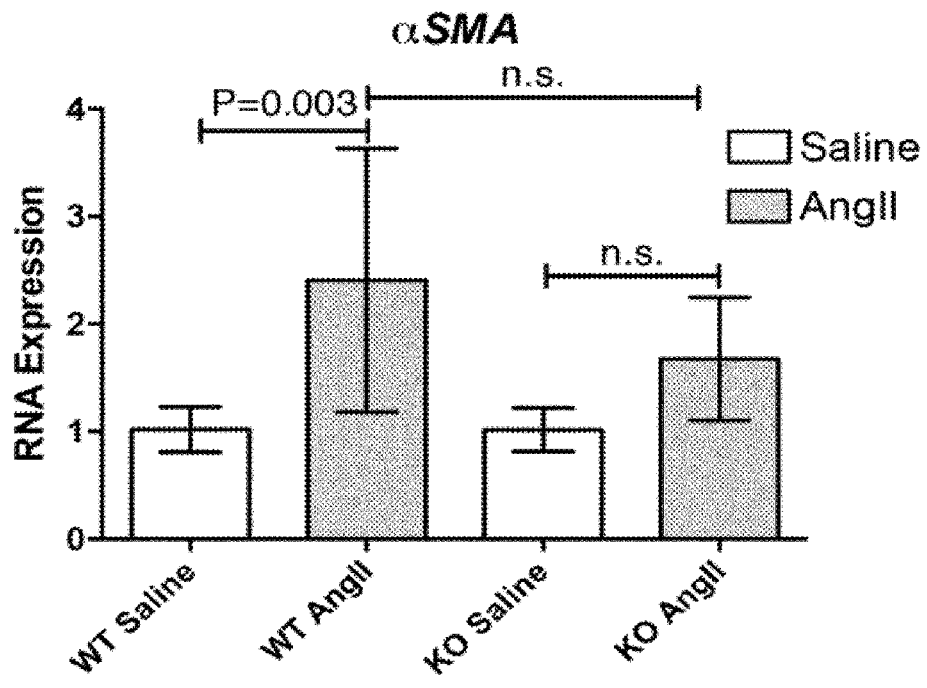
Figure 12D:
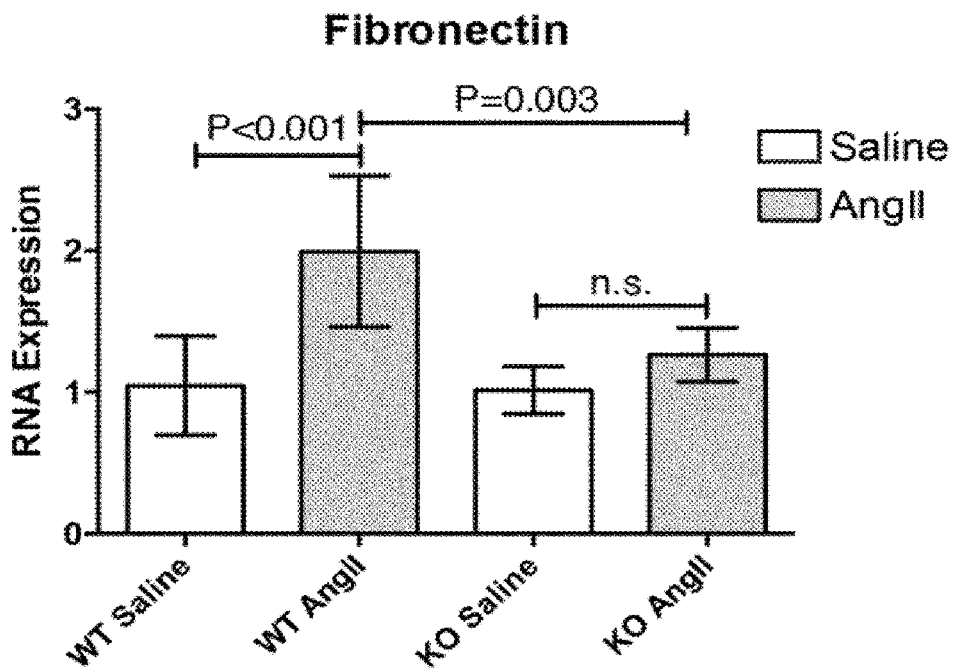

The results are shown in FIGS. 11A and 11B. IL-11 was found to be required for fibrosis downstream of various profibrotic stimuli, and was thus identified as a central mediator of fibrosis induced by a variety of different profibrotic factors.

In a further experiment, the role of IL-11 signalling was investigated in lung fibrosis, using an in vitro scratch assay of migration of lung fibroblasts. In response to pro-fibrotic stimuli, fibroblasts are activated and migrate within the fibrotic niche in the body. The migration rate of cells is a measure of cell-cell and cell-matrix interactions and a model for wound healing in vivo (Liang et al., 2007; Nat Protoc. 2(2):329-33).

Fibroblasts derived from lung tissue from both wild type (WT) and also homozygous IL-11RA (−/−) knockout mice were grown at low passage on a plastic surface until they formed a uniform cell monolayer. A scratch was then created in the cell layer, and cell migration close to the scratch was monitored, either in the absence of stimulation, or in the presence of TGFβ1 or IL-11. Images captured at images at the two time points of immediately after creating the scratch and at 24 h were used to determine the area covered by cells, and the rate of migration was compared between WT and KO fibroblasts. Cell migration (area in the scratch covered by cells after 24 h) was normalized to the migration rate of WT cells without stimulus.

Figure 24:
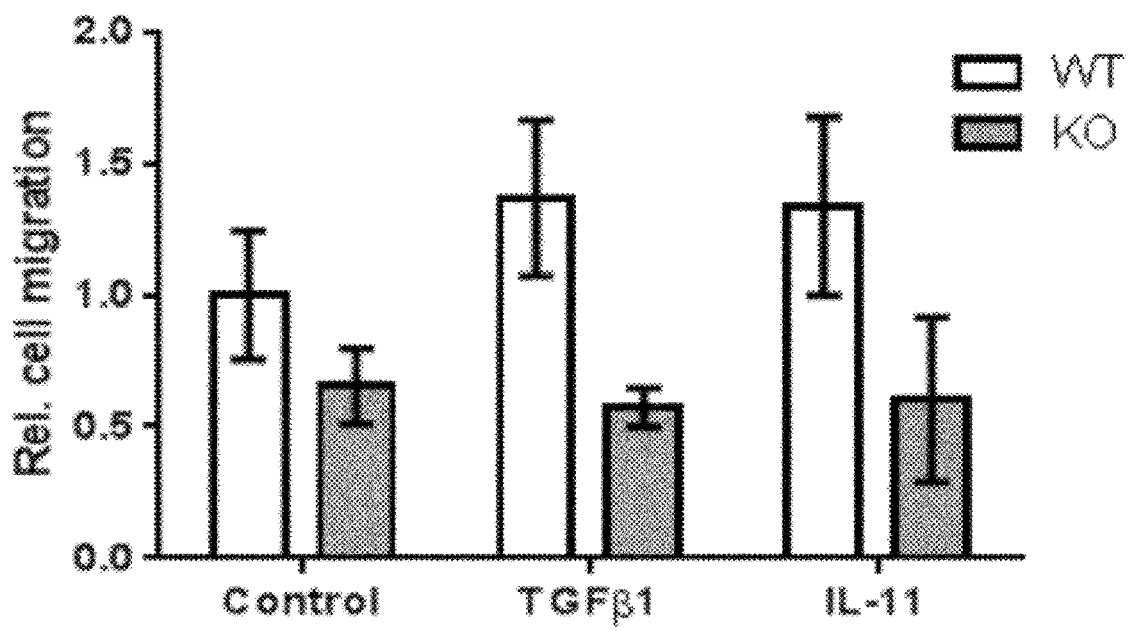
FIG. 24. Bar chart showing lung fibroblast cell migration with and without IL-11 signalling. Migration of lung fibroblasts from IL-11RA+/+(WT) and IL-11RA−/− (KO) animals was analysed in an in vitro scratch assay without stimulus, or in the presence of TGFβ1 or IL-11.

The results are shown in FIG. 24. Lung fibroblasts derived from WT mice were shown to migrate faster in the presence of TGFβ1 and IL-11, indicating a pro-fibrotic effect of both cytokines in lung fibroblasts. Cells lacking IL-11 signalling derived from KO mice migrated more slowly as compared to WT cells. They also did not migrate faster in the presence of TGFβ1. The scratch assay revealed that lung fibroblasts lacking IL-11 signalling have a decrease cell migration rate both in the presence of TGFβ1 or IL-11, and at baseline. Thus, inhibition of IL-11 signalling is anti-fibrotic in the lung.

3.2 Heart Fibrosis

The efficacy of IL-11 inhibition to treat fibrotic disorders was investigated in vivo. A mouse model for cardiac fibrosis, in which fibrosis is induced by treatment with AngII, was used to investigate whether IL-11RA −/− mice were protected from cardiac fibrosis.

Briefly, a pump was implanted, and wildtype (\NT) IL-11RA(+/+) and knockout (KO) IL-11RA(−/−) mice were treated with AngII (2 mg/kg/day) for 28 days. At the end of the experiment, collagen content was assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

The results are shown in FIGS. 12A to 12D. The IL-11RA−/− mice were found to be protected from the profibrotic effects of AngII.

3.3 Kidney Fibrosis

A mouse model for kidney fibrosis was established in wildtype (WT) IL-11RA(+/+) and knockout (KO) IL-11RA (−/−) mice by intraperitoneal injection of folic acid (180 mg/kg) in vehicle (0.3M NaHCO$_3$); control mice were administered vehicle alone.

Kidneys were removed 28 days post-injection, weighed and either fixed in 10% neutral-buffered formalin for Masson's trichrome and Sirius staining or snap-frozen for collagen assay, RNA, and protein studies.

Total RNA was extracted from the snap-frozen kidney using Trizol reagent (Invitrogen) and Qiagen TissueLyzer method followed by RNeasy column (Qiagen) purification. The cDNA was prepared using iScript™ cDNA synthesis kit, in which each reaction contained 1 μg of total RNA, as per the manufacturer's instructions. Quantitative RT-PCR gene expression analysis was performed on triplicate samples with either TaqMan (Applied Biosystems) or fast SYBR green (Qiagen) technology using StepOnePlus™ (Applied Biosystem) over 40 cycles. Expression data were normalized to GAPDH mRNA expression level and we used the 2-ΔΔCt method to calculate the fold-change. The snap-frozen kidneys were subjected to acid hydrolysis by heating in 6M HCl at a concentration of 50 mg/ml (95° C., 20 hours). The amount of total collagen in the hydrolysate was quantified based on the colorimetric detection of hydroxyproline using Quickzyme Total Collagen assay kit (Quickzyme Biosciences) as per the manufacturer's instructions.

Figure 15:
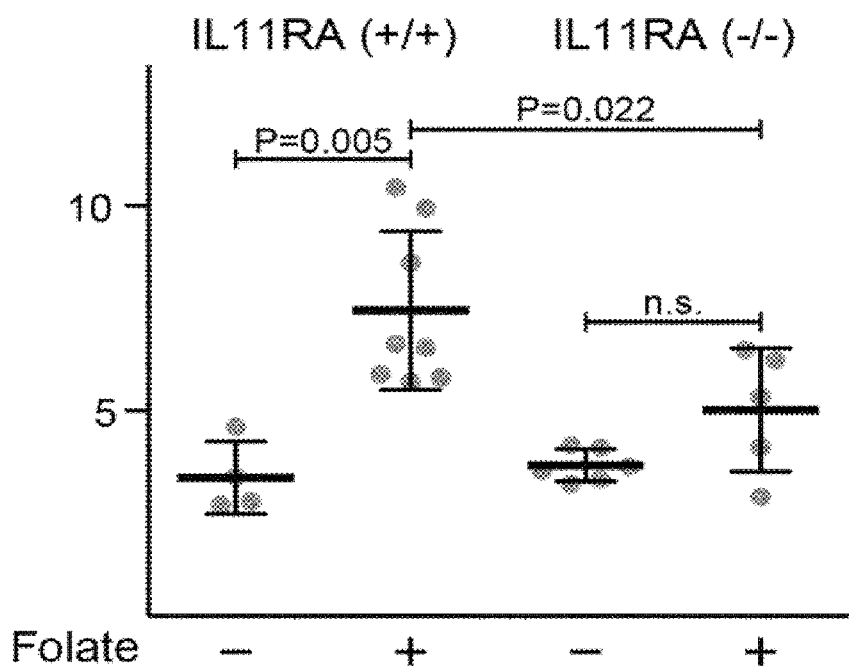
FIG. 15. Graphs showing the effect of IL-11RA knockout on folate-induced kidney fibrosis as measured by collagen content in kidney tissue.

The results of the analysis are shown in FIG. 15. Folate-induced kidney fibrosis is shown to be dependent on IL-11 mediated signalling. A significant increase in collagen content in kidney tissue was observed in IL-11RA+/+ mice, indicative of kidney fibrosis. No significant increase in collagen content was observed in IL-11RA −/− mice. Animals deficient for IL-11 signalling had significantly less collagen deposition in kidneys after toxic injury as compared to wild type animals.

3.4 Lung Fibrosis

Figure 13A:
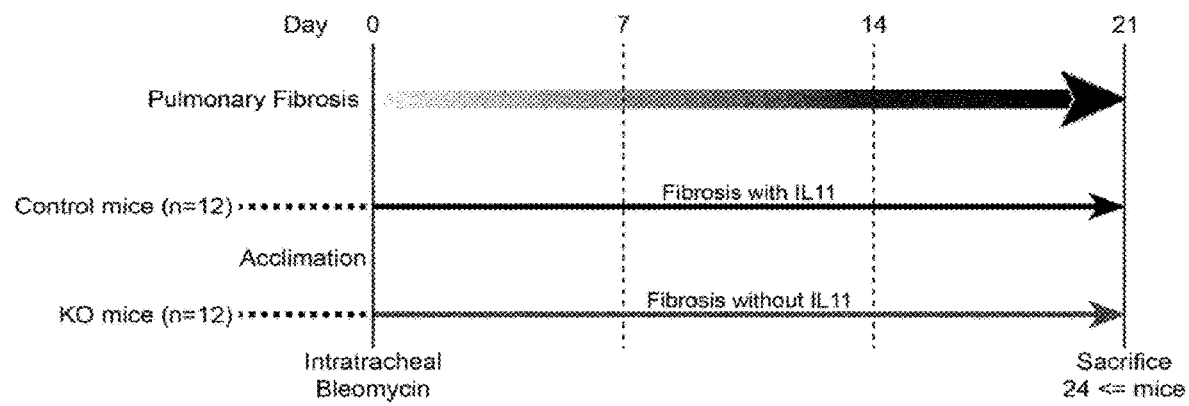
FIG. 13. Schematics of the experimental procedures for analysing fibrosis in (A) lung, (B) skin and (C) eye for IL-11RA −/− mice as compared to IL-11RA +/+ mice.
Figure 13B:
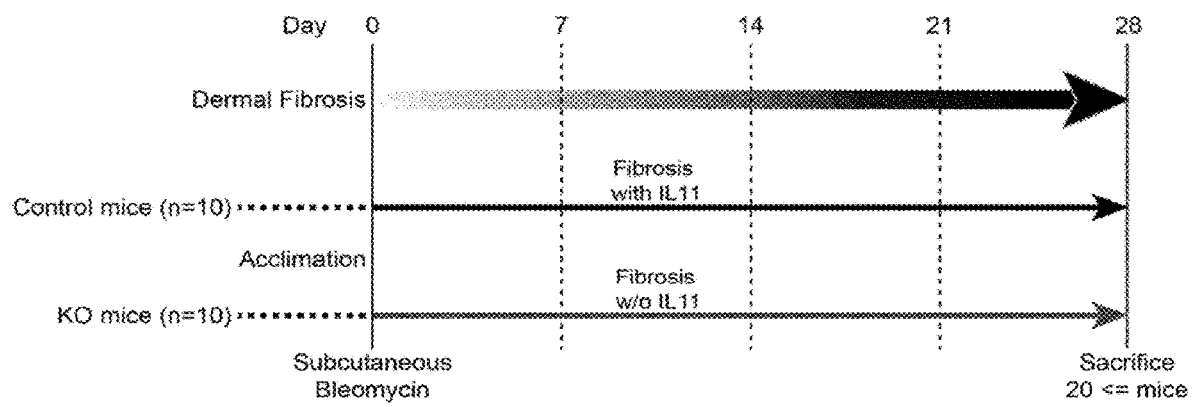
Figure 13C:
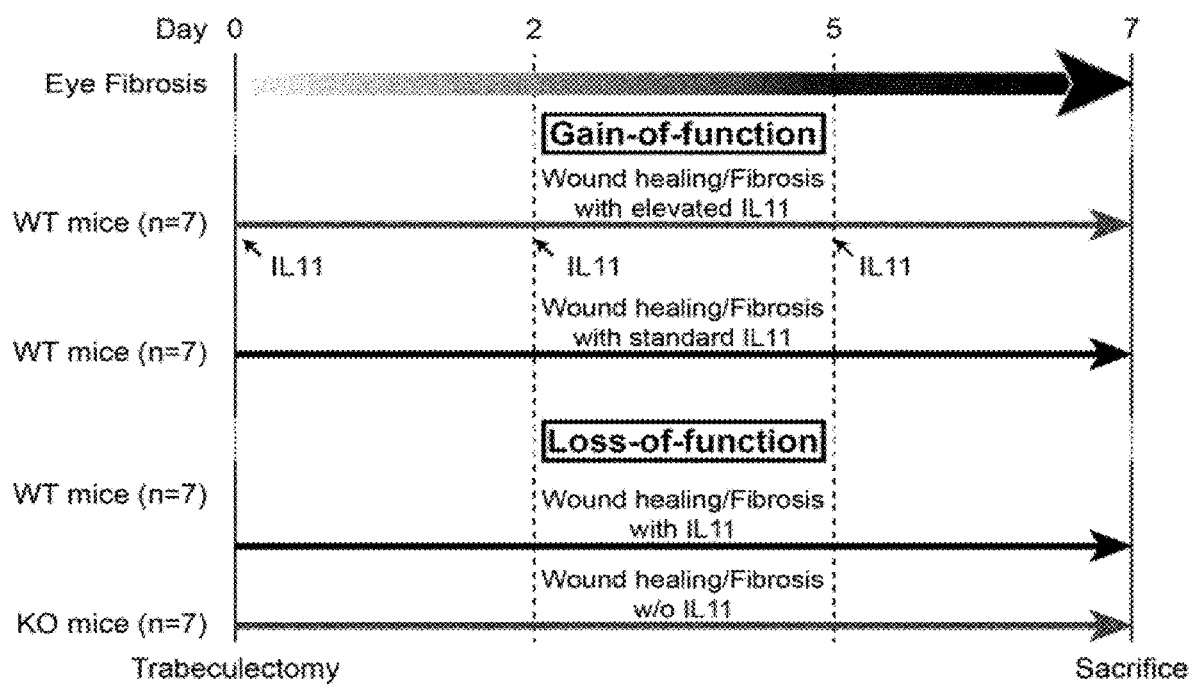

IL-11 is confirmed as a key mediator of fibrosis in the lung, skin and eye in further in vivo models using the IL-11RA −/− knockout mice. Schematics of the experiments are shown in FIGS. 13A to 13C.

To analyse pulmonary fibrosis, IL-11RA −/− mice and IL-11RA +/+ mice are treated by intratracheal administration of bleomycin on day 0 to establish a fibrotic response in the lung (pulmonary fibrosis). Fibrosis of the lung develops by 21 days, at which point animals are sacrificed and analysed for differences in fibrosis markers between animals with and without IL-11 signalling. IL-11RA −/− mice have a reduced fibrotic response in lung tissue as compared to IL-11RA +/+ mice, as evidenced by reduced expression of markers of fibrosis.

3.5 Skin Fibrosis

To analyse fibrosis of the skin, IL-11RA −/− mice and IL-11RA +/+ mice are treated by subcutaneous administration of bleomycin on day 0 to establish a fibrotic response in the skin. Fibrosis of the skin develops by 28 days, at which point animals are sacrificed and analysed for differences in fibrosis markers between animals with and without IL-11 signalling. IL-11RA −/− mice have a reduced fibrotic response in skin tissue as compared to IL-11RA +/+ mice, as evidenced by reduced expression of markers of fibrosis.

3.6 Eye Fibrosis

To analyse fibrosis in the eye, IL-11RA −/− mice and IL-11RA +/+ mice underwent trabeculectomy (filtration surgery) on day 0 to initiate a wound healing response in the eye. This mouse model of glaucoma filtration surgery has been shown to be an efficient model to evaluate the wound healing response in the eye (Khaw et al. 2001, Curr Opin Ophthalmol 12, 143-148; Seet et al. 2011, Mol. Med. 17, 557-567) and has successfully shown the beneficial effect of fibrotic modulators in vivo (Mead et al. 2003, Invest. Ophthalmol. Vis. Sci. 44, 3394-3401; Wong et al. 2003 Invest. Ophthalmol. Vis. Sci. 44, 1097-1103; Wong et al. 2005, Invest. Ophthalmol. Vis. Sci. 46, 2018-2022).

Briefly, the conjunctiva was dissected to expose the underlying sclera, after which an incision was made through the sclera into the anterior chamber of the eye using a 30-gauge needle. The created fistula allowed aqueous humor to exit into and underneath the conjunctiva. The dissected conjunctiva was then secured and closed at the limbus by a 10-0 (0.2 metric) Ethilon black monofilament nylon scleral suture. Fucithalmic ointment was instilled at the end of the procedure. The surgery was performed under anaesthesia by intraperitoneal injection of a 0.1 ml ketamine/xylazine mixture, as well as topical application of one drop per eye of 1% xylocaine. Fucithalmic ointment was instilled post-surgery to prevent infection. Surgery was performed with 70% propyl alcohol sterilized surgical scissors and forceps and sterile needles.

The accumulated fluid underneath the sutured conjunctiva was observed as a conjunctival bleb. Mice were euthanized on day 7 post-surgery for analyses. For qualitative immunehistological analyses, eyes from mice will be harvested by enucleation and then sectioned. Maturation of collagen fibres was evaluated with using the picro-sirius red/polarization light technique (Szendroi et al. 1984, Acta Morphol Hung 32, 47-55); orange-red indicated mature collagen, and yellow/green indicated newly formed immature collagen.

Figure 16A:
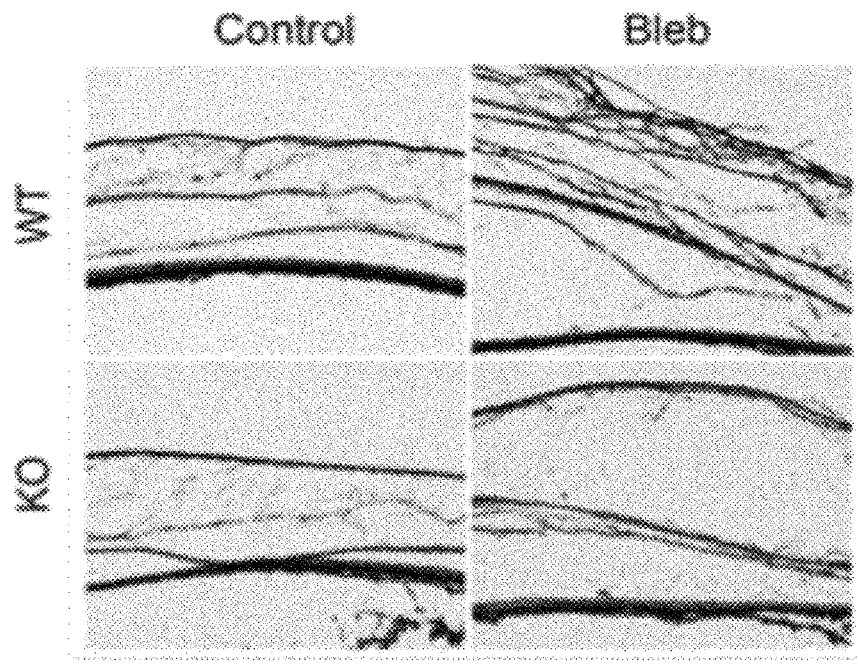
FIG. 16. Photographs showing the effect of IL-11RA knockout on wound healing and fibrosis in the eye following trabeculectomy (filtration surgery). (A) Eye sections of IL-11RA+/+(WT) and IL-11RA−/− (KO) animals 7 days after filtration surgery. (B) Maturation of collagen fibres as evaluated by picro-sirius red/polarization light technique (Szendroi et al. 1984, Acta Morphol Hung 32, 47-55); more fibrosis is observed in WT mice than KO mice.
Figure 16B:
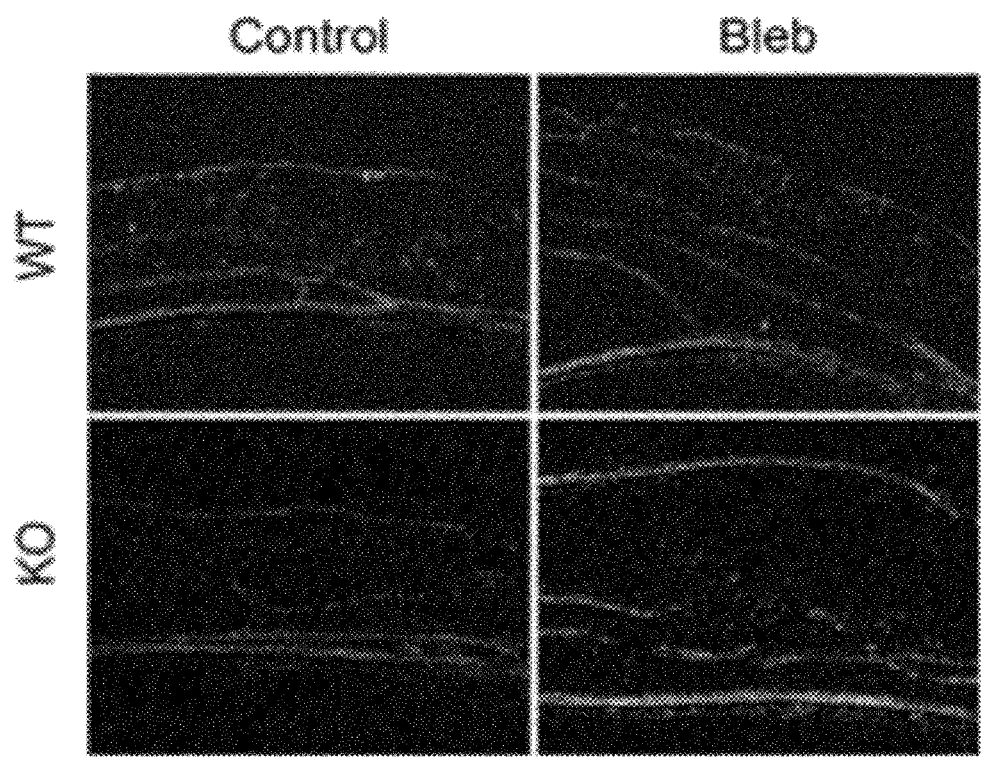

The results of the experiment are shown in FIGS. 16A and 16B. IL-11RA −/− mice were found to have a reduced fibrotic response in eye tissue as compared to IL-11RA +/+ mice.

3.7 Other Tissues

The effect of IL-11RA knockout on fibrosis is also analysed in mouse models of fibrosis for other tissues, such as the liver, bowel, and is also analysed in a model relevant to multiorgan (i.e. systemic) fibrosis. The fibrotic response is measured and compared between the IL-11RA −/− mice and IL-11RA +/+ mice. IL-11RA −/− mice have a reduced fibrotic response as compared to IL-11RA +/+ mice, as evidenced by reduced expression of markers of fibrosis.

Example 4: Analysis of the Molecular Mechanisms Underlying IL-11-Mediated Induction of Fibrosis The canonical mode of action of IL-11 is thought to be regulation of RNA expression via STAT3-mediated transcription (Zhu et al., 2015 PLoS ONE 10, e0126296), and also through activation of ERK.

STAT3 activation is observed following stimulation with IL-11. However, when fibroblasts are incubated with TGFβ1, only activation of the canonical SMAD pathway and ERK pathways is seen, and activation of STAT3 is not observed, even in spite of the fact that IL-11 is secreted in response to TGFβ1. Only ERK activation is common to both TGFβ1 and IL-11 signal transduction.

Cross-talk between TGFβ1 and IL-6 signalling has previously been described, wherein TGFβ1 blocks the activation of STAT3 by IL-6 (Walla et al., 2003 FASEB J. 17, 2130-2132). Given the close relationship between IL-6 and IL-11, similar cross-talk may be observed for IL-11 mediated signalling.

The inventors investigated by RNA-seq analysis whether regulation of RNA abundance was the underlying mechanism for the increased expression of fibrosis marker proteins in response to IL-11, which would suggest STAT3 as the underlying signalling pathway for IL-11 mediated profibrotic processes. Fibroblasts were incubated for 24 hours either without stimulus, or in the presence of TGFβ1, IL-11 or TGFβ1 and IL-11.

Figure 14A:
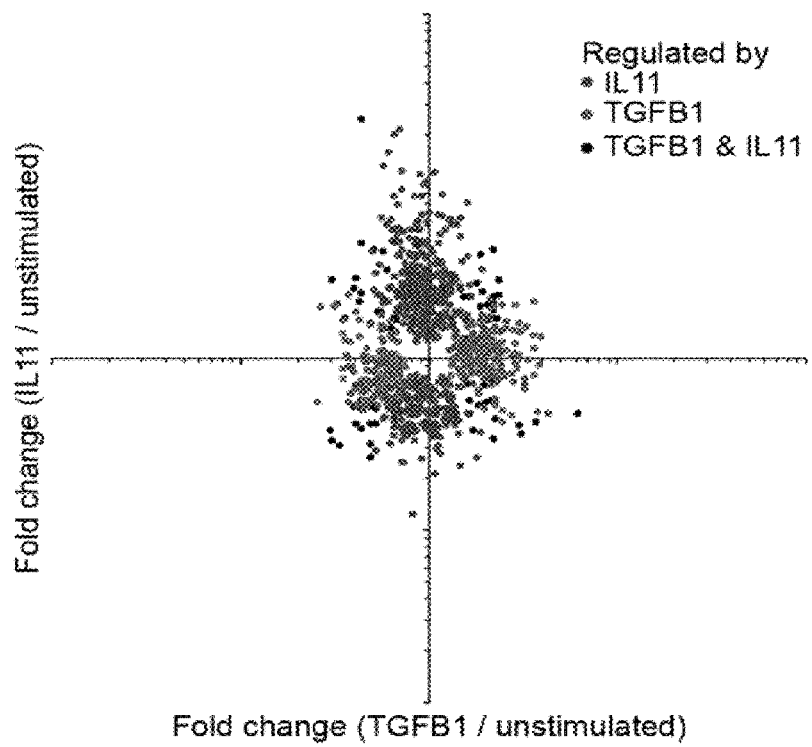
FIG. 14. Scatterplots showing fold change in gene expression. (A) Fold changes in gene expression in fibroblasts following stimulation with TGFβ1, IL-11 or TGFβ1 and IL-11. (B) Fold changes in gene expression in fibroblasts obtained from IL-11RA+/+ and IL-11RA−/− mice following stimulation with TGFβ1.
Figure 14B:
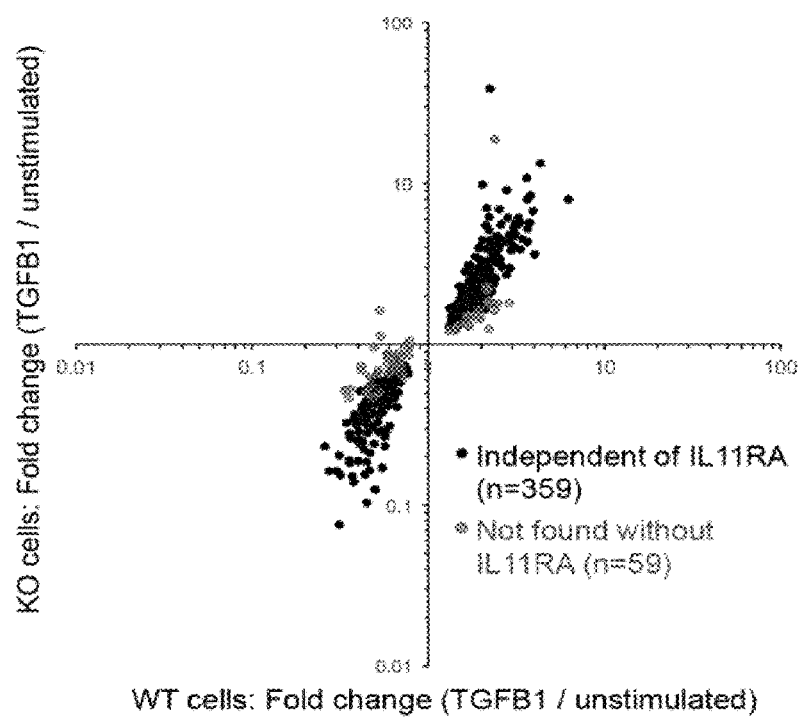

The results are shown in FIG. 14A. TGFβ1 induced the expression of collagen, ACTA2 (αSMA) and other fibrosis marker at the RNA level. However, IL-11 did not regulate the expression of these genes, but a different set of genes.

Gene ontology analysis suggests that a pro-fibrotic effect in fibroblasts is driven by IL-11-regulated RNA expression. Both TGFβ1 and IL-11 regulate an almost completely different set of genes on the RNA level.

Whilst TGFβ1 increases IL-11 secretion, the target genes of IL-11 are not regulated when both TGFβ1 and IL-11 are present. This suggests that TGFβ1 upregulates IL-11 and simultaneously blocks the canonical IL-11-driven regulation of RNA expression via STAT3, similar to what is known about the interaction of TGFβ1 and IL-6 pathways (Walia et al., 2003 FASEB J. 17, 2130-2132).

We also analysed whether RNA expression differences induced by TGFβ1 are dependent on IL-11 signalling, by analysing changes in RNA expression in fibroblasts obtained from IL-11RA −/− mice as compared to IL-11RA +/+ mice. RNA expression regulated by TGFβ1 is still observed when IL-11RA knockout cells were stimulated with TGFβ1, and RNA levels of αSMA, collagen etc. were still upregulated in the absence of IL-11 signalling (in IL-11RA −/− fibroblasts). When the pro-fibrotic effect of IL-11 and the anti-fibrotic effect of IL-11 inhibition was investigated in vitro, reduced expression of markers of fibrosis was only observed at the protein level, not at the transcriptional level as determined by qPCR.

The activation of non-canonical pathways (e.g. ERK signal transduction) is known to be crucial for the pro-fibrotic action of TGFβ1 (Guo and Wang, 2008 Cell Res 19, 71-88). It is likely that non-canonical pathways are likely to be important for signalling for all known pro-fibrotic cytokines, and that IL-11 is a post-transcriptional regulator which is essential for fibrosis.

Example 5: Decoy IL-11 Receptors 5.1 Decoy IL-11 Receptor Constructs

Decoy IL-11 Receptor molecules were designed and clones into the pTT5 vector for recombinant expression in 293-6E cells.

Briefly, an insert for the plasmid comprising cDNA encoding the ligand binding domains D1, D2 and D3 of gp130 in-frame with cDNA encoding either a 50 amino acid or 33 amino acid linker region, followed by cDNA encoding the ligand binding domains D2 and D3 of human IL-11Rα, followed by cDNA encoding the FLAG tag. The cDNA insert incorporated a leader sequence Kozak sequences at the 5' end, and included a 5' EcoRI restriction site and a 3' Hind III restriction site (downstream of a stop codon) for insertion into the pTT5 vector.

The two constructs encoding a decoy IL-11 receptor molecule having either a 50 amino acid or 33 amino acid sequence are respectively designated Decoy IL-11 Receptor 1 (D11R1) and Decoy IL-11 Receptor 2 (D11R2). The nucleotide sequences for the constructs (and the component sequences thereof) are shown in FIGS. 18A and 18B. The amino acid sequences for D11R1 and D11R2 (and the component sequences thereof) are shown in FIGS. 17A and 17B.

5.2 Decoy IL-11 Receptor Expression and Purification

The constructs were transfected into 293-6E cells for recombinant expression and purification. 293-6E cells were grown in serum-free FreeStyle™ 293 Expression Medium (Life Technologies, Carlsbad, Calif., USA). Cells were maintained in Erlenmeyer Flasks (Corning Inc., Acton, Mass.) at 37° C. with 5% $CO_2$ on an orbital shaker (VWR Scientific, Chester, Pa.).

One day before transfection, the cells were seeded at an appropriate density in Corning Erlenmeyer Flasks. On the day of transfection, DNA and transfection reagent were mixed at an optimal ratio and then added into the flask with cells ready for transfection. The recombinant plasmids encoding D11R1 and D11R2 were transiently transfected into suspension 293-6E cell cultures on two separate days.

Cell culture supernatants were collected on day 6 and used for purification. Briefly, cell culture broths were centrifuged and filtrated. 0.5 ml of resin was added to cell culture supernatants and incubated for 3~4 hours to capture the target protein.

After washing and elution with appropriate buffers, eluted fractions were analysed by SDS-PAGE and Western blot using Rabbit anti-FLAG polyclonal Ab (GenScript, Cat.No.A00170) to confirm expression of the FLAG-tagged decoy IL-11 receptor molecules.

The purified species were quantified and stored at −80° C.

Example 6: Functional Characterisation of Decoy IL-11 Receptors 6.1 Ability to Inhibit Human IL-11 Mediated Signalling To investigate ability to neutralise human IL-11-mediated signalling, cardiac atrial human fibroblasts were cultured in wells of 96-well plates in the presence of TGFβ1 (5 ng/ml) for 24 hours, in the presence or absence of various concentrations of D11R1 or D11R2.

TGFβ1 promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Expression of αSMA was analysed with the Operetta High-Content Imaging System in an automated high-throughput fashion.

D11R1 or D11R2 were added to fibroblast cultures that were stimulated with TGFβ1 at final concentrations of 5 ng/ml, 50 ng/ml and 500 ng/ml, and at the end of the 24 hour culture period, the percentage of αSMA-positive fibroblasts in the culture was determined.

Figure 19A:
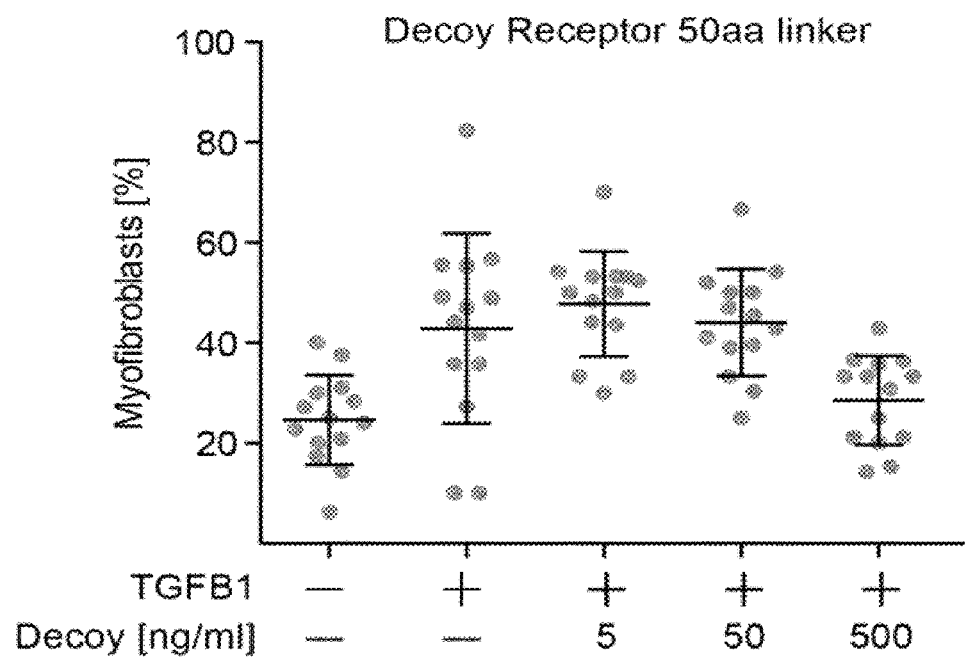
FIG. 19. Graphs showing the effect of decoy IL-11 receptors on fibrosis in response to stimulation with TGFβ1. Fibroblasts were cultured in vitro in the presence/absence of TGFβ1 (5 ng/ml), in the presence or absence of (A) D11R1 (Decoy Receptor 50aa Linker) or (B) D11R2 (Decoy Receptor 33aa Linker), at various different concentrations. Myofibroblast generation after 24 hours (i.e. the percentage of activated fibroblasts) was determined by analysis of αSMA expression.
Figure 19B:
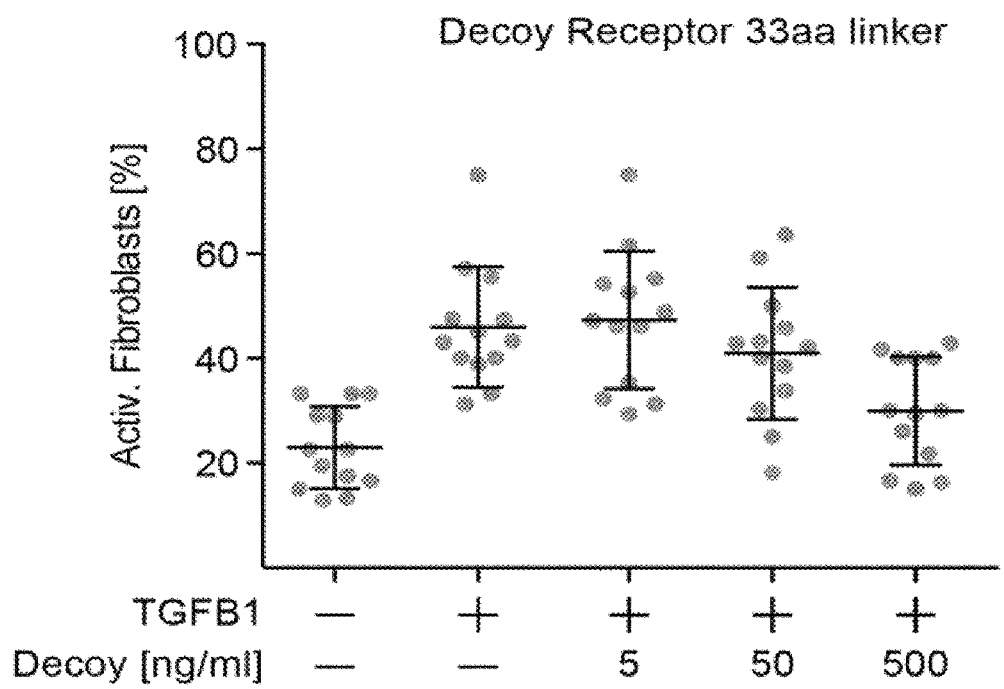
Figure 22A:
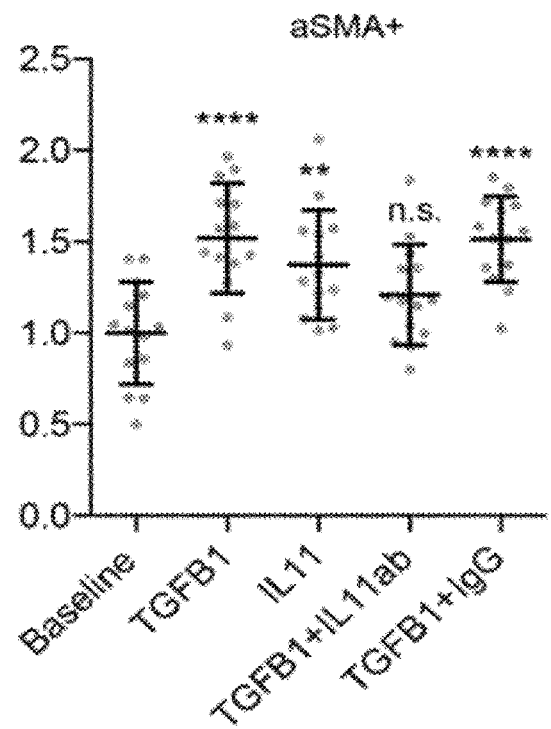
FIG. 22. Graphs showing that IL-11 is required for the pro-fibrotic effects of TGFβ1 in liver fibroblasts. Activation and proliferation of primary human liver fibroblasts, with or without stimulation with TGFβ1, and in the presence/absence of neutralising anti-IL-11 antibody or isotype control IgG, as measured by analysis of the proportion of (A) α-SMA positive cells, (B) EdU positive cells, (C) Collagen positive cells and (D) Periostin positive cells as compared to the unstimulated cells (Baseline). [Mean±SD, Dunnett] *P<0.05, P<0.01, *P<0.001 or ****P<0.0001.
Figure 22B:
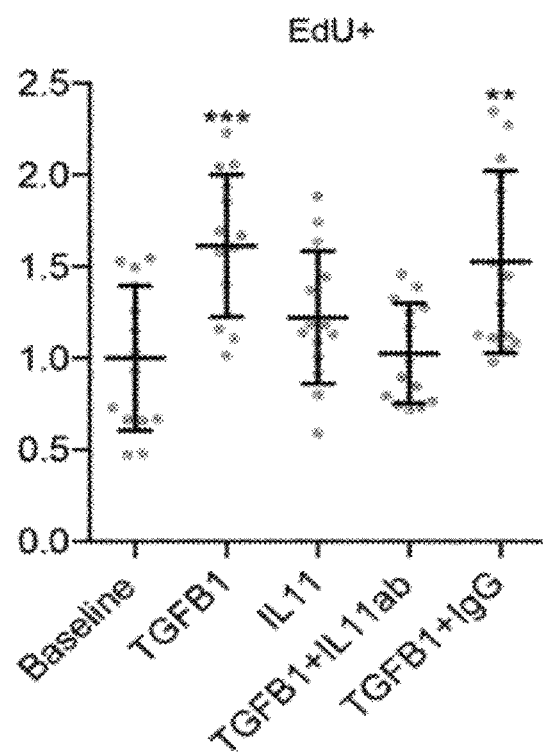
Figure 22C:
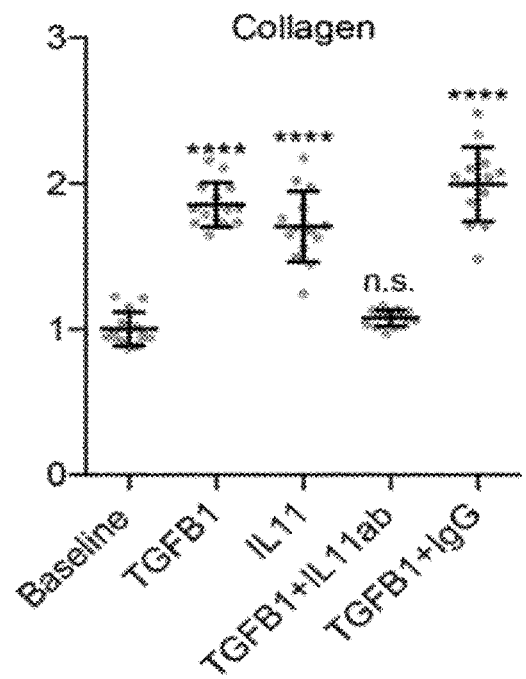
Figure 22D:
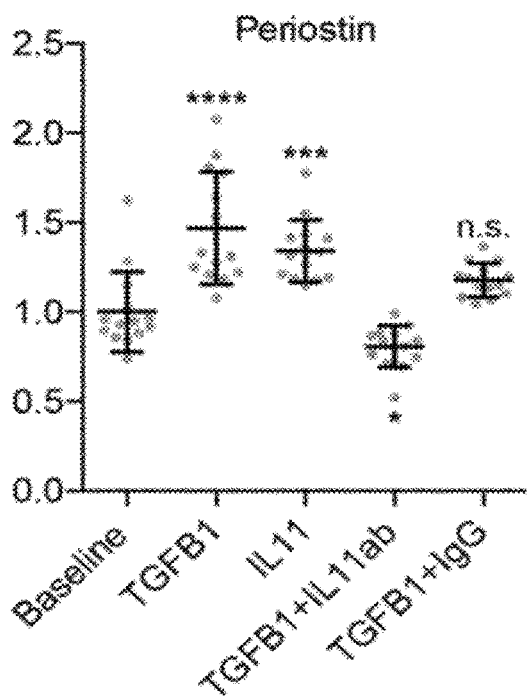

The results of the experiments are shown in FIGS. 19A and 19B. Both D11R1 and D11R2 were demonstrated to be capable of neutralising signalling mediated by human IL-11 in a dose-dependent manner.

The $IC_{50}$ for the D11R1 and D11R2 molecules was determined to be ~1 nM.

6.2 Ability to Inhibit Mouse IL-11 Mediated Signalling

The ability of D11R1 and D11R2 to inhibit mouse IL-11-mediated signalling is investigated, following the same procedure as described in section 6.1 above, but using mouse dermal fibroblasts instead of human atrial fibroblasts.

D11R1 and D11R2 are demonstrated to be capable of neutralising IL-11/IL-11R signalling in mouse dermal fibroblasts, as determined by observation of a relative decrease in the proportion of αSMA-positive fibroblasts at the end of the 24 h culture period in the presence of D11R1 or D11R2 as compared to culture in the absence of the decoy IL-11 receptors.

6.3 Ability to Inhibit IL-11 Trans Signalling, by IL-11 in Complex with IL-11RA

Trans signalling is recognised as a major aspect of IL-6 signalling, where a complex of IL-6 and soluble IL-6Ra can activate cells that express gp130, but lack the IL-6 receptor (Hunter and Jones, 2015 Nature Immunology 16, 448-457).

It has recently been suggested that trans signalling by a complex of IL-11 and soluble IL-11RA is also important for IL-11 biology (Lokau et al., Cell Reports (2016) 14, 1761-1773). Using a recombinant fusion protein of IL-11 and IL-11Rα (as described in Pflanz et al., Febs Lett (1999) 450: 117-122), D11R1 and D11R2 are screened for the ability to inhibit trans signalling mediated by IL-11:IL-11Rα complex.

Importantly, decoy IL-11 receptors which are capable of inhibiting both classical IL-11 mediated signalling and IL-11 trans signalling by IL-11:IL-11Rα complex are able to inhibit all known modes of IL-11/1-11R signalling.

The IL-11:IL-11Rα fusion protein (hereafter referred to as hyper IL-11) consists of the extracellular domain of the IL-11 receptor alpha (IL-11Rα) linked to IL-11.

Figure 25A:
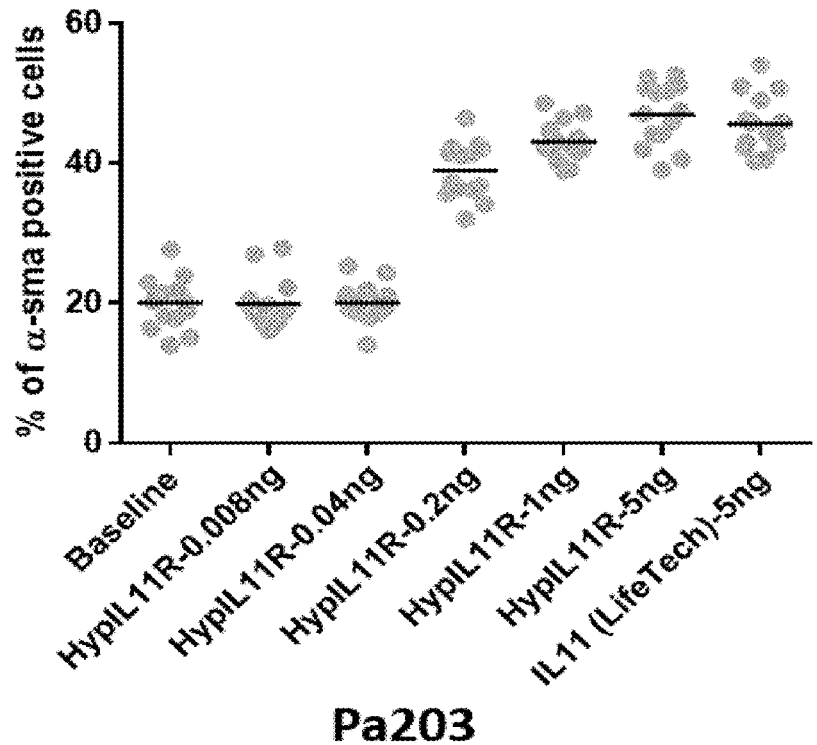
FIG. 25. Graphs showing fibroblast activation in response to hyper IL-11. Cells were stimulated with the indicated amount (in ng/ml) of hyper IL-11 or recombinant IL-11, and fibroblast activation was measured by analysis of the percentage of α-SMA positive cells. (A) and (B) present the results of two different experiments.
Figure 25B:
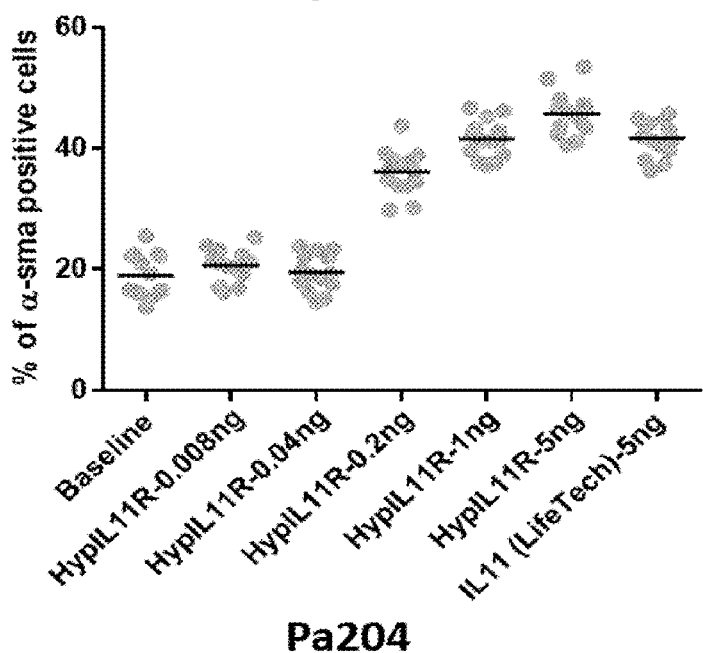

Hyper IL-11 was found to be a more potent activator of human fibroblasts than recombinant IL-11 protein. Briefly, in two separate experiments human fibroblasts were cultured without stimulation (Baseline), in the presence of different amounts of hyper IL-11 (0.008 ng/ml, 0.04 ng/ml, 0.2 ng/ml, 1 ng/ml and 5 ng/ml), or 5 ng/ml recombinant human IL-11 obtained from a commercial source, and fibroblast activation was analysed by determining the percentage of αSMA-positive cells as described herein. The results are shown in (FIGS. 25A and 25B). Hyper-IL-11 activated fibroblasts in a dose-dependent fashion, and was a more potent activator than IL-11.

The IL-11:IL-11Rα fusion protein was prepared as follows:

DNA encoding IL-11:IL-11Rα fusion protein (i.e. SEQ ID NO:21) was cloned into pTT5 vector, and transfected into 293-6E cells in culture in serum-free FreeStyle™ 293 Expression Medium (Thermo Fisher Scientific).

Cells were maintained in Erlenmeyer Flasks (Corning Inc.) at 37° C. with 5% $CO_2$ on an orbital shaker (VWR Scientific).

Cell culture supernatants were collected on day 6 were used for purification.

Cell culture supernatant was loaded onto an affinity purification column.

After washing and elution with appropriate buffer, the eluted fractions were pooled and buffer exchanged to final formulation buffer.

The purified IL-11:IL-11Rα fusion protein was analyzed by SDS-PAGE, Western blot to confirm molecular weight and purity.

Figure 26:
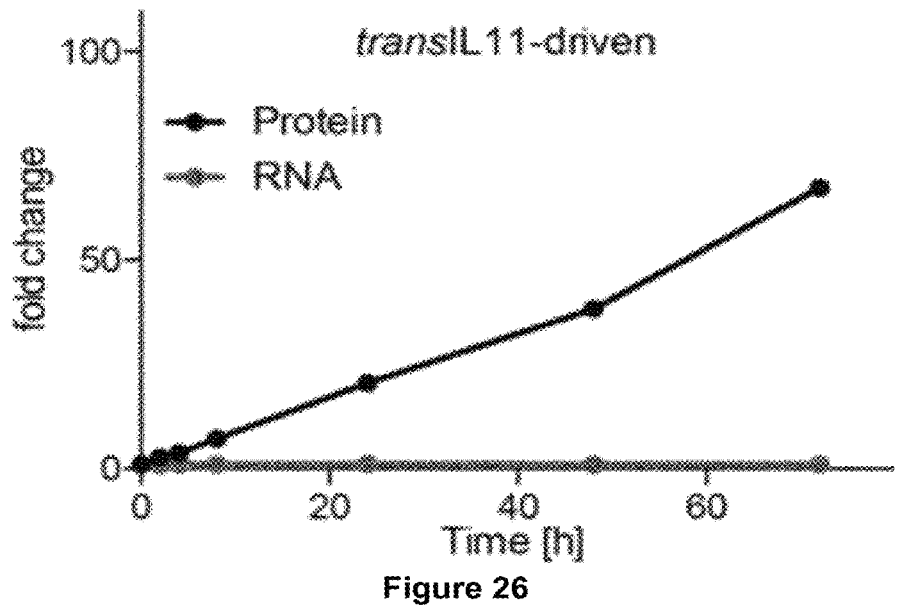
FIG. 26. Graph showing induction of IL-11 secretion in primary fibroblasts by hyper IL-11. Cells were stimulated with hyper IL-11, and IL-11 RNA and native IL-11 protein levels were measured in the cell culture supernatant by ELISA at the indicated time points.

DNA encoding IL-11:IL-11Rα fusion protein (SEQ ID NO: 21):
GAATTCCCGCCGCCACCATGGGCTGGTCCTGCATCATCCTGTTTCTGGTGG
CCACAGCCACCGGCGTGCACTCTCCACAGGCTTGGGGACCTCCAGGCGTGC
AGTATGGCCAGCCTGGCAGATCCGTGAAGCTGTGCTGTCCTGGCGTGACAG
CTGGCGACCCTGTGTCCTGGTTCAGAGATGGCGAGCCCAAGCTGCTGCAGG
GCCCAGATTCTGGACTGGGCCACGAACTGGTGCTGGCCCAGGCCGATTCTA
CCGACGAGGGCACCTACATCTGCCAGACCCTGGATGGCGCCCTGGGCGGAA
CAGTGACACTGCAGCTGGGCTACCCTCCCGCCAGACCTGTGGTGTCTTGTC
AGGCCGCCGACTACGAGAACTTCAGCTGCACATGGTCCCCCAGCCAGATCA
GCGGCCTGCCCACCAGATACCTGACCAGCTACCGGAAGAAAACCGTGCTGG
GCGCCGACAGCCAGAGAAGAAGCCCTTCTACAGGCCCTGGCCCTGCCCTC
AGGATCCTCTGGGAGCTGCCAGATGTGTGGTGCACGGCGCCGAGTTCTGGT
CCCAGTACCGGATCAACGTGACCGAAGTGAACCCCCTGGGCGCCTCCACAA
GACTGCTGGATGTGTCCCTGCAGAGCATCCTGCGGCCCGATCCTCCACAGG
GCCTGAGAGTGGAAAGCGTGCCCGGCTACCCCAGAAGGCTGAGAGCCAGCT
GGACATACCCCGCCTCTTGGCCTTGCCAGCCCCACTTCCTGCTGAAGTTTC
GGCTGCAGTACCGGCCAGCCCAGCACCCTGCTTGGAGCACAGTGGAACCTG
CCGGCCTGGAAGAAGTGATCACAGACGCCGTGGCCGGACTGCCTCATGCTG
TGCGGGTGTCCGCCAGAGACTTTCTGGATGCCGGCACCTGGTCTACCTGGT
CCCCAGAAGCCTGGGGCACACCTTCTACTGGCGGACCTGCTGGACAGTCTG
GCGGAGGCGGAGGAAGTGGCGGAGGATCAGGGGGAGGATCTGTGCCTGGAC
CTCCTCCAGGACCCCCTAGAGTGTCCCCAGATCCTAGGGCCGAGCTGGACT
CTACCGTGCTGCTGACCAGATCCCTGCTGGCCGACACAAGGCAGCTGGCTG
CCCAGCTGAGAGACAAGTTCCCCGCCGACGGCGACCACAACCTGGATAGCC
TGCCTACCCTGGCCATGTCTGCTGGCGCACTGGGGGCTCTGCAGCTGCCTG
GGGTGCTGACTAGACTGAGAGCCGACCTGCTGAGCTACCTGCGGCATGTGC
AGTGGCTGAGAAGGGCTGGCGGCAGCAGCCTGAAAACCCTGGAACCTGAGC
TGGGCACACTGCAGGCCAGACTGGACAGACTGCTGCGCAGACTGCAGCTGC
TGATGAGCAGACTGGCTCTGCCCCAGCCTCCTCCTGACCCTCCTGCTCCTC
CACTGGCTCCTCCAAGCTCTGCTTGGGGCGGAATTAGAGCCGCCCACGCCA
TTCTGGGAGGCCTGCACCTGACACTGGATTGGGCAGTGCGGGCCTGCTGC
TGCTGAAAACCAGACTGCACCACCACCATCACCACTGATAAGCTT Amino acid sequence of IL-11:IL-11Rα fusion protein (SEQ ID NO: 22):
MGWSCIILFLVATATGVHSPQAWGPPGVQYGQPGRSVKLCCPGVTAGDPVS
WFRDGEPKLLQGPDSGLGHELVLAQADSTDEGTYICQTLDGALGGTVTLQL
GYPPARPVVSCQAADYENFSCTWSPSQISGLPTRYLTSYRKKTVLGADSQR
RSPSTGPWPCPQDPLGAARCVVHGAEFWSQYRINVTEVNPLGASTRLLDVS
LQSILRPDPPQGLRVESVPGYPRRLRASWTYPASWPCQPHFLLKFRLQYRP
AQHPAWSTVEPAGLEEVITDAVAGLPHAVRVSARDFLDAGTWSTWSPEAWG
TPSTGGPAGQSGGGGSGGGSGGGSVPGPPGPPRVSPDPRAELDSTVLLT
RSLLADTRQLAAQLRDKFPADGDHNLDSLPTLAMSAGALGALQLPGVLTRL
RADLLSYLRHVQWLRRAGGSSLKTLEPELGTLQARLDRLLRRLQLLMSRLA
LPQPPPDPPAPPLAPPSSAWGGIRAAHAILGGLHLTLDWAVRGLLLLKTRL
HHHHHH Fibroblasts cultured in vitro and stimulated with hyper IL-11 were shown to upregulate IL-11 protein expression, as determined by ELISA (FIG. 26). Interestingly, an increase in IL-11 RNA level was not detected in response to stimulation with hyper IL-11. Unlike TGFB1, which increases IL-11 expression at both the RNA and the protein level, hyper IL-11 seems to upregulate IL-11 expression only post-transcriptionally, at the protein level.

The ability of the D11R1 and D11R2 decoy IL-11 receptors to inhibit signalling mediated by hyper IL-11 is investigated.

Human atrial fibroblasts are incubated for 24 h in the presence of hyper IL-11 (0.2 ng/ml), and in the presence of D11R1 or D11R2. Following incubation, cells are stained for αSMA to determine the fraction of myofibroblasts. Stimulation with hyper IL-11 causes a ~2-fold increase in the percentage of activated fibroblasts as compared to non-stimulated cultures.

D11R1 and D11R2 are demonstrated to be capable of inhibiting IL-11 trans signalling, as determined by observation of a relative decrease in the proportion of αSMA-positive fibroblasts at the end of the 24 h culture period in the presence of D11R1 or D11R2 as compared to culture in the absence of the decoy IL-11 receptors.

6.4 Analysis of Decoy IL-11 Receptor Affinity for IL-11

D11R1 and D11R2 are analysed for their affinity of binding to human IL-11 by ELISA assay.

Recombinant human IL-11 was obtained from Genscript and Horseradish peroxidase (HRP)-conjugated anti-FLAG antibody is obtained. Corning 96-well ELISA plates were obtained from Sigma. Pierce 3,3',5,5'-tetramethylbenzidine (TMB) ELISA substrate kit was obtained from Life Technologies (0.4 g/mL TMB solution, 0.02% hydrogen peroxide in citric acid buffer). Bovine serum albumin and sulphuric acid was obtained from Sigma. Wash buffer comprised 0.05% Tween-20 in phosphate buffered saline (PBS-T). Tecan Infinite 200 PRO NanoQuant is used to measure absorbance.

An indirect ELISA is performed to assess the binding affinity of D11R1 and D11R2 at 50% of effective concentration ($EC_{50}$) as previously described (Unverdorben et al., (2016) MAbs 8, 120-128.). ELISA plates are coated with 1 μg/mL of recombinant human IL-11 overnight at 4° C. and remaining binding sites were blocked with 2% BSA in PBS. D11R1 and D11R1 are diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-decoy IL-11 receptor binding is performed with HRP-conjugated anti-FLAG antibody. Following 2 hours of incubation with the detection antibody, 100 μl of TMB substrate is added for 15 mins and chromogenic reaction stopped with 100 μl of 2 M $H_2SO_4$. Absorbance reading is measured at 450 nm with reference wavelength correction at 570 nm. Data are fitted with GraphPad Prism software with log transformation of decoy IL-11 receptor concentrations followed by non-linear regression analysis with the asymmetrical (five-parameter) logistic dose-response curve to determine EC50 values.

The same materials and procedures as described above were performed to determine the affinity of binding to recombinant murine IL-11 obtained from Genscript.

6.5 Ability to Inhibit Human IL-11 Mediated Signalling in a Variety of Tissues

Ability of the decoy IL-11 receptors D11R1 and D11R2 to neutralise IL-11-mediated signalling and trans signalling in fibroblasts obtained from a variety of different tissues is investigated, essentially as described in sections 6.1 and 6.3 except that instead of cardiac atrial human fibroblasts, human fibroblasts derived from liver, lung, kidney, eye, skin, pancreas, spleen, bowel, brain, and bone marrow are used for the experiments.

D11R1 and D11R2 are demonstrated to be capable of neutralising signalling in fibroblasts derived from the various different tissues, as determined by observation of a relative decrease in the proportion of αSMA-positive fibroblasts at the end of the 24 h culture period in the presence of the decoy IL-11 receptors as compared to culture in the absence of the decoy IL-11 receptors.

6.6 Comparison of Ability of Decoy IL-11 Receptors to Inhibit IL-11 Mediated Signaling as Compared to a Commerically Available Anti-IL-11 Antibody The ability of D11R1 and D11R2 to inhibit IL-11 mediated signalling was compared to inhibition by the commercially available mouse monoclonal anti-IL-11 antibody clone #22626 (Catalog No. MAB218; R&D Systems, MN, USA).

Briefly, human atrial fibroblasts were cultured in the absence of stimulation or with 5 ng/ml TGFβ1 for 24 hours, in the presence or absence of the commercial anti-IL-11 antibody, D11R1 (FP50), D11R2 (FP33) or in the presence of a multi-tag fusion protein control. Fibroblast activation was analysed by determining the percentage of αSMA positive cells.

Figure 27A:
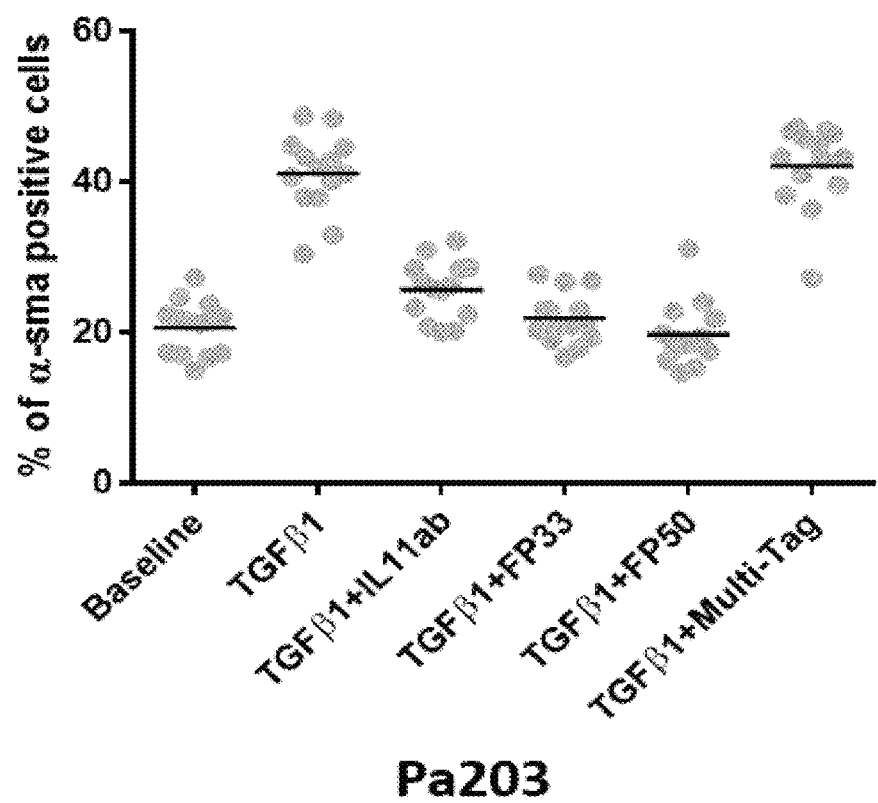
FIG. 27. Graphs showing relative inhibition of IL-11 mediated signalling by decoy IL-11 receptors as compared to anti-IL-11 antibody. Activation of human atrial fibroblasts, with or without stimulation with TGFβ1, and in the presence of anti-IL-11 antibody, D11 R1 (FP50), D11 R2 (FP33), or a multi-tag fusion protein control. Fibroblast activation was analysed by determining the percentage of αSMA positive cells. (A) and (B) present the results of two different experiments.
Figure 27B:
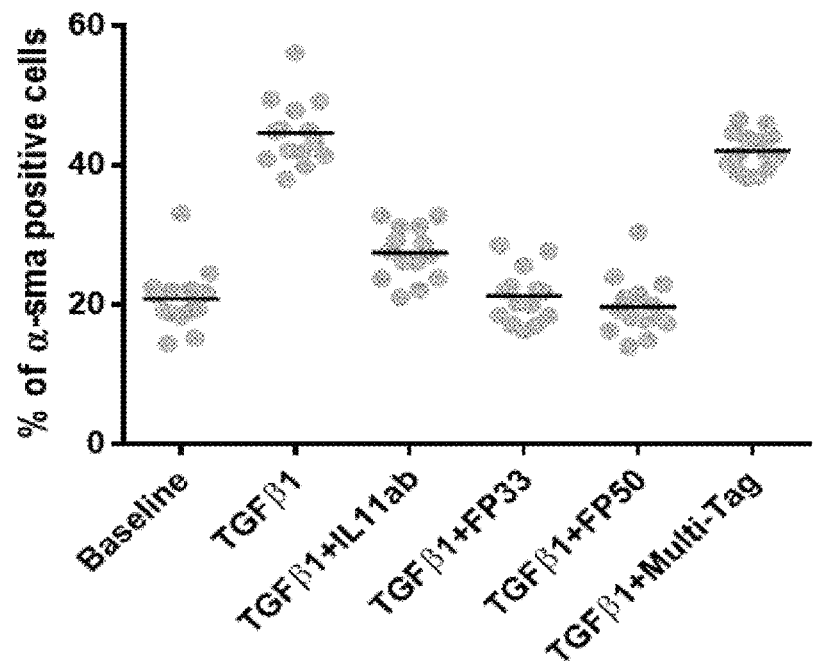

The results of two different experiments are shown in FIGS. 27A and 27B. Both D11R1 and D11R2 were found to be able to inhibit IL-11 mediated signalling to a greater extent than the commercial anti-IL-11 antibody, and to completely abrogate fibroblast activation in response to stimulation with TGFβ1.

In a further experiment it was investigated as to whether 500 ng/ml of Decoy receptor would be sufficient to inhibit IL-11 signalling. Briefly, human atrial fibroblasts were cultured in the absence of stimulation or with 5 ng/ml TGFβ1 for 24 hours, in the presence or absence of 2 μg/ml of the commercial anti-IL-11 antibody, 500 ng/ml of D11R1 (FP50), or 500 ng/ml of D11R2 (FP33). Fibroblast activation was analysed by determining the percentage of αSMA positive cells.

Figure 28:
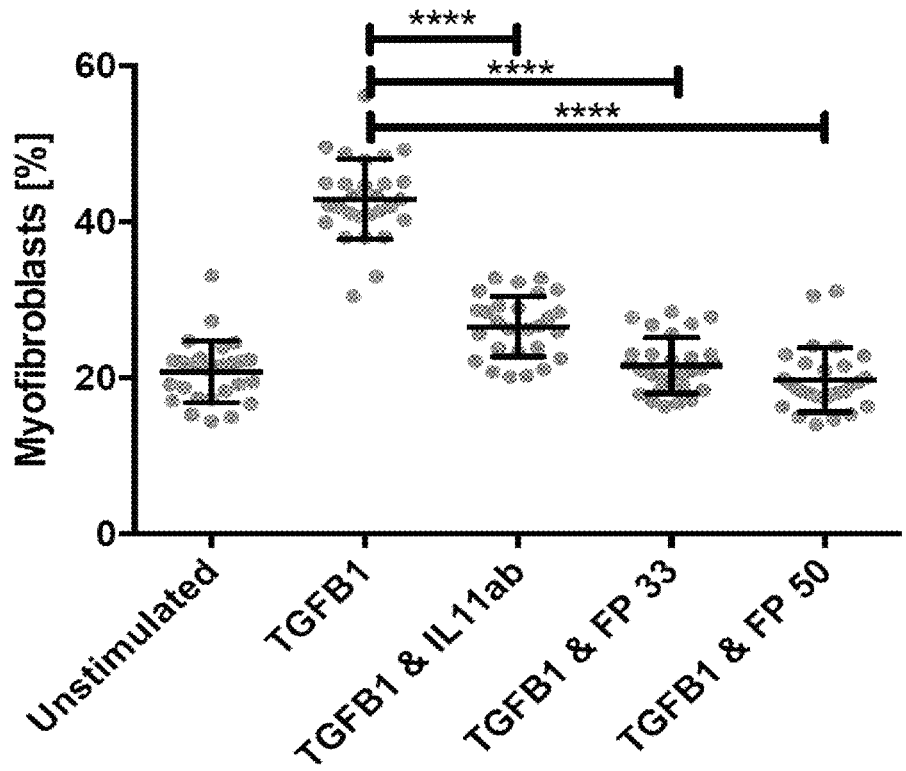
FIG. 28. Graphs showing relative inhibition of IL-11 mediated signalling by decoy IL-11 receptors as compared to anti-IL-11 antibody. Activation of human atrial fibroblasts, with or without stimulation with TGFβ1, and in the presence of 2 μg/ml anti-IL-11 antibody, 500 ng/ml D11 R1 (FP50) or 500 ng/ml D11 R2 (FP33). Fibroblast activation was analysed by determining the percentage of αSMA positive cells. [Mean±SD, Dunnett]****P<0.0001.

The results are shown in FIG. 28. Both D11R1 and D11R2 were found to completely abrogate fibroblast activation in response to stimulation with TGFβ1 even at a concentration as low as 500 ng/ml, and both decoy receptors were found to be more effective at inhibiting fibroblast activation than the commercial anti-IL-11 antibody, even when the antibody was used at four times the concentration of the decoy receptors.

Example 7: Further Biochemical Analysis of the Decoy IL-11 Receptors

D11R1 and D11R2 described above are subjected to further biochemical analysis.

The decoy IL-11 receptors are analysed by BIAcore, Biolayer interferometry (BLI) and MicroScale Thermophoresis (MST) analysis to determine the affinity of binding to human IL-11 and mouse IL-11.

BIAcore determination of affinity by surface plasmon resonance (SPR) analysis is performed as described in Rich et al., Anal Biochem. 2008 Feb. 1; 373(1):112-20.

Biolayer interferometry analysis of affinity is performed as described in Concepcion et al., Comb Chem High Throughput Screen. 2009 September; 12(8):791-800.

MicroScale Thermophoresis analysis of affinity is performed as described in Jerabek-Willemsen et al., Assay Drug Dev Technol. 2011 August; 9(4): 342-353.

Aggregation of the decoy IL-11 receptors is analysed by size exclusion chromatography (SEC), as described in Iacob et al., J Pharm Sci. 2013 December; 102(12): 4315-4329.

Hydophobicity of the decoy IL-11 receptors is analysed by Hydrophobic interaction chromatography (HIC) as described in Haverick et al., MAbs. 2014 July-August:6(4): 852-8.

The melting temperature of the decoy IL-11 receptors is analysed by Differential scanning fluorimetry (DSF) as described in Menzen and Friess, J Pharm Sci. 2013 February; 102(2):415-28.

Example 8: Inhibition of Fibrosis In Vivo Using Decoy IL-11 Receptors

The therapeutic utility of the decoy IL-11 receptors is demonstrated in in vivo mouse models of fibrosis for various different tissues. The mice used in the experiments are wildtype (i.e. IL-11RA+/+) mice.

8.1 Heart Fibrosis

A pump is implanted, and mice are treated with AngII (2 mg/kg/day) for 28 days.

Decoy IL-11 receptors D11R1 or D11R2 are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with decoy IL-11 receptors have a reduced fibrotic response in heart tissue as compared to untreated/vehicle treated controls, as evidenced by reduced expression of markers of fibrosis.

8.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone. Decoy IL-11 receptors D11R1 or D11R2 are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using Trizol reagent (Invitrogen) and Qiagen TissueLyzer method followed by RNeasy column (Qiagen) purification. The cDNA is prepared using iScript™ cDNA synthesis kit, in which each reaction contained 1 μg of total RNA, as per the manufacturer's instructions. Quantitative RT-PCR gene expression analysis is performed on triplicate samples with either TaqMan (Applied Biosystems) or fast SYBR green (Qiagen) technology using StepOnePlus™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using Quickzyme Total Collagen assay kit (Quickzyme Biosciences) as per the manufacturer's instructions.

Mice treated with decoy IL-11 receptors have a reduced fibrotic response in kidney tissue as compared to untreated/vehicle treated controls, as evidenced by reduced expression of markers of fibrosis.

8.3 Lung Fibrosis

Mice are treated by intratracheal administration of bleomycin on day 0 to establish a fibrotic response in the lung (pulmonary fibrosis).

Decoy IL-11 receptors D11R1 or D11R2 are administered to different groups of mice by intravenous injection. Mice are sacrificed at day 21, and analysed for differences in fibrosis markers.

Mice treated with decoy IL-11 receptors have a reduced fibrotic response in lung tissue as compared to untreated/vehicle treated controls, as evidenced by reduced expression of markers of fibrosis.

8.4 Skin Fibrosis

Mice are treated by subcutaneous administration of bleomycin on day 0 to establish a fibrotic response in the skin.

Decoy IL-11 receptors D11R1 or D11R2 are administered to different groups of mice by intravenous injection. Mice are sacrificed at day 21, and analysed for differences in fibrosis markers.

Mice treated with decoy IL-11 receptors have a reduced fibrotic response in skin tissue as compared to untreated/vehicle treated controls, as evidenced by reduced expression of markers of fibrosis.

8.5 Eye Fibrosis

Mice undergo trabeculectomy procedure as described in Example 3.6 above to initiate a wound healing response in the eye.

Decoy IL-11 receptors D11R1 or D11R2 are administered to different groups of mice by intravenous injection, and fibrosis is monitored in the eye tissue.

Mice treated with decoy IL-11 receptors have a reduced fibrotic response in eye tissue as compared to untreated/vehicle treated controls, as evidenced by reduced expression of markers of fibrosis.

8.6 Other Tissues

The effect of treatment with decoy IL-11 receptors D11R1 or D11R2 on fibrosis is also analysed in mouse models of fibrosis for other tissues, such as the liver, kidney, bowel, and is also analysed in a model relevant to multiorgan (i.e. systemic) fibrosis.

The fibrotic response is measured and compared between mice treated with decoy IL-11 receptors and untreated mice, or vehicle treated controls. Mice treated with decoy IL-11 receptors have a reduced fibrotic response as compared to untreated/vehicle treated controls, as evidenced by reduced expression of markers of fibrosis.

Example 9: Treatment of Cancer In Vivo Using Decoy IL-11 Receptors

The effect of treatment with decoy IL-11 receptors D11R1 or D11R2 on cancer is analysed in mouse models of cancer.

Models of breast, lung, and gastrointestinal cancers are established in mice, the mice are treated by administration of decoy IL-11 receptors, and the development/progression of cancer is monitored.

An anti-cancer effect is observed for the decoy IL-11 receptors, as evidenced by reduced symptoms of cancer and/or increased survival as compared to untreated/vehicle treated controls.

Example 10: Treatment of AMD Using Decoy IL-11 Receptors

The effect of treatment with decoy IL-11 receptors D11R1 or D11R2 is investigated in wet age-related macular degeneration (AMD).

Decoy IL-11 receptors D11R1 or D11R2 are administered to subjects having wet AMD. In some treatment conditions, subjects are administered with VEGF antagonist therapy (e.g. ranibizumab, bevacizumab, pegaptanib, brolucizumab or aflibercept), PDGF antagonist therapy (e.g. pegpleranib), or are treated by laser coagulation therapy in addition to treatment with decoy IL-11 receptor.

A reduction in wet AMD pathology and/or improvement in the symptoms of wet AMD is observed in subjects treated with decoy IL-11 receptors as compared to subjects not treated with decoy IL-11 receptor.

---

The invention claimed is:

1. An IL-11 binding receptor which binds to IL-11 and inhibits IL-11-mediated signaling, comprising (i) the amino acid sequence of SEQ ID NO:19, and (ii) the amino acid sequence of SEQ ID NO:20.

2. The IL-11 binding receptor according to claim 1, which is capable of inhibiting interaction between: (i) IL-11 and gp130, and/or (ii) IL-11 and IL-11Rα.

3. The IL-11 binding receptor according to claim 1, wherein the IL-11 binding receptor comprises the amino acid sequence of SEQ ID NO: 1 or 2.

* * * * *

SEQUENCE LISTING

```
<160> NUMBER OF SEQ ID NOS: 28

<210> SEQ ID NO 1
<211> LENGTH: 594
<212> TYPE: PRT
<213> ORGANISM: Artificial Sequence
<220> FEATURE:
<223> OTHER INFORMATION: Decoy IL-11 Receptor 1 (D11R1):

<400> SEQUENCE: 1

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60
```

```
Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Ala Ser Gly Ile
305                 310                 315                 320

Thr Tyr Glu Asp Arg Pro Gly Gly Gly Ser Thr Arg Gly Gln Leu
                325                 330                 335

His Thr Gln Pro Glu Val Glu Pro Gln Val Asp Ser Pro Ala Pro Pro
            340                 345                 350

Arg Pro Ser Leu Gln Pro His Pro Arg Leu Leu Asp His Arg Asp Ser
        355                 360                 365

Val Glu Gln Val Ala Val Gly Ser Leu Gly Tyr Pro Pro Ala Arg Pro
    370                 375                 380

Val Val Ser Cys Gln Ala Ala Asp Tyr Glu Asn Phe Ser Cys Thr Trp
385                 390                 395                 400

Ser Pro Ser Gln Ile Ser Gly Leu Pro Thr Arg Tyr Leu Thr Ser Tyr
                405                 410                 415

Arg Lys Lys Thr Val Leu Gly Ala Asp Ser Gln Arg Arg Ser Pro Ser
            420                 425                 430

Thr Gly Pro Trp Pro Cys Pro Gln Asp Pro Leu Gly Ala Ala Arg Cys
        435                 440                 445

Val Val His Gly Ala Glu Phe Trp Ser Gln Tyr Arg Ile Asn Val Thr
    450                 455                 460

Glu Val Asn Pro Leu Gly Ala Ser Thr Arg Leu Leu Asp Val Ser Leu
465                 470                 475                 480

Gln Ser Ile Leu Arg Pro Asp Pro Pro Gln Gly Leu Arg Val Glu Ser
```

```
            485                 490                 495
Val Pro Gly Tyr Pro Arg Arg Leu Arg Ala Ser Trp Thr Tyr Pro Ala
            500                 505                 510

Ser Trp Pro Cys Gln Pro His Phe Leu Leu Lys Phe Arg Leu Gln Tyr
            515                 520                 525

Arg Pro Ala Gln His Pro Ala Trp Ser Thr Val Glu Pro Ala Gly Leu
            530                 535                 540

Glu Glu Val Ile Thr Asp Ala Val Ala Gly Leu Pro His Ala Val Arg
545                 550                 555                 560

Val Ser Ala Arg Asp Phe Leu Asp Ala Gly Thr Trp Ser Thr Trp Ser
            565                 570                 575

Pro Glu Ala Trp Gly Thr Pro Ser Thr Gly Asp Tyr Lys Asp Asp Asp
            580                 585                 590

Asp Lys

<210> SEQ ID NO 2
<211> LENGTH: 577
<212> TYPE: PRT
<213> ORGANISM: Artificial Sequence
<220> FEATURE:
<223> OTHER INFORMATION: Decoy IL-11 Receptor 2 (D11R2):

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
            85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
            115                 120                 125

Pro Lys Asn Leu Ser Cys Ile Val Asn Glu Gly Lys Lys Met Arg Cys
            130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
            165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
            210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
            245                 250                 255
```

```
Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Gly Gly Gly Ser Thr Arg Gly Ser Ala
                325                 330                 335

Gly Ser Gly Gly Ser Ala Thr Gly Ser Gly Ser Ala Ala Gly Ser Gly
            340                 345                 350

Asp Ser Val Arg Arg Gly Ser Leu Gly Tyr Pro Pro Ala Arg Pro Val
            355                 360                 365

Val Ser Cys Gln Ala Ala Asp Tyr Glu Asn Phe Ser Cys Thr Trp Ser
            370                 375                 380

Pro Ser Gln Ile Ser Gly Leu Pro Thr Arg Tyr Leu Thr Ser Tyr Arg
385                 390                 395                 400

Lys Lys Thr Val Leu Gly Ala Asp Ser Gln Arg Arg Ser Pro Ser Thr
                405                 410                 415

Gly Pro Trp Pro Cys Pro Gln Asp Pro Leu Gly Ala Ala Arg Cys Val
            420                 425                 430

Val His Gly Ala Glu Phe Trp Ser Gln Tyr Arg Ile Asn Val Thr Glu
            435                 440                 445

Val Asn Pro Leu Gly Ala Ser Thr Arg Leu Leu Asp Val Ser Leu Gln
        450                 455                 460

Ser Ile Leu Arg Pro Asp Pro Pro Gln Gly Leu Arg Val Glu Ser Val
465                 470                 475                 480

Pro Gly Tyr Pro Arg Arg Leu Arg Ala Ser Trp Thr Tyr Pro Ala Ser
                485                 490                 495

Trp Pro Cys Gln Pro His Phe Leu Leu Lys Phe Arg Leu Gln Tyr Arg
            500                 505                 510

Pro Ala Gln His Pro Ala Trp Ser Thr Val Glu Pro Ala Gly Leu Glu
            515                 520                 525

Glu Val Ile Thr Asp Ala Val Ala Gly Leu Pro His Ala Val Arg Val
        530                 535                 540

Ser Ala Arg Asp Phe Leu Asp Ala Gly Thr Trp Ser Thr Trp Ser Pro
545                 550                 555                 560

Glu Ala Trp Gly Thr Pro Ser Thr Gly Asp Tyr Lys Asp Asp Asp Asp
                565                 570                 575

Lys

<210> SEQ ID NO 3
<211> LENGTH: 22
<212> TYPE: PRT
<213> ORGANISM: Artificial Sequence
<220> FEATURE:
<223> OTHER INFORMATION: leader sequence

<400> SEQUENCE: 3

Met Leu Thr Leu Gln Thr Trp Leu Val Gln Ala Leu Phe Ile Phe Leu
1               5                   10                  15

Thr Thr Glu Ser Thr Gly
            20
```

<210> SEQ ID NO 4
<211> LENGTH: 304
<212> TYPE: PRT
<213> ORGANISM: Artificial Sequence
<220> FEATURE:
<223> OTHER INFORMATION: Sgp130 (D1, D2 and D3)

<400> SEQUENCE: 4

```
Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
    290                 295                 300
```

<210> SEQ ID NO 5
<211> LENGTH: 50
<212> TYPE: PRT
<213> ORGANISM: Artificial Sequence
<220> FEATURE:
<223> OTHER INFORMATION: Linker (50aa)

<400> SEQUENCE: 5

```
Gly Gly Gly Gly Ser Thr Arg Gly Gln Leu His Thr Gln Pro Glu Val
1               5                   10                  15
```

```
                Glu Pro Gln Val Asp Ser Pro Ala Pro Pro Arg Pro Ser Leu Gln Pro
                            20                  25                  30

His Pro Arg Leu Leu Asp His Arg Asp Ser Val Glu Gln Val Ala Val
                        35                  40                  45

Gly Ser
                    50

<210> SEQ ID NO 6
<211> LENGTH: 210
<212> TYPE: PRT
<213> ORGANISM: Artificial Sequence
<220> FEATURE:
<223> OTHER INFORMATION: IL-11Ralpha (D2 and D3)

<400> SEQUENCE: 6

Leu Gly Tyr Pro Pro Ala Arg Pro Val Val Ser Cys Gln Ala Ala Asp
1               5                   10                  15

Tyr Glu Asn Phe Ser Cys Thr Trp Ser Pro Ser Gln Ile Ser Gly Leu
            20                  25                  30

Pro Thr Arg Tyr Leu Thr Ser Tyr Arg Lys Lys Thr Val Leu Gly Ala
        35                  40                  45

Asp Ser Gln Arg Arg Ser Pro Ser Thr Gly Pro Trp Pro Cys Pro Gln
    50                  55                  60

Asp Pro Leu Gly Ala Ala Arg Cys Val Val His Gly Ala Glu Phe Trp
65                  70                  75                  80

Ser Gln Tyr Arg Ile Asn Val Thr Glu Val Asn Pro Leu Gly Ala Ser
                85                  90                  95

Thr Arg Leu Leu Asp Val Ser Leu Gln Ser Ile Leu Arg Pro Asp Pro
            100                 105                 110

Pro Gln Gly Leu Arg Val Glu Ser Val Pro Gly Tyr Pro Arg Arg Leu
        115                 120                 125

Arg Ala Ser Trp Thr Tyr Pro Ala Ser Trp Pro Cys Gln Pro His Phe
    130                 135                 140

Leu Leu Lys Phe Arg Leu Gln Tyr Arg Pro Ala Gln His Pro Ala Trp
145                 150                 155                 160

Ser Thr Val Glu Pro Ala Gly Leu Glu Glu Val Ile Thr Asp Ala Val
                165                 170                 175

Ala Gly Leu Pro His Ala Val Arg Val Ser Ala Arg Asp Phe Leu Asp
            180                 185                 190

Ala Gly Thr Trp Ser Thr Trp Ser Pro Glu Ala Trp Gly Thr Pro Ser
        195                 200                 205

Thr Gly
    210

<210> SEQ ID NO 7
<211> LENGTH: 8
<212> TYPE: PRT
<213> ORGANISM: Artificial Sequence
<220> FEATURE:
<223> OTHER INFORMATION: FLAG tag

<400> SEQUENCE: 7

Asp Tyr Lys Asp Asp Asp Asp Lys
1               5

<210> SEQ ID NO 8
<211> LENGTH: 33
<212> TYPE: PRT
```

<210> SEQ ID NO 8
<211> LENGTH: 33
<212> TYPE: PRT
<213> ORGANISM: Artificial Sequence
<220> FEATURE:
<223> OTHER INFORMATION: Linker (33aa)

<400> SEQUENCE: 8

Gly Gly Gly Gly Ser Thr Arg Gly Ser Ala Gly Ser Gly Ser Ala
1               5                   10                  15

Thr Gly Ser Gly Ser Ala Ala Gly Ser Gly Asp Ser Val Arg Arg Gly
            20                  25                  30

Ser

<210> SEQ ID NO 9
<211> LENGTH: 1809
<212> TYPE: DNA
<213> ORGANISM: Artificial Sequence
<220> FEATURE:
<223> OTHER INFORMATION: Decoy IL-11 Receptor 1 (D11R1):

<400> SEQUENCE: 9

```
gaattcccgc cgccaccatg ctgaccctgc agacatggct ggtgcaggcc ctgttcatct    60
tcctgaccac cgagagcacc ggcgagctgc tggatccttg cggctacatc agccccgaga   120
gccctgtggt gcagctgcat agcaacttca ccgccgtgtg cgtgctgaaa gaaaagtgca   180
tggactactt ccacgtgaac gccaactaca tcgtgtggaa aacaaaccac ttcaccatcc   240
ccaaagagca gtacaccatc atcaaccgga ccgccagcag cgtgaccttc accgatatcg   300
ccagcctgaa catccagctg acctgcaaca tcctgacctt cggccagctg gaacagaacg   360
tgtacggcat acaatcatc agcggcctgc ccccgagaa gcccaagaac ctgagctgca   420
tcgtgaacga gggcaagaaa atgagatgcg agtgggacgg cggcagagag acacacctgg   480
aaacaaactt caccctgaag tccgagtggg ccacccacaa gttcgccgac tgcaaggcca   540
agagggacac ccccaccagc tgtaccgtgg actacagcac cgtgtacttc gtgaacatcg   600
aagtgtgggt ggaagccgag aacgccctgg gcaaagtgac cagcgaccac atcaacttcg   660
accctgtgta caaagtgaag cccaacccc ccacaacct gagcgtgatc aacagcgagg   720
aactgagcag catcctgaag ctgacatgga ccaaccccag catcaagtcc gtgatcattc   780
tgaagtacaa catccagtac cggaccaagg acgccagcac ctggtcccag atcccccctg   840
aggataccgc ctccacccgg tccagcttca cagtgcagga cctgaagcct ttcaccgagt   900
acgtgttccg gatcagatgc atgaaggaag atggcaaggg ctactggagc gattggagcg   960
aggaagccag cggcatcacc tacgaggaca gacctggcgg cggaggctct acaagaggcc  1020
agctgcacac tcagcccgag gtggaacctc aggtggactc tcctgccct cctagaccta  1080 gcctgcagcc ccatcccaga ctgctggacc acagagacag cgtggaacag gtggccgtgg  1140
gcagcctggg atatcctcct gctagacccg tggtgtcctg ccaggccgcc gactacgaga  1200
acttctcctg cacatggtcc cccagccaga tctccggcct gcctaccaga tacctgacca  1260
gctaccggaa gaaaaccgtg ctgggcgccg acagccagaa gaagccct tctacaggcc  1320 cctggccctg ccctcaggat cctctgggag ctgccagatg tgtggtgcac ggcgccgagt  1380
tttggagcca gtacagaatc aacgtgaccg aagtgaaccc cctgggcgcc agcacaaggc  1440
tgctggacgt gtccctgcag agcatcctgc ggcctgatcc tccacaggga ctgcgggtgg  1500
aaagcgtgcc aggctacccc agaaggctga gagcctcctg acataccc gctagctggc  1560 cttgccagcc ccacttcctg ctgaagttcc ggctgcagta ccggccagcc cagcatccag  1620
cttggagcac agtggaacct gccggcctgg aagaagtgat cacagacgcc gtggccggac  1680
```

```
tgcctcatgc tgtgcgggtg tccgccagag actttctgga tgccggaacc tggtccactt    1740
ggagcccaga ggcttggggc acaccttcca ccggcgacta caaggacgac gacgacaagt    1800
gataagctt                                                            1809

<210> SEQ ID NO 10
<211> LENGTH: 1758
<212> TYPE: DNA
<213> ORGANISM: Artificial Sequence
<220> FEATURE:
<223> OTHER INFORMATION: Decoy IL-11 Receptor 2 (D11R2)

<400> SEQUENCE: 10
gaattcccgc cgccaccatg ctgaccctgc agacatggct ggtgcaggcc ctgttcatct      60
tcctgaccac cgagagcacc ggcgagctgc tggatccttg cggctacatc agccccgaga     120
gccctgtggt gcagctgcat agcaacttca ccgccgtgtg cgtgctgaaa gaaaagtgca     180
tggactactt ccacgtgaac gccaactaca tcgtgtggaa acaaaccac ttcaccatcc      240 ccaaagagca gtacaccatc atcaaccgga ccgccagcag cgtgaccttc accgatatcg     300
ccagcctgaa catccagctg acctgcaaca tcctgacctt cggccagctg aacagaacg      360 tgtacggcat cacaatcatc agcggcctgc ccccgagaa gcccaagaac ctgagctgca     420
tcgtgaacga gggcaagaaa atgagatgcg agtgggacgg cggcagagag acacacctgg     480
aaacaaactt caccctgaag tccgagtggg ccacccacaa gttcgccgac tgcaaggcca     540 agaggggacac ccccaccagc tgtaccgtgg actacagcac cgtgtacttc gtgaacatcg     600
aagtgtgggt ggaagccgag aacgccctgg gcaaagtgac cagcgaccac atcaacttcg     660
accctgtgta caaagtgaag cccaaccccc cccacaacct gagcgtgatc aacagcgagg     720
aactgagcag catcctgaag ctgacatgga ccaaccccca tcaagtcc gtgatcattc      780 tgaagtacaa catccagtac cggaccaagg acgccagcac ctggtcccag atccccctg     840 aggataccgc ctccaccgg tccagcttca cagtgcagga cctgaagcct ttcaccgagt      900
acgtgttccg gatcagatgc atgaaggaag atgcaaggg ctactggagc gattggagcg      960
aggaagccag cggcatcacc tacgaggaca gacctggcgg cggaggcagc acaagaggat    1020
ctgctggaag cggcggaagc gccacaggct ctggatctgc agctggcagc ggagactctg    1080
tgcggagagg ctctctgggc taccctcctg ctagacccgt ggtgtcttgt caggccgccg    1140
actacgagaa cttcagctgc acatggtccc ccagccagat ctccggcctg cctaccagat    1200
acctgaccag ctaccggaag aaaaccgtgc tgggcgccga cagccagaga agaagccctt    1260
ctacaggccc ctggccctgc cctcaggatc ctctggagc tgccagatgt gtggtgcacg    1320
gcgccgagtt ttggagccag tacagaatca acgtgaccga agtgaacccc ctgggcgcca    1380
gcactagact gctggatgtg tccctgcaga gcatcctgcg gcccgatcct ccacagggac    1440
tgagagtgga aagcgtgccc ggctacccca aaggctgag agcctcctgg acataccccg    1500
ctagctggcc ttgccagccc cacttcctgc tgaagtttcg gctgcagtac cggccagccc    1560
agcaccctgc ttggagcaca gtggaacctg ccggcctgga agaagtgatc acagacgccg    1620
tggccggact gcctcatgct gtgcgggtgt ccgccagaga ctttctggat gccggaacct    1680
ggtccacttg gagccctgag gcttggggca caccttccac cggcgactac aaggacgacg    1740
acgacaagtg ataagctt                                                  1758

<210> SEQ ID NO 11
```

```
<211> LENGTH: 66
<212> TYPE: DNA
<213> ORGANISM: Artificial Sequence
<220> FEATURE:
<223> OTHER INFORMATION: Leader sequence

<400> SEQUENCE: 11
atgctgaccc tgcagacatg gctggtgcag gccctgttca tcttcctgac caccgagagc      60
accggc                                                                 66

<210> SEQ ID NO 12
<211> LENGTH: 912
<212> TYPE: DNA
<213> ORGANISM: Artificial Sequence
<220> FEATURE:
<223> OTHER INFORMATION: Sgp130 (D1, D2 and D3)

<400> SEQUENCE: 12
gagctgctgg atccttgcgg ctacatcagc cccgagagcc tgtggtgca gctgcatagc       60 aacttcaccg ccgtgtgcgt gctgaaagaa aagtgcatgg actacttcca cgtgaacgcc     120
aactacatcg tgtggaaaac aaaccacttc accatcccca agagcagta caccatcatc      180 aaccggaccc ccagcagcgt gaccttcacc gatatcgcca gcctgaacat ccagctgacc     240
tgcaacatcc tgaccttcgg ccagctggaa cagaacgtgt acggcatcac aatcatcagc     300
ggcctgcccc ccgagaagcc caagaacctg agctgcatcg tgaacgaggg caagaaaatg     360
agatgcgagt gggacggcgg cagagagaca cacctggaaa caaacttcac cctgaagtcc     420
gagtgggcca cccacaagtt cgccgactgc aaggccaaga gggacacccc caccagctgt     480
accgtggact acagcaccgt gtacttcgtg aacatcgaag tgtgggtgga agccgagaac     540
gccctgggca aagtgaccag cgaccacatc aacttcgacc ctgtgtacaa agtgaagccc     600 aaccccccc acaacctgag cgtgatcaac agcgaggaac tgagcagcat cctgaagctg     660
acatggacca cccccagcat caagtccgtg atcattctga agtacaacat ccagtaccgg     720
accaaggacg ccagcaccctg gtcccagatc cccctgagg ataccgcctc cacccggtcc     780
agcttcacag tgcaggacct gaagcctttc accgagtacg tgttccggat cagatgcatg     840
aaggaagatg gcaagggcta ctggagcgat tggagcgagg aagccagcgg catcacctac     900
gaggacagac ct                                                         912

<210> SEQ ID NO 13
<211> LENGTH: 150
<212> TYPE: DNA
<213> ORGANISM: Artificial Sequence
<220> FEATURE:
<223> OTHER INFORMATION: Linker (50aa)

<400> SEQUENCE: 13
ggcggcggag gctctacaag aggccagctg cacactcagc ccgaggtgga acctcaggtg      60
gactctcctg cccctcctag acctagcctg cagccccatc ccagactgct ggaccacaga     120
gacagcgtgg aacaggtggc cgtgggcagc                                      150

<210> SEQ ID NO 14
<211> LENGTH: 630
<212> TYPE: DNA
<213> ORGANISM: Artificial Sequence
<220> FEATURE:
<223> OTHER INFORMATION: IL-11Ralpha (D2 and D3)

<400> SEQUENCE: 14
```

```
ctgggatatc ctcctgctag acccgtggtg tcctgccagg ccgccgacta cgagaacttc      60
tcctgcacat ggtcccccag ccagatctcc ggcctgccta ccagatacct gaccagctac     120
cggaagaaaa ccgtgctggg cgccgacagc cagagaagaa gcccttctac aggcccctgg     180
ccctgccctc aggatcctct gggagctgcc agatgtgtgg tgcacggcgc cgagttttgg     240
agccagtaca gaatcaacgt gaccgaagtg aaccccctgg gcgccagcac aaggctgctg     300
gacgtgtccc tgcagagcat cctgcggcct gatcctccac agggactgcg ggtggaaagc     360
gtgccaggct accccagaag gctgagagcc tcctggacat ccccgctagc tggccttgc      420 cagccccact tcctgctgaa gttccggctg cagtaccggc cagcccagca tccagcttgg     480
agcacagtgg aacctgccgg cctggaagaa gtgatcacag cgccgtggc cggactgcct      540 catgctgtgc gggtgtccgc cagagacttt ctggatgccg aacctggtc cacttggagc      600 ccagaggctt ggggcacacc ttccaccggc                                      630
```

```
<210> SEQ ID NO 15
<211> LENGTH: 24
<212> TYPE: DNA
<213> ORGANISM: Artificial Sequence
<220> FEATURE:
<223> OTHER INFORMATION: FLAG tag

<400> SEQUENCE: 15
gactacaagg acgacgacga caag                                             24

<210> SEQ ID NO 16
<211> LENGTH: 99
<212> TYPE: DNA
<213> ORGANISM: Artificial Sequence
<220> FEATURE:
<223> OTHER INFORMATION: Linker (33aa)

<400> SEQUENCE: 16
ggcggcggag gcagcacaag aggatctgct ggaagcggcg gaagcgccac aggctctgga      60
tctgcagctg gcagcggaga ctctgtgcgg agaggctct                             99

<210> SEQ ID NO 17
<211> LENGTH: 918
<212> TYPE: PRT
<213> ORGANISM: Artificial Sequence
<220> FEATURE:
<223> OTHER INFORMATION: Human gp130 (Genbank accession no. NP_002175.2)

<400> SEQUENCE: 17
```

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

-continued

Gln Asn Val Tyr Gly Ile Thr Ile Ser Gly Leu Pro Glu Lys
    115                 120                 125
Pro Lys Asn Leu Ser Cys Ile Val Asn Glu Gly Lys Lys Met Arg Cys
130                 135                 140
Glu Trp Asp Gly Gly Arg Glu Thr His Leu Glu Thr Asn Phe Thr Leu
145                 150                 155                 160
Lys Ser Glu Trp Ala Thr His Lys Phe Ala Asp Cys Lys Ala Lys Arg
                165                 170                 175
Asp Thr Pro Thr Ser Cys Thr Val Asp Tyr Ser Thr Val Tyr Phe Val
                180                 185                 190
Asn Ile Glu Val Trp Val Glu Ala Glu Asn Ala Leu Gly Lys Val Thr
                195                 200                 205
Ser Asp His Ile Asn Phe Asp Pro Val Tyr Lys Val Lys Pro Asn Pro
    210                 215                 220
Pro His Asn Leu Ser Val Ile Asn Ser Glu Glu Leu Ser Ser Ile Leu
225                 230                 235                 240
Lys Leu Thr Trp Thr Asn Pro Ser Ile Lys Ser Val Ile Ile Leu Lys
                245                 250                 255
Tyr Asn Ile Gln Tyr Arg Thr Lys Asp Ala Ser Thr Trp Ser Gln Ile
                260                 265                 270
Pro Pro Glu Asp Thr Ala Ser Thr Arg Ser Ser Phe Thr Val Gln Asp
                275                 280                 285
Leu Lys Pro Phe Thr Glu Tyr Val Phe Arg Ile Arg Cys Met Lys Glu
                290                 295                 300
Asp Gly Lys Gly Tyr Trp Ser Asp Trp Ser Glu Ala Ser Gly Ile
305                 310                 315                 320
Thr Tyr Glu Asp Arg Pro Ser Lys Ala Pro Ser Phe Trp Tyr Lys Ile
                325                 330                 335
Asp Pro Ser His Thr Gln Gly Tyr Arg Thr Val Gln Leu Val Trp Lys
                340                 345                 350
Thr Leu Pro Pro Phe Glu Ala Asn Gly Lys Ile Leu Asp Tyr Glu Val
    355                 360                 365
Thr Leu Thr Arg Trp Lys Ser His Leu Gln Asn Tyr Thr Val Asn Ala
    370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
                405                 410                 415
Pro Ala Cys Asp Phe Gln Ala Thr His Pro Val Met Asp Leu Lys Ala
                420                 425                 430
Phe Pro Lys Asp Asn Met Leu Trp Val Glu Trp Thr Thr Pro Arg Glu
    435                 440                 445
Ser Val Lys Lys Tyr Ile Leu Glu Trp Cys Val Leu Ser Asp Lys Ala
    450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                485                 490                 495
Thr Pro Val Tyr Ala Asp Gly Pro Gly Ser Pro Glu Ser Ile Lys Ala
                500                 505                 510
Tyr Leu Lys Gln Ala Pro Pro Ser Lys Gly Pro Thr Val Arg Thr Lys
    515                 520                 525

```
Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
            915

<210> SEQ ID NO 18
<211> LENGTH: 422
<212> TYPE: PRT
```

<213> ORGANISM: Artificial Sequence
<220> FEATURE:
<223> OTHER INFORMATION: Human IL-11Ralpha (Genbank accession no.
      NP_001136256.1; UniProt Q14626):

<400> SEQUENCE: 18

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
            340                 345                 350

His Pro Arg Leu Leu Asp His Arg Asp Ser Val Glu Gln Val Ala Val
        355                 360                 365

Leu Ala Ser Leu Gly Ile Leu Ser Phe Leu Gly Leu Val Ala Gly Ala
    370                 375                 380

```
Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
            405                 410                 415

Pro Gly Ala Pro Asn Leu
            420

<210> SEQ ID NO 19
<211> LENGTH: 296
<212> TYPE: PRT
<213> ORGANISM: Artificial Sequence
<220> FEATURE:
<223> OTHER INFORMATION: The cytokine binding module of human gp130
      corresponds to positions 26 to 321 of human gp130 (Genbank
      accession no. NP_002175.2)

<400> SEQUENCE: 19

Asp Pro Cys Gly Tyr Ile Ser Pro Glu Ser Pro Val Val Gln Leu His
1               5                   10                  15

Ser Asn Phe Thr Ala Val Cys Val Leu Lys Glu Lys Cys Met Asp Tyr
            20                  25                  30

Phe His Val Asn Ala Asn Tyr Ile Val Trp Lys Thr Asn His Phe Thr
        35                  40                  45

Ile Pro Lys Glu Gln Tyr Thr Ile Ile Asn Arg Thr Ala Ser Ser Val
50                  55                  60

Thr Phe Thr Asp Ile Ala Ser Leu Asn Ile Gln Leu Thr Cys Asn Ile
65                  70                  75                  80

Leu Thr Phe Gly Gln Leu Glu Gln Asn Val Tyr Gly Ile Thr Ile Ile
                85                  90                  95

Ser Gly Leu Pro Pro Glu Lys Pro Lys Asn Leu Ser Cys Ile Val Asn
            100                 105                 110

Glu Gly Lys Lys Met Arg Cys Glu Trp Asp Gly Gly Arg Glu Thr His
        115                 120                 125

Leu Glu Thr Asn Phe Thr Leu Lys Ser Glu Trp Ala Thr His Lys Phe
    130                 135                 140

Ala Asp Cys Lys Ala Lys Arg Asp Thr Pro Thr Ser Cys Thr Val Asp
145                 150                 155                 160

Tyr Ser Thr Val Tyr Phe Val Asn Ile Glu Val Trp Val Glu Ala Glu
                165                 170                 175

Asn Ala Leu Gly Lys Val Thr Ser Asp His Ile Asn Phe Asp Pro Val
            180                 185                 190

Tyr Lys Val Lys Pro Asn Pro Pro His Asn Leu Ser Val Ile Asn Ser
        195                 200                 205

Glu Glu Leu Ser Ser Ile Leu Lys Leu Thr Trp Thr Asn Pro Ser Ile
    210                 215                 220

Lys Ser Val Ile Ile Leu Lys Tyr Asn Ile Gln Tyr Arg Thr Lys Asp
225                 230                 235                 240

Ala Ser Thr Trp Ser Gln Ile Pro Pro Glu Asp Thr Ala Ser Thr Arg
                245                 250                 255

Ser Ser Phe Thr Val Gln Asp Leu Lys Pro Phe Thr Glu Tyr Val Phe
            260                 265                 270

Arg Ile Arg Cys Met Lys Glu Asp Gly Lys Gly Tyr Trp Ser Asp Trp
        275                 280                 285

Ser Glu Glu Ala Ser Gly Ile Thr
    290                 295
```

<210> SEQ ID NO 20
<211> LENGTH: 206
<212> TYPE: PRT
<213> ORGANISM: Artificial Sequence
<220> FEATURE:
<223> OTHER INFORMATION: The cytokine binding module of human
      IL-11Ralpha corresponds to positions 112 to 317 of human
      IL-11Ralpha (Genbank accession no. NP_001136256.1; UniProt Q14626)

<400> SEQUENCE: 20

```
Pro Pro Ala Arg Pro Val Val Ser Cys Gln Ala Ala Asp Tyr Glu Asn
1               5                   10                  15

Phe Ser Cys Thr Trp Ser Pro Ser Gln Ile Ser Gly Leu Pro Thr Arg
            20                  25                  30

Tyr Leu Thr Ser Tyr Arg Lys Lys Thr Val Leu Gly Ala Asp Ser Gln
        35                  40                  45

Arg Arg Ser Pro Ser Thr Gly Pro Trp Pro Cys Pro Gln Asp Pro Leu
50                  55                  60

Gly Ala Ala Arg Cys Val Val His Gly Ala Glu Phe Trp Ser Gln Tyr
65                  70                  75                  80

Arg Ile Asn Val Thr Glu Val Asn Pro Leu Gly Ala Ser Thr Arg Leu
                85                  90                  95

Leu Asp Val Ser Leu Gln Ser Ile Leu Arg Pro Asp Pro Pro Gln Gly
            100                 105                 110

Leu Arg Val Glu Ser Val Pro Gly Tyr Pro Arg Arg Leu Arg Ala Ser
        115                 120                 125

Trp Thr Tyr Pro Ala Ser Trp Pro Cys Gln Pro His Phe Leu Leu Lys
130                 135                 140

Phe Arg Leu Gln Tyr Arg Pro Ala Gln His Pro Ala Trp Ser Thr Val
145                 150                 155                 160

Glu Pro Ala Gly Leu Glu Glu Val Ile Thr Asp Ala Val Ala Gly Leu
                165                 170                 175

Pro His Ala Val Arg Val Ser Ala Arg Asp Phe Leu Asp Ala Gly Thr
            180                 185                 190

Trp Ser Thr Trp Ser Pro Glu Ala Trp Gly Thr Pro Ser Thr
        195                 200                 205
```

<210> SEQ ID NO 21
<211> LENGTH: 1575
<212> TYPE: DNA
<213> ORGANISM: Artificial Sequence
<220> FEATURE:
<223> OTHER INFORMATION: DNA encoding IL-11:IL-11Ralpha fusion protein

<400> SEQUENCE: 21

```
gaattcccgc cgccaccatg ggctggtcct gcatcatcct gtttctggtg gccacagcca      60
ccggcgtgca ctctccacag gcttgggacc tccaggcgt gcagtatggc cagcctggca     120
gatccgtgaa gctgtgctgt cctggcgtga cagctggcga ccctgtgtcc tggttcagag     180
atggcgagcc caagctgctg cagggcccag attctggact gggccacgaa ctggtgctgg     240
cccaggccga ttctaccgac gagggcacct acatctgcca gaccctggat ggcgccctgg     300
gcggaacagt gacactgcag ctgggctacc ctcccgccag acctgtggtg tcttgtcagg     360
ccgccgacta cgagaacttc agctgcacat ggtccccag ccagatcagc ggcctgccca     420
ccagataccc tgaccagcta cggaagaaaa ccgtgctggg cgccgacagc cagagaagaa     480
gcccttctac aggccctgg ccctgccctc aggatcctct gggagctgcc agatgtgtgg     540
tgcacggcgc cgagttctgg tcccagtacc ggatcaacgt gaccgaagtg aacccccctgg     600
```

```
gcgcctccac aagactgctg gatgtgtccc tgcagagcat cctgcggccc gatcctccac      660
agggcctgag agtggaaagc gtgcccggct accccagaag gctgagagcc agctggacat      720
accccgcctc ttggccttgc cagccccact tcctgctgaa gtttcggctg cagtaccggc      780
cagcccagca ccctgcttgg agcacagtgg aacctgccgg cctggaagaa gtgatcacag      840
acgccgtggc cggactgcct catgctgtgc gggtgtccgc cagagacttt ctggatgccg      900
gcacctggtc tacctggtcc ccagaagcct ggggcacacc ttctactggc ggacctgctg      960
gacagtctgg cggaggcgga ggaagtggcg gaggatcagg gggaggatct gtgcctggac      1020
ctcctccagg accccctaga gtgtccccag atcctagggc cgagctggac tctaccgtgc      1080
tgctgaccag atccctgctg ccgacacaa ggcagctggc tgcccagctg agagacaagt       1140
tccccgccga cggcgaccac aacctggata gcctgcctac cctggccatg tctgctggcg      1200
cactgggggc tctgcagctg cctggggtgc tgactagact gagagccgac ctgctgagct      1260
acctgcggca tgtgcagtgg ctgagaaggg ctggcggcag cagcctgaaa accctggaac      1320
ctgagctggg cacactgcag gccagactgg acagactgct gcgcagactg cagctgctga      1380
tgagcagact ggctctgccc cagcctcctc ctgaccctcc tgctcctcca ctggctcctc      1440
caagctctgc ttggggcgga attagagccg cccacgccat tctgggaggc ctgcacctga      1500
cactggattg ggcagtgcgg ggcctgctgc tgctgaaaac cagactgcac caccaccatc      1560
accactgata agctt                                                      1575
```

<210> SEQ ID NO 22
<211> LENGTH: 516
<212> TYPE: PRT
<213> ORGANISM: Artificial Sequence
<220> FEATURE:
<223> OTHER INFORMATION: Amino acid sequence of IL-11:IL-11Ralpha fusion
      protein

<400> SEQUENCE: 22

```
Met Gly Trp Ser Cys Ile Ile Leu Phe Leu Val Ala Thr Ala Thr Gly
1               5                   10                  15

Val His Ser Pro Gln Ala Trp Gly Pro Gly Val Gln Tyr Gly Gln
            20                  25                  30

Pro Gly Arg Ser Val Lys Leu Cys Cys Pro Gly Val Thr Ala Gly Asp
        35                  40                  45

Pro Val Ser Trp Phe Arg Asp Gly Glu Pro Lys Leu Leu Gln Gly Pro
    50                  55                  60

Asp Ser Gly Leu Gly His Glu Leu Val Leu Ala Gln Ala Asp Ser Thr
65                  70                  75                  80

Asp Glu Gly Thr Tyr Ile Cys Gln Thr Leu Asp Gly Ala Leu Gly Gly
                85                  90                  95

Thr Val Thr Leu Gln Leu Gly Tyr Pro Pro Ala Arg Pro Val Val Ser
            100                 105                 110

Cys Gln Ala Ala Asp Tyr Glu Asn Phe Ser Cys Thr Trp Ser Pro Ser
        115                 120                 125

Gln Ile Ser Gly Leu Pro Thr Arg Tyr Leu Thr Ser Tyr Arg Lys Lys
    130                 135                 140

Thr Val Leu Gly Ala Asp Ser Gln Arg Arg Ser Pro Ser Thr Gly Pro
145                 150                 155                 160

Trp Pro Cys Pro Gln Asp Pro Leu Gly Ala Ala Arg Cys Val Val His
                165                 170                 175
```

Gly Ala Glu Phe Trp Ser Gln Tyr Arg Ile Asn Val Thr Glu Val Asn
            180                 185                 190

Pro Leu Gly Ala Ser Thr Arg Leu Leu Asp Val Ser Leu Gln Ser Ile
        195                 200                 205

Leu Arg Pro Asp Pro Pro Gln Gly Leu Arg Val Glu Ser Val Pro Gly
210                 215                 220

Tyr Pro Arg Arg Leu Arg Ala Ser Trp Thr Tyr Pro Ala Ser Trp Pro
225                 230                 235                 240

Cys Gln Pro His Phe Leu Leu Lys Phe Arg Leu Gln Tyr Arg Pro Ala
            245                 250                 255

Gln His Pro Ala Trp Ser Thr Val Glu Pro Ala Gly Leu Glu Glu Val
        260                 265                 270

Ile Thr Asp Ala Val Ala Gly Leu Pro His Ala Val Arg Val Ser Ala
    275                 280                 285

Arg Asp Phe Leu Asp Ala Gly Thr Trp Ser Thr Trp Ser Pro Glu Ala
290                 295                 300

Trp Gly Thr Pro Ser Thr Gly Pro Ala Gly Gln Ser Gly Gly Gly Gly
305                 310                 315                 320

Gly Gly Ser Gly Gly Gly Ser Gly Gly Gly Ser Val Pro Gly Pro Pro
            325                 330                 335

Pro Gly Pro Pro Arg Val Ser Pro Asp Pro Arg Ala Glu Leu Asp Ser
        340                 345                 350

Thr Val Leu Leu Thr Arg Ser Leu Leu Ala Asp Thr Arg Gln Leu Ala
    355                 360                 365

Ala Gln Leu Arg Asp Lys Phe Pro Ala Asp Gly Asp His Asn Leu Asp
370                 375                 380

Ser Leu Pro Thr Leu Ala Met Ser Ala Gly Ala Leu Gly Ala Leu Gln
385                 390                 395                 400

Leu Pro Gly Val Leu Thr Arg Leu Arg Ala Asp Leu Leu Ser Tyr Leu
            405                 410                 415

Arg His Val Gln Trp Leu Arg Arg Ala Gly Gly Ser Ser Leu Lys Thr
        420                 425                 430

Leu Glu Pro Glu Leu Gly Thr Leu Gln Ala Arg Leu Asp Arg Leu Leu
    435                 440                 445

Arg Arg Leu Gln Leu Leu Met Ser Arg Leu Ala Leu Pro Gln Pro Pro
450                 455                 460

Pro Asp Pro Pro Ala Pro Pro Leu Ala Pro Pro Ser Ser Ala Trp Gly
465                 470                 475                 480

Gly Ile Arg Ala Ala His Ala Ile Leu Gly Gly Leu His Leu Thr Leu
            485                 490                 495

Asp Trp Ala Val Arg Gly Leu Leu Leu Leu Lys Thr Arg Leu His His
        500                 505                 510

His His His His
        515

<210> SEQ ID NO 23
<211> LENGTH: 595
<212> TYPE: PRT
<213> ORGANISM: Artificial Sequence
<220> FEATURE:
<223> OTHER INFORMATION: Mouse gp130 ECD

<400> SEQUENCE: 23

Gln Leu Leu Glu Pro Cys Gly Tyr Ile Tyr Pro Glu Phe Pro Val Val
1               5                   10                  15

Gln Arg Gly Ser Asn Phe Thr Ala Ile Cys Val Leu Lys Glu Ala Cys
            20                  25                  30

Leu Gln His Tyr Tyr Val Asn Ala Ser Tyr Ile Val Trp Lys Thr Asn
        35                  40                  45

His Ala Ala Val Pro Arg Glu Gln Val Thr Val Ile Asn Arg Thr Thr
50                  55                  60

Ser Ser Val Thr Phe Thr Asp Val Val Leu Pro Ser Val Gln Leu Thr
65                  70                  75                  80

Cys Asn Ile Leu Ser Phe Gly Gln Ile Glu Gln Asn Val Tyr Gly Val
                85                  90                  95

Thr Met Leu Ser Gly Phe Pro Pro Asp Lys Pro Thr Asn Leu Thr Cys
            100                 105                 110

Ile Val Asn Glu Gly Lys Asn Met Leu Cys Gln Trp Asp Pro Gly Arg
        115                 120                 125

Glu Thr Tyr Leu Glu Thr Asn Tyr Thr Leu Lys Ser Glu Trp Ala Thr
130                 135                 140

Glu Lys Phe Pro Asp Cys Gln Ser Lys His Gly Thr Ser Cys Met Val
145                 150                 155                 160

Ser Tyr Met Pro Thr Tyr Tyr Val Asn Ile Glu Val Trp Val Glu Ala
                165                 170                 175

Glu Asn Ala Leu Gly Lys Val Ser Ser Glu Ser Ile Asn Phe Asp Pro
            180                 185                 190

Val Asp Lys Val Lys Pro Thr Pro Pro Tyr Asn Leu Ser Val Thr Asn
        195                 200                 205

Ser Glu Glu Leu Ser Ser Ile Leu Lys Leu Ser Trp Val Ser Ser Gly
210                 215                 220

Leu Gly Gly Leu Leu Asp Leu Lys Ser Asp Ile Gln Tyr Arg Thr Lys
225                 230                 235                 240

Asp Ala Ser Thr Trp Ile Gln Val Pro Leu Glu Asp Thr Met Ser Pro
                245                 250                 255

Arg Thr Ser Phe Thr Val Gln Asp Leu Lys Pro Phe Thr Glu Tyr Val
            260                 265                 270

Phe Arg Ile Arg Ser Ile Lys Asp Ser Gly Lys Gly Tyr Trp Ser Asp
        275                 280                 285

Trp Ser Glu Glu Ala Ser Gly Thr Thr Tyr Glu Asp Arg Pro Ser Arg
290                 295                 300

Pro Pro Ser Phe Trp Tyr Lys Thr Asn Pro Ser His Gly Gln Glu Tyr
305                 310                 315                 320

Arg Ser Val Arg Leu Ile Trp Lys Ala Leu Pro Leu Ser Glu Ala Asn
                325                 330                 335

Gly Lys Ile Leu Asp Tyr Glu Val Ile Leu Thr Gln Ser Lys Ser Val
            340                 345                 350

Ser Gln Thr Tyr Thr Val Thr Gly Thr Glu Leu Thr Val Asn Leu Thr
        355                 360                 365

Asn Asp Arg Tyr Val Ala Ser Leu Ala Ala Arg Asn Lys Val Gly Lys
370                 375                 380

Ser Ala Ala Ala Val Leu Thr Ile Pro Ser Pro His Val Thr Ala Ala
385                 390                 395                 400

Tyr Ser Val Val Asn Leu Lys Ala Phe Pro Lys Asp Asn Leu Leu Trp
                405                 410                 415

Val Glu Trp Thr Pro Pro Pro Lys Pro Val Ser Lys Tyr Ile Leu Glu
            420                 425                 430

Trp Cys Val Leu Ser Glu Asn Ala Pro Cys Val Glu Asp Trp Gln Gln

```
                    435                 440                 445
Glu Asp Ala Thr Val Asn Arg Thr His Leu Arg Gly Arg Leu Leu Glu
    450                 455                 460

Ser Lys Cys Tyr Gln Ile Thr Val Thr Pro Val Phe Ala Thr Gly Pro
465                 470                 475                 480

Gly Gly Ser Glu Ser Leu Lys Ala Tyr Leu Lys Gln Ala Ala Pro Ala
                485                 490                 495

Arg Gly Pro Thr Val Arg Thr Lys Lys Val Gly Lys Asn Glu Ala Val
            500                 505                 510

Leu Ala Trp Asp Gln Ile Pro Val Asp Asp Gln Asn Gly Phe Ile Arg
        515                 520                 525

Asn Tyr Ser Ile Ser Tyr Arg Thr Ser Val Gly Lys Glu Met Val Val
    530                 535                 540

His Val Asp Ser Ser His Thr Glu Tyr Thr Leu Ser Ser Leu Ser Ser
545                 550                 555                 560

Asp Thr Leu Tyr Met Val Arg Met Ala Ala Tyr Thr Asp Glu Gly Gly
                565                 570                 575

Lys Asp Gly Pro Glu Phe Thr Phe Thr Thr Pro Lys Phe Ala Gln Gly
            580                 585                 590

Glu Ile Glu
        595

<210> SEQ ID NO 24
<211> LENGTH: 597
<212> TYPE: PRT
<213> ORGANISM: Artificial Sequence
<220> FEATURE:
<223> OTHER INFORMATION: Human gp130 ECD

<400> SEQUENCE: 24

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
```

```
            195                 200                 205
Ile Asn Ser Glu Glu Leu Ser Ser Ile Leu Lys Leu Thr Trp Thr Asn
210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
    290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
    370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
        435                 440                 445

Gln Gln Glu Asp Gly Thr Val His Arg Thr Tyr Leu Arg Gly Asn Leu
    450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
        515                 520                 525

Ile Arg Asn Tyr Thr Ile Phe Tyr Arg Thr Ile Ile Gly Asn Glu Thr
    530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575

Gly Gly Lys Asp Gly Pro Glu Phe Thr Phe Thr Thr Pro Lys Phe Ala
            580                 585                 590

Gln Gly Glu Ile Glu
        595

<210> SEQ ID NO 25
```

```
<211> LENGTH: 294
<212> TYPE: PRT
<213> ORGANISM: Artificial Sequence
<220> FEATURE:
<223> OTHER INFORMATION: Mouse gp130 D1-D3

<400> SEQUENCE: 25

Glu Pro Cys Gly Tyr Ile Tyr Pro Glu Phe Pro Val Val Gln Arg Gly
1               5                   10                  15

Ser Asn Phe Thr Ala Ile Cys Val Leu Lys Glu Ala Cys Leu Gln His
            20                  25                  30

Tyr Tyr Val Asn Ala Ser Tyr Ile Val Trp Lys Thr Asn His Ala Ala
        35                  40                  45

Val Pro Arg Glu Gln Val Thr Val Ile Asn Arg Thr Thr Ser Ser Val
50                  55                  60

Thr Phe Thr Asp Val Val Leu Pro Ser Val Gln Leu Thr Cys Asn Ile
65                  70                  75                  80

Leu Ser Phe Gly Gln Ile Glu Gln Asn Val Tyr Gly Val Thr Met Leu
                85                  90                  95

Ser Gly Phe Pro Pro Asp Lys Pro Thr Asn Leu Thr Cys Ile Val Asn
            100                 105                 110

Glu Gly Lys Asn Met Leu Cys Gln Trp Asp Pro Gly Arg Glu Thr Tyr
        115                 120                 125

Leu Glu Thr Asn Tyr Thr Leu Lys Ser Glu Trp Ala Thr Glu Lys Phe
130                 135                 140

Pro Asp Cys Gln Ser Lys His Gly Thr Ser Cys Met Val Ser Tyr Met
145                 150                 155                 160

Pro Thr Tyr Tyr Val Asn Ile Glu Val Trp Val Glu Ala Glu Asn Ala
                165                 170                 175

Leu Gly Lys Val Ser Ser Glu Ser Ile Asn Phe Asp Pro Val Asp Lys
            180                 185                 190

Val Lys Pro Thr Pro Pro Tyr Asn Leu Ser Val Thr Asn Ser Glu Glu
        195                 200                 205

Leu Ser Ser Ile Leu Lys Leu Ser Trp Val Ser Ser Gly Leu Gly Gly
210                 215                 220

Leu Leu Asp Leu Lys Ser Asp Ile Gln Tyr Arg Thr Lys Asp Ala Ser
225                 230                 235                 240

Thr Trp Ile Gln Val Pro Leu Glu Asp Thr Met Ser Pro Arg Thr Ser
                245                 250                 255

Phe Thr Val Gln Asp Leu Lys Pro Phe Thr Glu Tyr Val Phe Arg Ile
            260                 265                 270

Arg Ser Ile Lys Asp Ser Gly Lys Gly Tyr Trp Ser Asp Trp Ser Glu
        275                 280                 285

Glu Ala Ser Gly Thr Thr
    290

<210> SEQ ID NO 26
<211> LENGTH: 350
<212> TYPE: PRT
<213> ORGANISM: Artificial Sequence
<220> FEATURE:
<223> OTHER INFORMATION: Mouse IL-11Ra ECD

<400> SEQUENCE: 26

Ser Ser Pro Cys Pro Gln Ala Trp Gly Pro Pro Gly Val Gln Tyr Gly
1               5                   10                  15

Gln Pro Gly Arg Pro Val Met Leu Cys Cys Pro Gly Val Ser Ala Gly
```

```
                    20                  25                  30
Thr Pro Val Ser Trp Phe Arg Asp Gly Asp Ser Arg Leu Leu Gln Gly
                35                  40                  45
Pro Asp Ser Gly Leu Gly His Arg Leu Val Leu Ala Gln Val Asp Ser
            50                  55                  60
Pro Asp Glu Gly Thr Tyr Val Cys Gln Thr Leu Asp Gly Val Ser Gly
65                  70                  75                  80
Gly Met Val Thr Leu Lys Leu Gly Phe Pro Pro Ala Arg Pro Glu Val
                85                  90                  95
Ser Cys Gln Ala Val Asp Tyr Glu Asn Phe Ser Cys Thr Trp Ser Pro
            100                 105                 110
Gly Gln Val Ser Gly Leu Pro Thr Arg Tyr Leu Thr Ser Tyr Arg Lys
        115                 120                 125
Lys Thr Leu Pro Gly Ala Glu Ser Gln Arg Glu Ser Pro Ser Thr Gly
        130                 135                 140
Pro Trp Pro Cys Pro Gln Asp Pro Leu Glu Ala Ser Arg Cys Val Val
145                 150                 155                 160
His Gly Ala Glu Phe Trp Ser Glu Tyr Arg Ile Asn Val Thr Glu Val
                165                 170                 175
Asn Pro Leu Gly Ala Ser Thr Cys Leu Leu Asp Val Arg Leu Gln Ser
            180                 185                 190
Ile Leu Arg Pro Asp Pro Pro Gln Gly Leu Arg Val Glu Ser Val Pro
        195                 200                 205
Gly Tyr Pro Arg Arg Leu His Ala Ser Trp Thr Tyr Pro Ala Ser Trp
        210                 215                 220
Arg Arg Gln Pro His Phe Leu Leu Lys Phe Arg Leu Gln Tyr Arg Pro
225                 230                 235                 240
Ala Gln His Pro Ala Trp Ser Thr Val Glu Pro Ile Gly Leu Glu Glu
                245                 250                 255
Val Ile Thr Asp Ala Val Ala Gly Leu Pro His Ala Val Arg Val Ser
            260                 265                 270
Ala Arg Asp Phe Leu Asp Ala Gly Thr Trp Ser Ala Trp Ser Pro Glu
        275                 280                 285
Ala Trp Gly Thr Pro Ser Thr Gly Pro Leu Gln Asp Glu Ile Pro Asp
        290                 295                 300
Trp Ser Gln Gly His Gly Gln Gln Leu Glu Ala Val Ala Gln Glu
305                 310                 315                 320
Asp Ser Pro Ala Pro Ala Arg Pro Ser Leu Gln Pro Asp Pro Arg Pro
                325                 330                 335
Leu Asp His Arg Asp Pro Leu Glu Gln Val Ala Val Leu Ala
            340                 345                 350

<210> SEQ ID NO 27
<211> LENGTH: 348
<212> TYPE: PRT
<213> ORGANISM: Artificial Sequence
<220> FEATURE:
<223> OTHER INFORMATION: Human IL-11Ra ECD

<400> SEQUENCE: 27

Ser Ser Pro Cys Pro Gln Ala Trp Gly Pro Gly Val Gln Tyr Gly
1               5                   10                  15

Gln Pro Gly Arg Ser Val Lys Leu Cys Cys Pro Gly Val Thr Ala Gly
                20                  25                  30

Asp Pro Val Ser Trp Phe Arg Asp Gly Glu Pro Lys Leu Leu Gln Gly
```

```
                35                  40                  45
Pro Asp Ser Gly Leu Gly His Glu Leu Val Leu Ala Gln Ala Asp Ser
 50                  55                  60

Thr Asp Glu Gly Thr Tyr Ile Cys Gln Thr Leu Asp Gly Ala Leu Gly
 65                  70                  75                  80

Gly Thr Val Thr Leu Gln Leu Gly Tyr Pro Pro Ala Arg Pro Val Val
                 85                  90                  95

Ser Cys Gln Ala Ala Asp Tyr Glu Asn Phe Ser Cys Thr Trp Ser Pro
                100                 105                 110

Ser Gln Ile Ser Gly Leu Pro Thr Arg Tyr Leu Thr Ser Tyr Arg Lys
                115                 120                 125

Lys Thr Val Leu Gly Ala Asp Ser Gln Arg Arg Ser Pro Ser Thr Gly
130                 135                 140

Pro Trp Pro Cys Pro Gln Asp Pro Leu Gly Ala Ala Arg Cys Val Val
145                 150                 155                 160

His Gly Ala Glu Phe Trp Ser Gln Tyr Arg Ile Asn Val Thr Glu Val
                165                 170                 175

Asn Pro Leu Gly Ala Ser Thr Arg Leu Leu Asp Val Ser Leu Gln Ser
                180                 185                 190

Ile Leu Arg Pro Asp Pro Pro Gln Gly Leu Arg Val Glu Ser Val Pro
                195                 200                 205

Gly Tyr Pro Arg Arg Leu Arg Ala Ser Trp Thr Tyr Pro Ala Ser Trp
                210                 215                 220

Pro Cys Gln Pro His Phe Leu Leu Lys Phe Arg Leu Gln Tyr Arg Pro
225                 230                 235                 240

Ala Gln His Pro Ala Trp Ser Thr Val Glu Pro Ala Gly Leu Glu Glu
                245                 250                 255

Val Ile Thr Asp Ala Val Ala Gly Leu Pro His Ala Val Arg Val Ser
                260                 265                 270

Ala Arg Asp Phe Leu Asp Ala Gly Thr Trp Ser Thr Trp Ser Pro Glu
                275                 280                 285

Ala Trp Gly Thr Pro Ser Thr Gly Thr Ile Pro Lys Glu Ile Pro Ala
                290                 295                 300

Trp Gly Gln Leu His Thr Gln Pro Glu Val Glu Pro Gln Val Asp Ser
305                 310                 315                 320

Pro Ala Pro Pro Arg Pro Ser Leu Gln Pro His Pro Arg Leu Leu Asp
                325                 330                 335

His Arg Asp Ser Val Glu Gln Val Ala Val Leu Ala
                340                 345

<210> SEQ ID NO 28
<211> LENGTH: 206
<212> TYPE: PRT
<213> ORGANISM: Artificial Sequence
<220> FEATURE:
<223> OTHER INFORMATION: Mouse IL-11Ra D2-D3

<400> SEQUENCE: 28

Pro Pro Ala Arg Pro Glu Val Ser Cys Gln Ala Val Asp Tyr Glu Asn
1               5                  10                  15

Phe Ser Cys Thr Trp Ser Pro Gly Gln Val Ser Gly Leu Pro Thr Arg
                20                  25                  30

Tyr Leu Thr Ser Tyr Arg Lys Lys Thr Leu Pro Gly Ala Glu Ser Gln
                35                  40                  45

Arg Glu Ser Pro Ser Thr Gly Pro Trp Pro Cys Pro Gln Asp Pro Leu
```

```
                    50                  55                  60
Glu Ala Ser Arg Cys Val Val His Gly Ala Glu Phe Trp Ser Glu Tyr
 65                  70                  75                  80

Arg Ile Asn Val Thr Glu Val Asn Pro Leu Gly Ala Ser Thr Cys Leu
                 85                  90                  95

Leu Asp Val Arg Leu Gln Ser Ile Leu Arg Pro Asp Pro Pro Gln Gly
                100                 105                 110

Leu Arg Val Glu Ser Val Pro Gly Tyr Pro Arg Arg Leu His Ala Ser
                115                 120                 125

Trp Thr Tyr Pro Ala Ser Trp Arg Arg Gln Pro His Phe Leu Leu Lys
            130                 135                 140

Phe Arg Leu Gln Tyr Arg Pro Ala Gln His Pro Ala Trp Ser Thr Val
145                 150                 155                 160

Glu Pro Ile Gly Leu Glu Val Ile Thr Asp Ala Val Ala Gly Leu
                165                 170                 175

Pro His Ala Val Arg Val Ser Ala Arg Asp Phe Leu Asp Ala Gly Thr
                180                 185                 190

Trp Ser Ala Trp Ser Pro Glu Ala Trp Gly Thr Pro Ser Thr
            195                 200                 205
```